(12) United States Patent
Lillicrap et al.

(10) Patent No.: US 6,251,632 B1
(45) Date of Patent: Jun. 26, 2001

(54) CANINE FACTOR VIII GENE, PROTEIN AND METHODS OF USE

(75) Inventors: David Lillicrap, Joyceville; Cherie Cameron; Colleen Notley, both of Kingston; L. Suzanne Hoyle Horrocks, Whitby; Christine Hough, Gananoque, all of (CA)

(73) Assignee: Queen's University at Kingston, Kingston (CA)

( * ) Notice: Subject to any disclaimer, the term of this patent is extended or adjusted under 35 U.S.C. 154(b) by 0 days.

(21) Appl. No.: 09/324,867

(22) Filed: Jun. 3, 1999

Related U.S. Application Data

(63) Continuation-in-part of application No. 09/035,141, filed on Mar. 5, 1998, now abandoned.
(60) Provisional application No. 60/039,953, filed on Mar. 6, 1997.

(51) Int. Cl.⁷ .......................... C12P 21/00; C07H 21/04; C12N 15/63; C12N 1/21

(52) U.S. Cl. .................. 435/69.1; 435/455; 435/471; 435/320.1; 435/325; 435/252.3; 435/243; 536/23.1; 536/23.5; 536/24.31

(58) Field of Search .................... 435/69.1, 455, 435/471, 325, 252.3, 243, 320.1; 536/23.1, 23.5, 24.31

(56) References Cited

PUBLICATIONS

Hoyle et al. Thrombosis and Haemostasis, abstract 1945, 1993.*
Cameron, C., et al., "The Canine Factor VIII cDNA and 5' Flanking Sequence," *Thromb. Haemost.* 79:317–322, Schattauer Verlag, Stuttgart, Germany (Feb. 1998).
Windsor, S., et al., "Multiplex analysis of two intragenic microsatellite repeat polymorphisms in the genetic diagnosis of haemophilia A," *Brit. J. Haematol.* 86:810–815 (1994).
Wood, W.I., et al., "Expression of active human factor VIII from recombinant DNA clones," *Nature* 312:330–336 (1984).
Armentano, D., et al., "Expression of human factor IX in rabbit hepatocytes by retrovirus–mediated gene transfer: Potential for gene therapy of hemophilia B," *Proc. Natl. Acad. Sci. USA* 87:6141–6145 (1990).
Axelrod, J.H., et al., "Phenotypic correction of factor IX deficiency in skin fibroblasts of hemophilic dogs," *Proc. Natl. Acad. Sci. USA* 87:5173–5177 (1990).
Bontempo, F.A., et al., "Liver Transplantation in Hemophilia A," *Blood* 69:1721–1724 (1987).
Elder, B., et al., "Sequence of the Murine Factor VIII cDNA," *Genomics* 16:374–379 (1993).
Fass, D.N., et al., "Internal duplication and sequence homology in factors V and VIII," *Proc. Natl. Acad. Sci. USA* 82:1688–1691 (1985).

Fay, P.J., et al., "Inactivation of human factor VIII by activated protein C: evidence that the factor VIII light chain contains the activated protein C binding site," *Biochim. Biophys. Acta* 994:142–148 (1989).
Figueiredo, M.S., et al., "cis–acting Elements and Transcription Factors Involved in the Promoter Activity of the Human Factor VIII Gene," *J. Biol. Chem.* 270:11828–11838 (1995).
Foster, P.A., et al., "An Immunogenic Region within Residues $Val^{1670}$–$Glu^{1684}$ of the Factor VIII Light Chain Induces Antibodies Which Inhibit Binding of Factor VIII to von Willebrand Factor," *J. Biol. Chem.* 263:5230–5234 (1988).
Giles, A.R., et al., "A Canine Model of Hemophilic (Factor VIII:C Deficiency) Bleeding," *Blood* 60:727–730 (1982).
Gitschier, J., et al., "Characterization of the human factor VIII gene," *Nature* 312:326–330 (1984).
Graham, J.B., et al., "Canine Hemophilia: Observations on the Course, the Clotting Anomaly, and the Effect of Blood Transfusions," *J. Exp. Med.* 90:97–111 (1949).
Healey, J.F., et al., "The cDNA and derived amino acid sequence of porcine factor VIII," *Blood* 88:4209–4214 (Dec. 1996).
Hoyer, L.W., "Hemophilia A," *N. Engl. J. Med.* 330:38–47 (1994).
Köhler, G., et al., "Continuous cultures of fused cells secreting antibody of predefined specificity," *Nature* 256:495–497 (1975).
Lind, P., et al., "Novel forms of B–domain–deleted recombinant factor VIII molecules: Construction and biochemical characterization," *Eur. J. Biochem.* 232:19–27 (1995).
McGlynn, L.K., et al., "Role of the Liver–Enriched Transcription Factor Hepatocyte Nuclear Factor 1 in Transcriptional Regulation of the Factor VIII Gene," *Mol. Cell. Biol.* 16:1936–1945 (May 1996).
Palmer, T.D., et al., "Production of Human Factor IX in Animals by Genetically Modified Skin Fibroblasts: Potential Therapy for Hemophilia B," *Blood* 73:438–445 (1989).
Partridge, T.A., et al., "Conversion of mdx myofibres from dystrophin–negative to–positive by injection of normal myoblasts," *Nature* 337:176–179 (1989).
Peake, I., "Registry of DNA Polymorphisms Within or Close to the Human Factor VIII and Factor IX Genes," *Thromb. Haemost.* 67:277–280 (1992).
Pittman, D.D., et al., "Biochemical, Immunological, and In Vivo Functional Characterization of B–Domain–Deleted Factor VIII," *Blood* 81:2925–2935 (1993).

(List continued on next page.)

*Primary Examiner*—Carla J. Myers
(74) *Attorney, Agent, or Firm*—Sterne, Kessler, Goldstein & Fox P.L.L.C.

(57) ABSTRACT

The present invention provides isolated nucleic acid molecules encoding canine factor VIII and allelic variants, mutants, fragments or derivatives thereof. The invention also provides canine factor VIII polypeptides encoded by such isolated nucleic acid molecules, antibodies binding to such polypeptides, genetic constructs comprising such nucleic acid molecules, prokaryotic or eukaryotic host cells comprising such genetic constructs, and methods and compositions for use in diagnosing and treating canine disorders characterized by factor VIII deficiency

37 Claims, 20 Drawing Sheets

OTHER PUBLICATIONS

Pittman, D.D., et al., "Identification and Functional Importance of Tyrosine Sulfate Residues within Recombinant Factor VIII," *Biochem. 31:*3315–3325 (1992).

Pittman, D.D., et al., "Proteolytic requirements for thrombin activation of anti–hemophilic factor (factor VIII)," *Proc. Natl. Acad. Sci. USA* 85:2429–2433 (1988).

Rich, D.P., et al., "Expression of cystic fibrosis transmembrane conductance regulator corrects defective chloride channel regulation in cystic fibrosis airway epithelial cells," *Nature 347:*358–363 (1990).

Rosenberg, S.A., et al., "A New Approach to the Adoptive Immunotherapy of Cancer with Tumor–Infiltrating Lymphocytes," *Science 233:*1318–1321 (1986).

Rosenberg, S.A., et al., "Use of Tumor–infiltrating Lymphocytes and Interleukin–2 in the Immunotherapy of Patients with Metastatic Melanoma," *N. Engl. J. Med. 319:*1676–1680 (1988).

Sorge, J., et al., "Complete correction of the enzymatic defect of type I Gaucher disease fibroblasts by retroviral–mediated gene transfer," *Proc. Natl. Acad. Sci. USA 84:*906–909 (1987).

Steeg, C.M., et al., "Introduction of specific point mutations into RNA polymerase II by gene targeting in mouse embryonic stem cells: Evidence for a DNA mismatch repair mechanism," *Proc. Natl. Acad. Sci. USA 87:*4680–4684 (1990).

Toole, J.J., et al., "A large region ($\approx$95 kDa) of human factor VIII is dispensable for in vitro procoagulant activity," *Proc. Natl. Acad. Sci. USA 83:*5939–5942 (1986).

Toole, J.J., et al., "Molecular cloning of a cDNA encoding human antihaemophilic factor," *Nature 312:*342–347 (1984).

Tuddenham, E.G.D., et al., "Haemophilia A: database of nucleotide substitutions, deletions, insertions and rearrangements of the factor VIII gene, second edition," *Nucl. Acids Res. 22:*3511–3533 (1994).

\* cited by examiner

```
        Met Gln Val Glu Leu Tyr Thr Cys Cys Phe Leu Cys Leu Leu Pro
  1     ATG CAA GTA GAG CTC TAC ACC TGC TGC TTT CTG TGC CTT TTG CCC

Phe Ser Leu Ser Ala Thr Arg Lys Tyr Tyr Leu Gly Ala Val Glu
 46     TTC AGC CTT AGT GCC ACC AGA AAA TAC TAC CTC GGT GCA GTG GAA

Leu Ser Trp Asp Tyr Met Gln Ser Asp Leu Leu Ser Ala Leu His
 91     CTG TCC TGG GAC TAT ATG CAA AGT GAC CTG CTC AGT GCG CTG CAC

Ala Asp Thr Ser Phe Ser Ser Arg Val Pro Gly Ser Leu Pro Leu
136     GCG GAC ACA AGC TTT TCT TCC AGG GTG CCA GGA TCT TTG CCA CTC

Thr Thr Ser Val Thr Tyr Arg Lys Thr Val Phe Val Glu Phe Thr
181     ACC ACG TCA GTC ACG TAC AGA AAG ACT GTG TTT GTA GAG TTT ACA

Asp Asp Leu Phe Asn Ile Ala Lys Pro Arg Pro Pro Trp Met Gly
226     GAT GAC CTT TTC AAC ATT GCC AAG CCC AGG CCA CCG TGG ATG GGC

Leu Leu Gly Pro Thr Ile Gln Ala Glu Val Tyr Asp Thr Val Val
271     CTG CTG GGT CCT ACC ATC CAG GCT GAG GTT TAT GAC ACA GTG GTC

Ile Val Leu Lys Asn Met Ala Ser His Pro Val Ser Leu His Ala
316     ATT GTC CTT AAG AAC ATG GCT TCT CAT CCT GTC AGC CTT CAC GCT

Val Gly Val Ser Tyr Trp Lys Ala Ser Glu Gly Ala Glu Tyr Glu
361     GTT GGT GTA TCC TAT TGG AAA GCT TCT GAA GGT GCT GAG TAT GAG

Asp Gln Thr Ser Gln Lys Glu Lys Glu Asp Asp Asn Val Ile Pro
406     GAT CAG ACC AGC CAA AAG GAG AAG GAA GAT GAT AAT GTC ATT CCT

Gly Glu Ser His Thr Tyr Val Trp Gln Val Leu Lys Glu Asn Gly
451     GGT GAA AGC CAT ACC TAT GTC TGG CAG GTC CTG AAA GAG AAT GGC

Pro Met Ala Ser Asp Pro Pro Cys Leu Thr Tyr Ser Tyr Phe Ser
496     CCA ATG GCC TCT GAT CCA CCA TGT CTC ACC TAC TCA TAT TTT TCA

His Val Asp Leu Val Lys Asp Leu Asn Ser Gly Leu Ile Gly Ala
541     CAC GTG GAC CTG GTG AAA GAC CTG AAT TCA GGC CTC ATT GGA GCC

Leu Leu Val Cys Lys Glu Gly Ser Leu Ala Lys Glu Arg Thr Gln
586     CTG CTG GTT TGC AAA GAA GGG AGT CTG GCC AAA GAA AGG ACA CAG

Thr Leu Gln Glu Phe Val Leu Leu Phe Ala Val Phe Asp Glu Gly
631     ACC TTG CAG GAA TTT GTC CTA CTT TTT GCT GTA TTT GAT GAA GGG

Lys Ser Trp His Ser Glu Thr Asn Ala Ser Leu Thr Gln Ala Glu
676     AAA AGT TGG CAC TCA GAA ACA AAT GCG TCT TTG ACA CAG GCT GAG
```

FIGURE 1A

```
         Ala Gln His Glu Leu His Thr Ile Asn Gly Tyr Val Asn Arg Ser
  721    GCC CAG CAT GAG CTG CAC ACC ATC AAT GGC TAT GTA AAC AGG TCT

Leu Pro Gly Leu Thr Val Cys His Lys Arg Ser Val Tyr Trp His
  766    CTG CCA GGT CTT ACT GTG TGT CAC AAG AGA TCA GTC TAT TGG CAT

Val Ile Gly Met Gly Thr Thr Pro Glu Val His Ser Ile Phe Leu
  811    GTG ATT GGA ATG GGC ACC ACC CCC GAA GTG CAC TCA ATT TTT CTC

Glu Gly His Thr Phe Leu Val Arg Asn His Arg Gln Ala Ser Leu
  856    GAA GGT CAC ACA TTT CTT GTG AGG AAC CAC CGC CAG GCC TCC TTG

Glu Ile Ser Pro Ile Thr Phe Leu Thr Ala Gln Thr Phe Leu Met
  901    GAG ATC TCA CCA ATT ACT TTC CTT ACT GCT CAG ACA TTC CTG ATG

Asp Leu Gly Gln Phe Leu Leu Phe Cys His Ile Pro Ser His Gln
  946    GAC CTT GGC CAG TTT CTA CTG TTT TGT CAT ATC CCT TCC CAT CAA

His Asp Gly Met Glu Ala Tyr Val Lys Val Asp Ser Cys Pro Glu
  991    CAT GAT GGT ATG GAA GCT TAT GTC AAA GTA GAT AGC TGC CCA GAG

Glu Pro Gln Leu Arg Met Lys Asn Asn Glu Asp Lys Asp Tyr Asp
 1036    GAA CCC CAG CTG CGC ATG AAA AAT AAT GAA GAT AAA GAT TAT GAT

Asp Gly Leu Tyr Asp Ser Asp Met Asp Val Val Ser Phe Asp Asp
 1081    GAT GGT CTT TAT GAT TCT GAC ATG GAC GTA GTT AGC TTT GAT GAC

Asp Ser Ser Ser Pro Phe Ile Gln Ile Arg Ser Val Ala Lys Lys
 1126    GAC AGC TCT TCT CCC TTT ATC CAA ATC CGC TCA GTT GCC AAG AAG

His Pro Lys Thr Trp Val His Tyr Ile Ala Ala Glu Glu Glu Asp
 1171    CAT CCT AAA ACT TGG GTC CAC TAT ATT GCT GCT GAG GAG GAG GAC

Trp Asp Tyr Ala Pro Ser Gly Pro Thr Pro Asn Asp Arg Ser His
 1216    TGG GAC TAT GCT CCC TCA GGC CCC ACC CCC AAT GAT AGA AGT CAT

Lys Asn Leu Tyr Leu Asn Asn Gly Pro Gln Arg Ile Gly Lys Lys
 1261    AAA AAT CTG TAT TTG AAC AAT GGT CCT CAG CGG ATT GGT AAG AAG

Tyr Lys Lys Val Arg Phe Val Ala Tyr Thr Asp Glu Thr Phe Lys
 1306    TAC AAA AAA GTC CGA TTT GTG GCA TAC ACA GAT GAG ACA TTT AAG

Thr Arg Glu Ala Ile Gln Tyr Glu Ser Gly Ile Leu Gly Pro Leu
 1351    ACT CGT GAA GCT ATT CAG TAT GAA TCA GGA ATC CTG GGA CCT TTA

Leu Tyr Gly Glu Val Gly Asp Thr Leu Leu Ile Ile Phe Lys Asn
 1396    CTT TAT GGA GAA GTT GGA GAC ACA CTG CTG ATT ATA TTT AAG AAT
```

FIGURE 1B

```
          Gln Ala Ser Arg Pro Tyr Asn Ile Tyr Pro His Gly Ile Asn Tyr
1441      CAA GCC AGC CGG CCA TAT AAC ATC TAC CCT CAT GGG ATC AAT TAT

Val Thr Pro Leu His Thr Gly Arg Leu Pro Lys Gly Val Lys His
1486      GTC ACT CCT CTG CAC ACA GGG AGA TTG CCA AAA GGT GTG AAA CAT

Leu Lys Asp Met Pro Ile Leu Pro Gly Glu Ile Phe Lys Tyr Lys
1531      TTG AAA GAT ATG CCA ATT CTG CCG GGA GAG ATA TTC AAG TAT AAA

Trp Thr Val Thr Val Glu Asp Gly Pro Thr Lys Ser Asp Pro Arg
1576      TGG ACA GTG ACC GTA GAA GAT GGA CCA ACT AAA TCA GAT CCT CGG

Cys Leu Thr Arg Tyr Tyr Ser Ser Phe Ile Asn Leu Glu Arg Asp
1621      TGC CTG ACC CGA TAT TAC TCA AGC TTC ATT AAT CTG GAG AGA GAT

Leu Ala Ser Gly Leu Ile Gly Pro Leu Leu Ile Cys Tyr Lys Glu
1666      CTA GCT TCA GGA CTC ATT GGC CCT CTT CTC ATC TGC TAC AAA GAA

Ser Val Asp Gln Arg Gly Asn Gln Met Met Ser Asp Lys Arg Asn
1711      TCT GTA GAT CAA AGA GGA AAC CAG ATG ATG TCA GAC AAG AGA AAT

Val Ile Leu Phe Ser Val Phe Asp Glu Asn Arg Ser Trp Tyr Leu
1756      GTC ATC CTG TTT TCT GTA TTT GAT GAG AAT CGA AGC TGG TAC CTC

Thr Glu Asn Met Gln Arg Phe Leu Pro Asn Ala Asp Val Val Gln
1801      ACA GAG AAT ATG CAG CGC TTC CTC CCC AAT GCA GAT GTA GTG CAG

Pro His Asp Pro Glu Phe Gln Leu Ser Asn Ile Met His Ser Ile
1846      CCC CAT GAC CCA GAG TTC CAA CTC TCT AAC ATC ATG CAC AGC ATC

Asn Gly Tyr Val Phe Asp Asn Leu Gln Leu Ser Val Cys Leu His
1891      AAT GGC TAT GTT TTT GAC AAC TTG CAG CTG TCA GTT TGT TTG CAT

Glu Val Ala Tyr Trp Tyr Ile Leu Ser Val Gly Ala Gln Thr Asp
1936      GAG GTG GCG TAC TGG TAC ATT CTA AGT GTT GGA GCA CAA ACT GAC

Phe Leu Ser Val Phe Phe Ser Gly Tyr Thr Phe Lys His Lys Met
1981      TTC CTG TCT GTC TTC TTC TCT GGA TAT ACC TTC AAA CAC AAA ATG

Val Tyr Glu Asp Thr Leu Thr Leu Phe Pro Phe Ser Gly Glu Thr
2026      GTC TAT GAA GAC ACA CTT ACC CTC TTC CCA TTC TCA GGA GAA ACT

Val Phe Met Ser Met Glu Asn Pro Gly Leu Trp Val Leu Gly Cys
2071      GTC TTC ATG TCA ATG GAA AAC CCA GGT CTG TGG GTT CTG GGG TGC

His Asn Ser Asp Phe Arg Asn Arg Gly Met Thr Ala Leu Leu Lys
2116      CAC AAC TCA GAC TTT CGG AAC AGA GGC ATG ACA GCC TTA CTG AAG
```

FIGURE 1C

```
       Val Ser Ser Cys Asn Arg Asn Ile Asp Asp Tyr Tyr Glu Asp Thr
2161   GTT TCT AGT TGT AAC AGG AAC ATT GAT GAT TAT TAT GAG GAC ACA

Tyr Glu Asp Ile Pro Thr Pro Leu Leu Asn Glu Asn Asn Val Ile
2206   TAC GAA GAT ATT CCA ACT CCC CTG CTA AAT GAA AAC AAT GTA ATT

Lys Pro Arg Ser Phe Ser Gln Asn Ser Arg His Pro Ser Thr Lys
2251   AAA CCT AGA AGC TTC TCC CAG AAT TCA AGG CAC CCT AGC ACT AAG

Glu Lys Gln Leu Lys Ala Thr Thr Thr Pro Glu Asn Asp Ile Glu
2296   GAA AAG CAA TTG AAA GCC ACC ACA ACT CCA GAA AAT GAC ATA GAG

Lys Ile Asp Leu Gln Ser Gly Glu Arg Thr Gln Leu Ile Lys Ala
2341   AAG ATT GAC CTT CAA TCT GGA GAA AGA ACA CAG CTG ATT AAA GCA

Gln Ser Val Ser Ser Ser Asp Leu Leu Met Leu Leu Gly Gln Asn
2386   CAA AGT GTC TCC TCT AGT GAT TTG TTG ATG CTG TTG GGA CAG AAT

Pro Thr Pro Arg Gly Leu Phe Leu Ser Asp Leu Arg Glu Ala Thr
2431   CCT ACT CCA CGT GGA CTG TTC TTA TCT GAT CTC CGA GAG GCC ACA

Asp Arg Ala Asp Asp His Ser Arg Gly Ala Ile Glu Arg Asn Lys
2476   GAT AGA GCC GAT GAC CAT TCA CGT GGA GCA ATA GAA AGA AAC AAG

Gly Pro Pro Glu Val Ala Ser Leu Arg Pro Glu Leu Arg His Ser
2521   GGC CCA CCT GAA GTG GCA AGT CTC AGA CCA GAG CTC CGT CAC AGT

Glu Asp Arg Glu Phe Thr Pro Glu Pro Glu Leu Gln Leu Arg Leu
2566   GAG GAC AGA GAA TTT ACT CCT GAG CCA GAA CTG CAG TTA AGA TTA

Asn Glu Asn Leu Gly Thr Asn Thr Thr Val Glu Leu Lys Lys Leu
2611   AAT GAG AAT TTG GGG ACA AAT ACA ACA GTA GAG TTG AAG AAA CTT

Asp Leu Lys Ile Ser Ser Ser Ser Asp Ser Leu Met Thr Ser Pro
2656   GAT TTA AAA ATT TCT AGT TCA TCA GAC AGT CTA ATG ACT TCA CCA

Thr Ile Pro Ser Asp Lys Leu Ala Ala Ala Thr Glu Lys Thr Gly
2701   ACA ATT CCA TCA GAT AAG TTG GCA GCA GCT ACT GAA AAG ACA GGT

Ser Leu Gly Pro Pro Asn Met Ser Val His Phe Asn Ser His Leu
2746   TCC TTA GGA CCC CCA AAT ATG TCA GTT CAC TTT AAC AGT CAT TTA

Gly Thr Ile Val Phe Gly Asn Asn Ser Ser His Leu Ile Gln Ser
2791   GGT ACC ATT GTA TTT GGC AAT AAT TCA TCC CAC CTT ATT CAG TCT

Gly Val Pro Leu Glu Leu Ser Glu Glu Asp Asn Asp Ser Lys Leu
2836   GGT GTA CCT TTG GAA TTG AGT GAA GAA GAT AAT GAT TCC AAG TTG
```

FIGURE 1D

```
         Leu Glu Ala Pro Leu Met Asn Ile Gln Glu Ser Ser Leu Arg Glu
2881     TTA GAA GCA CCT TTA ATG AAT ATT CAA GAA AGT TCA CTG AGA GAA

Asn Val Leu Ser Met Glu Ser Asn Arg Leu Phe Lys Glu Glu Arg
2926     AAT GTA TTA TCA ATG GAG AGT AAT AGG TTA TTT AAA GAA GAA AGA

Ile Arg Gly Pro Ala Ser Leu Ile Lys Asp Asn Ala Leu Phe Lys
2971     ATT CGT GGA CCT GCT TCA TTA ATC AAA GAT AAT GCT TTA TTC AAA

Val Asn Ile Ser Ser Val Lys Thr Asn Arg Ala Pro Val Asn Leu
3016     GTT AAT ATC TCT TCG GTA AAG ACA AAC AGG GCA CCA GTT AAC TTA

Thr Thr Asn Arg Lys Thr Arg Val Ala Ile Pro Thr Leu Leu Ile
3061     ACA ACT AAT AGA AAG ACT CGT GTT GCT ATC CCA ACA TTA TTA ATT

Glu Asn Ser Thr Ser Val Trp Gln Asp Ile Met Leu Glu Arg Asn
3106     GAG AAC AGT ACC TCA GTC TGG CAA GAT ATT ATG TTA GAA AGG AAT

Thr Glu Phe Lys Glu Val Thr Ser Leu Ile His Asn Glu Thr Phe
3151     ACT GAG TTT AAA GAA GTA ACT TCT TTG ATT CAT AAT GAA ACG TTT

Met Asp Arg Asn Thr Thr Ala Leu Gly Leu Asn His Val Ser Asn
3196     ATG GAC AGA AAT ACT ACA GCT CTG GGG CTA AAT CAT GTG TCA AAT

Lys Thr Thr Leu Ser Lys Asn Val Glu Met Ala His Gln Lys Lys
3241     AAA ACT ACT TTA TCA AAA AAT GTG GAA ATG GCC CAC CAA AAA AAA

Glu Asp Pro Val Pro Leu Arg Ala Glu Asn Pro Asp Leu Ser Ser
3286     GAA GAC CCT GTG CCA CTA CGT GCA GAA AAT CCA GAT CTA TCA TCC

Ser Lys Ile Pro Phe Leu Pro Asp Trp Ile Lys Thr His Gly Lys
3331     TCC AAG ATA CCG TTC TTG CCA GAT TGG ATA AAG ACC CAT GGC AAG

Asn Ser Leu Ser Ser Glu Gln Arg Pro Ser Pro Lys Gln Leu Thr
3376     AAC TCC CTA AGC TCT GAG CAA AGG CCC AGT CCA AAA CAA TTA ACA

Ser Leu Gly Ser Glu Lys Ser Val Lys Asp Gln Asn Phe Leu Ser
3421     TCT TTA GGA TCA GAA AAA TCT GTG AAA GAT CAG AAC TTT TTG TCA

Glu Glu Lys Val Val Val Gly Glu Asp Glu Phe Thr Lys Asp Thr
3466     GAG GAG AAG GTG GTA GTA GGA GAG GAT GAA TTT ACG AAG GAC ACA

Glu Leu Gln Glu Ile Phe Pro Asn Asn Lys Ser Ile Phe Phe Ala
3511     GAA CTC CAA GAG ATT TTT CCA AAC AAC AAG AGC ATA TTT TTT GCT

Asn Leu Ala Asn Val Gln Glu Asn Asp Thr Tyr Asn Gln Glu Lys
3556     AAC TTG GCT AAT GTC CAA GAA AAT GAT ACA TAC AAT CAA GAA AAA
```

FIGURE 1E

```
      Lys Ser Pro Glu Glu Ile Glu Arg Lys Glu Lys Leu Thr Gln Glu
3601  AAA TCT CCG GAA GAG ATA GAA AGA AAG GAA AAA TTA ACC CAG GAG

Asn Val Ala Leu Pro Gln Ala His Thr Met Ile Gly Thr Lys Asn
3646  AAT GTG GCT TTG CCT CAG GCA CAT ACT ATG ATT GGC ACT AAG AAC

Phe Leu Lys Asn Leu Phe Leu Leu Ser Thr Lys Gln Asn Val Ala
3691  TTC CTG AAG AAC CTT TTC TTA CTA AGC ACT AAG CAA AAT GTA GCA

Gly Leu Glu Glu Gln Pro Tyr Thr Pro Ile Leu Gln Asp Thr Arg
3736  GGT TTA GAA GAG CAG CCA TAT ACT CCA ATA CTT CAA GAC ACC AGG

Ser Leu Asn Asp Ser Pro His Ser Glu Gly Ile His Met Ala Asn
3781  TCA TTA AAT GAT TCG CCA CAT AGT GAA GGG ATT CAT ATG GCC AAT

Phe Ser Lys Ile Arg Glu Glu Ala Asn Leu Glu Gly Leu Gly Asn
3826  TTC TCA AAA ATA AGG GAA GAA GCA AAC TTG GAA GGC TTG GGA AAT

Gln Thr Asn Gln Met Val Glu Arg Phe Pro Ser Thr Thr Arg Met
3871  CAA ACA AAC CAA ATG GTA GAG AGG TTT CCA AGC ACT ACG AGG ATG

Ser Ser Asn Ala Ser Gln His Val Ile Thr Gln Arg Gly Lys Arg
3916  TCT TCT AAT GCA AGT CAG CAT GTT ATC ACT CAA CGT GGT AAG CGG

Ser Leu Lys Gln Pro Arg Leu Ser Gln Gly Glu Ile Lys Phe Glu
3961  AGT TTG AAA CAA CCC AGA CTC TCA CAA GGA GAA ATA AAG TTT GAA

Arg Lys Val Ile Ala Asn Asp Thr Ser Thr Gln Trp Ser Lys Asn
4006  AGG AAG GTT ATT GCA AAT GAC ACT TCA ACC CAG TGG TCC AAA AAC

Met Asn Tyr Leu Ala Gln Gly Thr Leu Thr Gln Ile Glu Tyr Asn
4051  ATG AAC TAT TTG GCC CAG GGA ACC CTC ACA CAG ATA GAG TAT AAT

Glu Lys Glu Lys Arg Ala Ile Thr Gln Ser Pro Leu Ser Asp Cys
4096  GAG AAA GAA AAA AGG GCC ATT ACT CAG TCC CCC CTA TCA GAT TGT

Ser Met Arg Asn His Val Thr Ile Gln Met Asn Asp Ser Ala Leu
4141  TCT ATG AGG AAT CAT GTC ACC ATT CAA ATG AAT GAC TCT GCA TTA

Pro Val Ala Lys Glu Ser Ala Ser Pro Ser Val Arg His Thr Asp
4186  CCC GTT GCA AAG GAA TCA GCA TCT CCA TCA GTT AGA CAT ACA GAT

Leu Thr Lys Ile Pro Ser Gln His Asn Ser Ser His Leu Pro Ala
4231  CTG ACC AAG ATC CCA TCC CAA CAC AAC TCT TCT CAT CTT CCA GCA

Ser Ala Cys Asn Tyr Thr Phe Arg Glu Arg Thr Ser Gly Val Gln
4276  TCA GCC TGT AAT TAT ACC TTT AGA GAG AGG ACT TCT GGA GTC CAA
```

FIGURE 1F

```
      Glu Gly Ser His Phe Leu Gln Glu Ala Lys Arg Asn Asn Leu Ser
4321  GAA GGC AGT CAT TTC TTA CAA GAA GCC AAA AGA AAT AAC CTC TCT

Leu Ala Phe Val Thr Leu Gly Ile Thr Glu Gly Gln Gly Lys Phe
4366  TTA GCC TTT GTA ACC TTA GGA ATA ACT GAA GGG CAA GGA AAG TTC

Ser Ser Leu Gly Lys Ser Ala Thr Asn Gln Pro Met Tyr Lys Lys
4411  AGC TCC CTG GGG AAA AGT GCC ACA AAC CAA CCC ATG TAC AAG AAA

Leu Glu Asn Thr Val Leu Leu Gln Pro Gly Leu Ser Glu Thr Ser
4456  CTT GAA AAC ACT GTT CTC TTG CAA CCA GGC TTG TCC GAA ACA TCT

Asp Lys Val Glu Leu Leu Ser Gln Val His Val Asp Gln Glu Asp
4501  GAC AAA GTT GAA TTA CTT TCT CAA GTT CAT GTT GAT CAA GAA GAC

Ser Phe Pro Thr Lys Thr Ser Asn Asp Ser Pro Gly His Leu Asp
4546  TCT TTC CCT ACA AAA ACT AGC AAT GAT TCT CCT GGC CAC CTG GAT

Leu Met Gly Lys Ile Phe Leu Gln Lys Thr Gln Gly Pro Val Lys
4591  CTC ATG GGA AAG ATC TTC CTT CAG AAA ACA CAG GGA CCT GTT AAA

Met Asn Lys Thr Asn Ser Pro Gly Lys Val Pro Phe Leu Lys Trp
4636  ATG AAT AAA ACA AAT AGC CCT GGA AAA GTG CCC TTT CTG AAA TGG

Ala Thr Glu Ser Ser Glu Lys Ile Pro Ser Lys Leu Leu Gly Val
4681  GCA ACA GAA AGC TCT GAA AAG ATT CCC TCC AAG CTG CTG GGT GTC

Leu Ala Trp Asp Asn His Tyr Asp Thr Gln Ile Pro Ser Glu Glu
4726  CTT GCT TGG GAT AAC CAC TAT GAT ACC CAG ATA CCA AGT GAA GAG

Trp Lys Ser Gln Lys Lys Ser Gln Thr Asn Thr Ala Phe Lys Arg
4771  TGG AAA TCC CAA AAA AAG TCA CAG ACG AAC ACA GCT TTT AAA AGG

Lys Asp Thr Ile Leu Pro Leu Gly Pro Cys Glu Asn Asn Asp Ser
4816  AAA GAC ACC ATT TTG CCC CTG GGC CCT TGT GAA AAT AAT GAT TCA

Thr Ala Ala Ile Asn Glu Gly Gln Asp Lys Pro Gln Arg Glu Ala
4861  ACA GCA GCA ATA AAT GAA GGA CAA GAT AAG CCC CAA AGA GAA GCT

Met Trp Ala Lys Gln Gly Glu Pro Gly Arg Leu Cys Ser Gln Asn
4906  ATG TGG GCA AAG CAA GGA GAG CCT GGA AGG TTG TGC TCT CAA AAC

Pro Pro Val Ser Lys His His Gln Arg Glu Ile Thr Val Thr Thr
4951  CCA CCA GTC TCA AAA CAC CAT CAA AGG GAA ATA ACC GTT ACT ACT

Leu Gln Pro Glu Glu Asp Lys Phe Glu Tyr Asp Asp Thr Phe Ser
4996  CTT CAG CCA GAG GAA GAC AAA TTT GAG TAT GAT GAC ACC TTC TCA
```

FIGURE 1G

```
        Ile Glu Met Lys Arg Glu Asp Phe Asp Ile Tyr Gly Asp Tyr Glu
5041    ATT GAA ATG AAG AGA GAA GAT TTT GAC ATC TAC GGC GAC TAT GAA

Asn Gln Gly Leu Arg Ser Phe Gln Lys Lys Thr Arg His Tyr Phe
5086    AAT CAG GGC CTC CGC AGC TTT CAA AAG AAA ACA CGA CAC TAT TTC

Ile Ala Ala Val Glu Arg Leu Trp Asp Tyr Gly Met Ser Arg Ser
5131    ATT GCT GCA GTG GAG CGT CTC TGG GAT TAT GGG ATG AGT AGA TCT

Pro His Ile Leu Arg Asn Arg Ala Gln Ser Gly Asp Val Gln Gln
5176    CCC CAT ATA CTA AGA AAC AGG GCT CAA AGT GGG GAT GTC CAG CAG

Phe Lys Lys Val Val Phe Gln Glu Phe Thr Asp Gly Ser Phe Thr
5221    TTC AAG AAG GTG GTT TTC CAG GAA TTT ACT GAT GGA TCC TTT ACT

Gln Pro Leu Tyr Arg Gly Glu Leu Asn Glu His Leu Gly Leu Leu
5266    CAG CCC TTA TAC CGT GGA GAA CTG AAC GAA CAC TTG GGA CTC TTG

Gly Pro Tyr Ile Arg Ala Glu Val Glu Asp Asn Ile Val Val Thr
5311    GGG CCA TAT ATA AGA GCA GAA GTT GAA GAC AAT ATC GTG GTA ACT

Phe Lys Asn Gln Ala Ser Arg Pro Tyr Ser Phe Tyr Ser Ser Leu
5356    TTC AAA AAC CAG GCC TCT CGT CCC TAC TCC TTC TAT TCT AGT CTT

Ile Ser Tyr Asp Glu Asp Glu Gly Gln Gly Ala Glu Pro Arg Arg
5401    ATT TCT TAT GAC GAA GAT GAG GGA CAA GGA GCA GAA CCT AGA AGA

Lys Phe Val Asn Pro Asn Glu Thr Lys Ile Tyr Phe Trp Lys Val
5446    AAG TTT GTC AAC CCT AAT GAA ACC AAA ATT TAC TTT TGG AAA GTG

Gln His His Met Ala Pro Thr Lys Asp Glu Phe Asp Cys Lys Ala
5491    CAG CAT CAT ATG GCA CCC ACT AAA GAT GAG TTT GAC TGC AAA GCC

Trp Ala Tyr Phe Ser Asp Val Asp Leu Glu Lys Asp Val His Ser
5536    TGG GCT TAT TTT TCT GAT GTT GAT CTG GAG AAA GAT GTG CAC TCA

Gly Leu Ile Gly Pro Leu Leu Ile Cys Arg Ser Asn Thr Leu Asn
5581    GGC TTG ATT GGA CCC CTT CTG ATC TGC CGC AGT AAC ACA CTG AAC

Pro Ala His Gly Arg Gln Val Thr Val Gln Glu Phe Ala Leu Val
5626    CCT GCT CAT GGG AGA CAA GTG ACA GTG CAG GAG TTT GCC CTG GTT

Phe Thr Ile Phe Asp Glu Thr Lys Ser Trp Tyr Phe Thr Glu Asn
5671    TTC ACT ATA TTC GAT GAG ACT AAG AGC TGG TAC TTC ACT GAA AAC

Leu Glu Arg Asn Cys Arg Ala Pro Cys Asn Val Gln Lys Glu Asp
5716    CTG GAA AGG AAC TGC AGA GCT CCC TGC AAT GTC CAG AAG GAG GAC
```

FIGURE 1H

```
            Pro Thr Leu Lys Glu Asn Phe Arg Phe His Ala Ile Asn Gly Tyr
      5761  CCT ACT CTA AAA GAA AAC TTC CGC TTC CAT GCA ATC AAC GGC TAT

Val Lys Asp Thr Leu Pro Gly Leu Val Met Ala Gln Asp Gln Lys
      5806  GTG AAG GAT ACA CTC CCT GGC TTA GTA ATG GCT CAG GAT CAA AAG

Val Arg Trp Tyr Leu Leu Ser Met Gly Ser Asn Glu Asn Ile His
      5851  GTT CGA TGG TAT CTG CTC AGC ATG GGC AGC AAC GAA AAC ATT CAT

Ser Ile His Phe Ser Gly His Val Phe Thr Val Arg Lys Lys Glu
      5896  TCC ATT CAC TTC AGT GGA CAT GTG TTC ACT GTA CGG AAA AAA GAG

Glu Tyr Lys Met Ala Val Tyr Asn Leu Tyr Pro Gly Val Phe Glu
      5941  GAA TAT AAA ATG GCA GTC TAC AAC CTC TAT CCA GGT GTT TTT GAG

Thr Val Glu Met Leu Pro Ser Gln Val Gly Ile Trp Arg Ile Glu
      5986  ACT GTG GAA ATG CTA CCA TCC CAA GTT GGA ATC TGG CGG ATA GAA

Cys Leu Ile Gly Glu His Leu Gln Ala Gly Met Ser Thr Leu Phe
      6031  TGC CTT ATC GGC GAG CAC CTG CAA GCC GGG ATG AGC ACT CTG TTT

Leu Val Tyr Ser Lys Lys Cys Gln Thr Pro Leu Gly Met Ala Ser
      6076  CTG GTG TAC AGC AAG AAG TGT CAG ACT CCA CTG GGG ATG GCT TCC

Gly His Ile Arg Asp Phe Gln Ile Thr Ala Ser Gly Gln Tyr Gly
      6121  GGA CAC ATT AGA GAT TTT CAG ATT ACA GCT TCA GGA CAA TAT GGA

Gln Trp Ala Pro Lys Leu Ala Arg Leu His Tyr Ser Gly Ser Ile
      6166  CAG TGG GCC CCA AAG CTG GCC AGA CTT CAT TAT TCC GGA TCA ATC

Asn Ala Trp Ser Thr Lys Asp Pro Phe Ser Trp Ile Lys Val Asp
      6211  AAT GCC TGG AGC ACC AAG GAT CCC TTT TCC TGG ATC AAG GTG GAT

Leu Leu Ala Pro Met Ile Ile His Gly Ile Met Thr Gln Gly Ala
      6256  CTC TTG GCA CCG ATG ATT ATT CAC GGC ATC ATG ACC CAG GGG GCC

Arg Gln Lys Phe Ser Ser Leu Tyr Val Ser Gln Phe Ile Ile Met
      6301  CGC CAG AAG TTC TCC AGC CTC TAC GTG TCT CAG TTT ATC ATC ATG

Tyr Ser Leu Asp Gly Asn Lys Trp His Ser Tyr Arg Gly Asn Ser
      6346  TAC AGT CTG GAT GGC AAC AAG TGG CAC AGT TAC CGA GGG AAT TCC

Thr Gly Thr Leu Met Val Phe Phe Gly Asn Val Asp Ser Ser Gly
      6391  ACG GGA ACC TTA ATG GTC TTC TTT GGC AAC GTG GAT TCA TCT GGG

Ile Lys His Asn Ile Phe Asn Pro Pro Ile Ile Ala Gln Tyr Ile
      6436  ATC AAA CAC AAT ATT TTT AAC CCT CCG ATT ATT GCT CAG TAC ATC
```

FIGURE 1I

```
        Arg Leu His Pro Thr His Tyr Ser Ile Arg Ser Thr Leu Arg Met
6481    CGT TTG CAC CCA ACC CAT TAC AGC ATC CGC AGC ACT CTT CGC ATG

Glu Leu Leu Gly Cys Asp Phe Asn Ser Cys Ser Met Pro Leu Gly
6526    GAG CTC TTG GGC TGT GAC TTC AAC AGT TGC AGC ATG CCG CTG GGG

Met Glu Ser Lys Ala Ile Ser Asp Ala Gln Ile Thr Ala Ser Ser
6571    ATG GAG AGT AAA GCA ATA TCA GAT GCT CAG ATC ACT GCC TCG TCC

Tyr Leu Ser Ser Met Leu Ala Thr Trp Ser Pro Ser Gln Ala Arg
6616    TAC CTA AGC AGT ATG CTT GCC ACT TGG TCT CCT TCC CAA GCC CGG

Leu His Leu Gln Gly Arg Thr Asn Ala Trp Arg Pro Gln Ala Asn
6661    CTG CAC CTG CAG GGC AGG ACT AAT GCC TGG AGA CCT CAG GCA AAT

Asn Pro Lys Glu Trp Leu Gln Val Asp Phe Arg Lys Thr Met Lys
6706    AAC CCA AAA GAG TGG CTG CAA GTG GAC TTC CGG AAG ACC ATG AAA

Val Thr Gly Ile Thr Thr Gln Gly Val Lys Ser Leu Leu Ile Ser
6751    GTC ACA GGA ATA ACC ACC CAG GGG GTG AAA TCT CTC CTC ATC AGC

Met Tyr Val Lys Glu Phe Leu Ile Ser Ser Ser Gln Asp Gly His
6796    ATG TAT GTG AAG GAG TTC CTC ATC TCC AGT AGT CAA GAT GGC CAT

Asn Trp Thr Leu Phe Leu Gln Asn Gly Lys Val Lys Val Phe Gln
6841    AAC TGG ACT CTG TTT CTT CAG AAT GGC AAA GTC AAG GTC TTC CAG

Gly Asn Arg Asp Ser Ser Thr Pro Val Arg Asn Arg Leu Glu Pro
6886    GGA AAC CGG GAC TCC TCC ACG CCT GTG CGG AAC CGT CTC GAA CCC

Pro Leu Val Ala Arg Tyr Val Arg Leu His Pro Gln Ser Trp Ala
6931    CCG CTG GTG GCT CGC TAC GTG CGC CTG CAC CCG CAG AGC TGG GCG

His His Ile Ala Leu Arg Leu Glu Val Leu Gly Cys Asp Thr Gln
6976    CAC CAC ATC GCC CTG AGG CTG GAG GTC CTG GGC TGC GAC ACC CAG

Gln Pro Ala ***
7021    CAG CCC GCC TGA
```

FIGURE 1J

```
DOGLESSI    1   ATRKYYLGAVELSWDYMQSDLLSALHADTSFSSRVPGSLPLTTSVTYRKT
HUMLESSI    1   ATRRYYLGAVELSWDYMQSDL-GELPVDARFPPRVPKSFPFNTSVVYKKT
MULESSI     1   AIRRYYLGAVELSWNYIQSDLLSVLHTDSRFLPRMSTSFPFNTSIMYKKT
PIGLESSI    1   AIRRYYLGAVELSWDYRQSELLRELHVDTRFPATAPGALPLGPSVLYKKT

DOGLESSI   51   VFVEFTDDLFNIAKPRPPWMGLLGPTIQAEVYDTVVIVLKNMASHPVSLH
HUMLESSI   50   LFVEFTVHLFNIAKPRPPWMGLLGPTIQAEVYDTVVITLKNMASHPVSLH
MULESSI    51   VFVEYKDQLFNIAKPRPPWMGLLGPTIWTEVHDTVVITLKNMASHPVSLH
PIGLESSI   51   VFVEFTDQLFSVARPRPPWMGLLGPTIQAEVYDTVVVTLKNMASHPVSLH

DOGLESSI  101   AVGVSYWKASEGAEYEDQTSQKEKEDDNVIPGESHTYVWQVLKENGPMAS
HUMLESSI  100   AVGVSYWKASEGAEYDDQTSQREKEDDKVFPGGSHTYVWQVLKENGPMAS
MULESSI   101   AVGVSYWKASEGDEYEDQTSQMEKEDDKVFPGESHTYVWQVLKENGPMAS
PIGLESSI  101   AVGVSFWKSSEGAEYEDHTSQREKEDDKVLPGKSQTYVWQVLKENGPTAS

DOGLESSI  151   DPPCLTYSYFSHVDLVKDLNSGLIGALLVCKEGSLAKERTQTLQEFVLLF
HUMLESSI  150   DPLCLTYSYLSHVDLVKDLNSGLIGALLVCREGSLAKEKTQTLHKFILLF
MULESSI   151   DPPCLTYSYMSHVDLVKDLNSGLIGALLVCKEGSLSKERTQMLYQFVLLF
PIGLESSI  151   DPPCLTYSYLSHVDLVKDLNSGLIGALLVCREGSLTRERTQNLHEFVLLF

DOGLESSI  201   AVFDEGKSWHSETNASLTQAEAQ------HELHTINGYVNRSLPGLTVCH
HUMLESSI  200   AVFDEGKSWHSETKNSLMQDRDAASARAWPKMHTVNGYVNRSLPGLIGCH
MULESSI   201   AVFDEGKSWHSETNDSYTQSMDSASARDWPKMHTVNGYVNRSLPGLIGCH
PIGLESSI  201   AVFDEGKSWHSARNDSWTRAMDPAPARAQPAMHTVNGYVNRSLPGLIGCH

DOGLESSI  245   KRSVYWHVIGMGTTPEVHSIFLEGHTFLVRNHRQASLEISPITFLTAQTF
HUMLESSI  250   RKSVYWHVIGMGTTPEVHSIFLEGHTFLVRNHRQASLEISPITFLTAQTL
MULESSI   251   RKSVYWHVIGMGTTPEIHSIFLEGHTFFVRNHRQASLEISPITFLTAQTL
PIGLESSI  251   KKSVYWHVIGMGTSPEVHSIFLEGHTFLVRHHRQASLEISPLTFLTAQTF

DOGLESSI  295   LMDLGQFLLFCHIPSHQHDGMEAYVKVDSCPEEPQLRMKNN-ED-KDYDD
HUMLESSI  300   LMDLGQFLLFCHISSHQHDGMEAYVKVDSCPEEPQLRMKN-NEEAEDYDD
MULESSI   301   LIDLGQFLLFCHISSHKHDGMEAYVKVDSCPEESQWQKKNNNEEMEDYDD
PIGLESSI  301   LMDLGQFLLFCHISSHHHGGMEAHVRVESCAEEPQLRRKADEEE--DYDD

DOGLESSI  343   GLYDSDMDVVSFDDDSSSPFIQIRSVAKKHPKTWVHYIAAEEEDWDYAPS
HUMLESSI  349   DLTDSEMDVVRFDDDNSPSFIQIRSVAKKHPKTWVHYIAAEEEDWDYAPL
MULESSI   351   DLY-SEMDMFTLDYDS-SPFIQIRSVAKKYPKTWIHYISAEEEDWDYAPS
PIGLESSI  349   NLYDSDMDVVRLDGDDVSPFIQIRSVAKKHPKTWVHYISAEEEDWDYAPA
```

FIGURE 2A

```
DOGLESSI  393  GPTPNDRSHKNLYLNNGPQRIGKKYKKVRFVAYTDETFKTREAIQYESGI
HUMLESSI  399  VLAPDDRSYKSQYLNNGPQRIGRKYKKVRFMAYTDETFKTREAIQHESGI
 MULESSI  399  VPTSDNGSYKSQYLSNGPHRIGRKYKKVRFIAYTDETFKTRETIQHESGL
PIGLESSI  399  VPSPSDRSYKSLYLNSGPQRIGRKYKKARFVAYTDVTFKTRKAIPYESGI

DOGLESSI  443  LGPLLYGEVGDTLLIIFKNQASRPYNIYPHGINYVTPLHTGRLPKGVKHL
HUMLESSI  449  LGPLLYGEVGDTLLIIFKNQASRPYNIYPHGITDVRPLYSRRLPKGVKHL
 MULESSI  449  LGPLLYGEVGDTLLIIFKNQASRPYNIYPHGITDVSPLHARRLPRGIKHV
PIGLESSI  449  LGPLLYGEVGDTLLIIFKNKASRPYNIYPHGITDVSALHPGRLLKGWKHL

DOGLESSI  493  KDMPILPGEIFKYKWTVTVEDGPTKSDPRCLTRYYSSFINLERDLASGLI
HUMLESSI  499  KDFPILPGEIFKYKWTVTVEDGPTKSDPRCLTRYYSSFVNMERDLASGLI
 MULESSI  499  KDLPIHPGEIFKYKWTVTVEDGPTKSDPRCLTRYYSSFINPERDLASGLI
PIGLESSI  499  KDMPILPGETFKYKWTVTVEDGPTKSDPRCLTRYYSSSINLEKDLASGLI

DOGLESSI  543  GPLLICYKESVDQRGNQMMSDKRNVILFSVFDENRSWYLTENMQRFLPNA
HUMLESSI  549  GPLLICYKESVDQRGNQIMSDKRNVILFSVFDENRSWYLTENIQRFLPNP
 MULESSI  549  GPLLICYKESVDQRGNQMMSDKRNVILFSIFDENQSWYITENMQRFLPNA
PIGLESSI  549  GPLLICYKESVDQRGNQMMSDKRNVILFSVFDENQSWYLAENIQRFLPNP

DOGLESSI  593  DVVQPHDPEFQLSNIMHSINGYVFDNLQLSVCLHEVAYWYILSVGAQTDF
HUMLESSI  599  AGVQLEDPEFQASNIMHSINGYVFDSLQLSVCLHEVAYWYILSIGAQTDF
 MULESSI  599  AKTQPQDPGFQASNIMHSINGYVFDSLELTVCLHEVAYWHILSVGAQTDF
PIGLESSI  599  DGLQPQDPEFQASNIMHSINGYVFDSLQLSVCLHEVAYWYILSVGAQTDF

DOGLESSI  643  LSVFFSGYTFKHKMVYEDTLTLFPFSGETVFMSMENPGLWVLGCHNSDFR
HUMLESSI  649  LSVFFSGYTFKHKMVYEDTLTLFPFSGETVFMSMENPGLWILGCHNSDFR
 MULESSI  649  LSIFFSGYTFKHKMVYEDTLTLFPFSGETVFMSMENPGLWVLGCHNSDFR
PIGLESSI  649  LSVFFSGYTFKHKMVYEDTLTLFPFSGETVFMSMENPGLWVLGCHNSDLR

DOGLESSI  693  NRGMTALLKVSSCNRNIDDYYEDTYEDIPTPLLNENNVIKPRSFSQNSRH
HUMLESSI  699  NRGMTALLKVSSCDKNTGDYYEDSYEDISAYLLSKNNAIEPRSFSQNSRH
 MULESSI  699  KRGMTALLKVSSCDKSTSDYYEEIYEDIPTQLVNENNVIDPRSFFQNTNH
PIGLESSI  699  NRGMTALLKVYSCDRDIGDYYDNTYEDIPGFLLSGKNVIEPRSFAQNSRP

DOGLESSI  743  PSTKEKQLKATTTPENDIEKIDLQSGERTQLIKAQSVSSSDLLMLLGQN-
HUMLESSI  749  PSTRQKQFNATTIPENDIEKTDPWFAHRTPMPKIQNVSSSDLLMLL-RQS
 MULESSI  749  PNTRKKKFKDSTIPKNDMEKIEPQFEEIAEMLKVQSVSVSDMLMLLGQSH
PIGLESSI  749  PSASQKQFQTITSPEDDVE-LDPQSGERTQALEELSVPSGDGSMLLGQN-
```

FIGURE 2B

```
DOGLESSI   792  PTPRGLFLSDLREAT--DRADDHSRGAIERNKGPPEVASLRPELRHSEDR
HUMLESSI   798  PTPHGLSLSDLQEAKYETFSDDPSPGAIDSNNSLSEMTHFRPQLHHSGDM
 MULESSI   799  PTPHGLFLSDGQEAIYEAIHDDHSPNAIDSNEGPSKVTQLRPESHHSEKI
PIGLESSI   797  PAPHGSSSSDLQEARNE--ADDYLPGARERNTAPSAAARLRPELHHSAER

DOGLESSI   840  EFTPEPELQLRLNENLGTNTTVELKKLDLKISSSSDSLMTSPTIPSDKLA
HUMLESSI   848  VFTPESGLQLRLNEKLGTTAATELKKLDFKVSSTSNNLIS--TIPSDNLA
 MULESSI   849  VFTPQPGLQLRSNKSLETTIEVKWKKLGLQVSSLPSNLMTT-TILSDNLK
PIGLESSI   845  VLTPEPE--------------KELKKLDSKMSSSDLLKTSPTIPSDTLS

DOGLESSI   890  AATEKTGSLGPPNMSVHFNSHLGTIVFGNNSSHLIQSGVPLELSEEDNDS
HUMLESSI   896  AGTDNTSSLGPPSMPVHYDSQLDTTLFGKKSSPLTESGGPLSLSEENNDS
 MULESSI   898  ATFEKTDSSGFPDMPVHSSSKLSTTAFGKKAYSLVGSHVPLNASEENSDS
PIGLESSI   881  AETERTHSLGPPHPQVNFRSQLGAIVLGKNSSHFIGAGVPLGSTEEDHES

DOGLESSI   940  KLLEAPLMNIQESSLRENVLSMESNRLFKEERIRGPASLIKDNALFKVNI
HUMLESSI   946  KLLESGLMNSQESSWGKNVSSTESGRLFKGKRAHGPALLTKDNALFKVSI
 MULESSI   948  NILDSTLMYSQESLPRDNILSIENDRLLREKRFHGIALLTKDNTLFKDNV
PIGLESSI   931  SL------------GENVSPVESDGIFEKERAHGPASLTKDDVLFKVNI

DOGLESSI   990  SSVKTNRAPVNLTTNRKTRVAIPTLLIENSTSVWQDIMLERNTEFKEVTS
HUMLESSI   996  SLLKTNKTSNNSATNRKTHIDGPSLLIENSPSVWQNI-LESDTEFKKVTP
 MULESSI   998  SLMKTNKTYNHSTTNEKLHTESPTS-IENSTTDLQDAILKVNSEIQEVTA
PIGLESSI   968  SLVKTNKARVYLKTNRKIHIDDAALLTENRASA-----------------

DOGLESSI  1040  LIHNETFMDRNTTALGLNHVSNKTTLSKNVEMAHQKKEDPVPLRAENPDL
HUMLESSI  1045  LIHDRMLMDKNATALRLNHMSNKTTSSKNMEMVQQKKEGPIPPDAQNPDM
 MULESSI  1047  LIHDGTLLGKNSTYLRLNHMLNRTTSTKNKDIFHRKDEDPIPQDEENTIM
PIGLESSI  1001  -----TFMDKNTTASGLNHVSN----------------------------

DOGLESSI  1090  SSSKIPFLPD---WI-KTHGKNSLSSEQRPSPKQLTSLGSEKSVKDQNFL
HUMLESSI  1095  SFFKMLFLPESARWIQRTHGKNSLNSGQGPSPKQLVSLGPEKSVEGQNFL
 MULESSI  1097  PFSKMLFLSESSNWFKKTNGNNSLNSEQEHSPKQLVYLMFKKYVKNQSFL
PIGLESSI  1018  -------------WIKGPLGKNPLSSERGPSPELLTSSGSGKSVKGQSSG

DOGLESSI  1136  SE-EKVVVGEDEFTKDTELQE-IFPNNKSIFFANLANVQENDTYNQEKKS
HUMLESSI  1145  SEKNKVVVGKGEFTKDVGLKEMVFPSSRNLFLTNLDNLHENNTHNQEKKI
 MULESSI  1147  SEKNKVTVEQDGFTKNIGLKDMAFPHNMSIFLTTLSNVHENGRHNQEKNI
PIGLESSI  1055  QGRIRVAVEEEELSKG---KEMMLPNSELTFLTNSADVQGNDTHSQGKKS
```

FIGURE 2C

```
DOGLESSI 1184 PEEIERKEKLTQENVALPQAHTMIGTKNFLKNLFLLSTKQNVAGLEEQPY
HUMLESSI 1195 QEEIEKKETLIQENVVLPQIHTVTGTKNFMKNLFLLSTRQNVEGSYEGAY
 MULESSI 1197 QEEIE-KEALIEEKVVLPQVHEATGSKNFLKDILILGTRQNISLYE--VH
PIGLESSI 1102 REEMERREKLVQEKVDLPQVYTATGTKNFLRNIFHQSTEPSVEGFDGGSH

DOGLESSI 1234 TPILQDTRSLNDSPHSEGIHMANFSKIRE--EANLEGLGNQTNQMVERFP
HUMLESSI 1245 APVLQDFRSLNDSTNRTKKHTAHFSK--KGEEENLEGLGNQTKQIVEKYA
 MULESSI 1244 VPVLQNITSINNSTNTVQIHMEHFFKRRKDKETNSEGLVNKTREMVKNYP
PIGLESSI 1152 APVPQDSRSLNDSAERAETHIAHFSAIR--EEAPLEAPGNRT--------

DOGLESSI 1282 STTRMSSNASQH-VITQRGKRSLKQPRLSQGEIKFERKVIANDTSTQWSK
HUMLESSI 1293 CTTRISPNTSQQNFVTQRSKRALKQFRLPLEETELEKRIIVDDTSTQWSK
 MULESSI 1294 ---------SQKNITTQRSKRALGQFRLS---------------TQWLK
PIGLESSI 1192 -------GPGPRSAVPRRVKQSLKQIRLPLEEIKPERGVVLNATSTRWS-

DOGLESSI 1331 NMNYLAQGTLTQIEYNEKEKRAITQSPLSDCSMRNHVTIQMNDSALPVAK
HUMLESSI 1343 NMKHLTPSTLTQIDYNEKEKGAITQSPLSDCLTRSHSIPQANRSPLPIAK
 MULESSI 1319 TINCSTQCIIKQIDHSKEMKKFITKSSLSDSSV-IKSTTQTNSSDSHIVK
PIGLESSI 1234 --------------------------------------------------

DOGLESSI 1381 ESASPSVRHTDLTKIPSQHNSSHLPASACNYTFRERTSGVQEGSHFLQEA
HUMLESSI 1393 VSSFPSIRPIYLTRVLFQDNSSHLPAAS----YRKKDSGVQESSHFLQGA
 MULESSI 1368 TSAFPPI---DLKRSPFQNKFSHVQASSYIYDFKTKSSRIQESNNFLKET
PIGLESSI 1234 ------------------------------------------ESSPILQGA

DOGLESSI 1431 KRNNLSLAFVTLGITEGQGKFSSLGKSATNQPMYKKLENTVLLQPGLSET
HUMLESSI 1439 KKNNLSLAILTLEMTGDQREVGSLGTSATNSVTYKKVENTVLPKPDLPKT
 MULESSI 1415 KINNPSLAILPWNMFIDQGKFTSPGKSNTNSVTYKKRENIIFLKPTLPEE
PIGLESSI 1243 KRNNLSLPFLTLEMAGGQGKISALGKSAAGPLASGKLEKAVLSSAGLSEA

DOGLESSI 1481 SDKVELLSQVHVDQEDSFPTKTSNDSPGHLDLMGKIFLQKTQGPVKMNKT
HUMLESSI 1489 SGKVELLPKVHIYQKDLFPTETSNGSPGHLDLVEGSLLQGTEGAIKWNEA
 MULESSI 1465 SGKIELLPQVSIQEEEILPTETSHGSPGHLNLMKEVFLQKIQGPTKWNKA
PIGLESSI 1293 SGKAEFLPKVRVHREDLLPQKTSNVSCAHGDLGQEIFLQKTRGPVNLNKV

DOGLESSI 1531 NSPGKVPFLKWATESSEKIPSKLLGVLAWDNHYDTQIPSEEWKSQKKSQT
HUMLESSI 1539 NRPGKVPFLRVATESSAKTPSKLLDPLAWDNHYGTQIPKEEWKSQEKSPE
 MULESSI 1515 KRHGES--IKGKTESSKNTRSKLLNHHAWDYHYAAQIPKDMWKSKEKSPE
PIGLESSI 1343 NRPGR------------TPSKLLGP---------PMPKE-WESLEKSPK
```

FIGURE 2D

```
DOGLESSI 1581 NTAFKRKDTI-LPLGPCENNDSTAAINEGQDKPQREAMWAKQGEPGRLCS
HUMLESSI 1589 KTAFKKKDT-ILSLNACESNHAIAAINEGQNKPEIEVTWAKQGRTERLCS
 MULESSI 1563 IISIKQEDTI-LSLRPHGNSHSIGA-NEKQNWPQRETTWVKQGQTQRTCS
PIGLESSI 1370 STALRTKDIISLPLDRHESNHSIAAKNEGQAETQREAAWTKQGGPGRLCA

DOGLESSI 1630 QNPPVSKHHQREITVTTLQPEEDKFEYDDTFSIEMKREDFDIYGDYENQG
HUMLESSI 1638 QNPPVLKRHQREITRTTLQSDQEEIDYDDTISVEMKKEDFDIYDEDENQS
 MULESSI 1611 QIPPVLKRHQRELS--AFQSEQEATDYDDAITIETI-EDFDIYSEDIKQG
PIGLESSI 1420 PKPPVLRRHQRDISLPTFQPEEDKMDYDDIFSTETKGEDFDIYGEDENQD

DOGLESSI 1680 LRSFQKKTRHYFIAAVERLWDYGMSRSPHILRNRAQSGDVQQFKKVVFQE
HUMLESSI 1688 PRSFQKKTRHYFIAAVERLWDYGMSSSPHVLRNRAQSGSVPQFKKVVFQE
 MULESSI 1658 PRSFQQKTRHYFIAAVERLWDYGMS-TSHVLRNRYQSDNVPQFKKVVFQE
PIGLESSI 1470 PRSFQKRTRHYFIAAVEQLWDYGMSESPRALRNRAQNGEVPRFKKVVFRE

DOGLESSI 1730 FTDGSFTQPLYRGELNEHLGLLGPYIRAEVEDNIVVTFKNQASRPYSFYS
HUMLESSI 1738 FTDGSFTQPLYRGELNEHLGLLGPYIRAEVEDNIMVTFRNQASRPYSFYS
 MULESSI 1707 FTDGSFSQPLYRGELNEHLGLLGPYIRAEVEDNIMVTFKNQASRPYSFYS
PIGLESSI 1520 FADGSFTQPSYRGELNKHLGLLGPYIRAEVEDNIMVTFKNQASRPYSFYS

DOGLESSI 1780 SLISYDEDEGQGAEPRRKFVNPNETKIYFWKVQHHMAPTKDEFDCKAWAY
HUMLESSI 1788 SLISYEEDQRQGAEPRKNFVKPNETKTYFWKVQHHMAPTKDEFDCKAWAY
 MULESSI 1757 SLISYKEDQR-GEEPRRNFVKPNETKIYFWKVQHHMAPTEDEFDCKAWAY
PIGLESSI 1570 SLISYPDDQEQGAEPRHNFVQPNETRTYFWKVQHHMAPTEDEFDCKAWAY

DOGLESSI 1830 FSDVDLEKDVHSGLIGPLLICRSNTLNPAHGRQVTVQEFALVFTIFDETK
HUMLESSI 1838 FSDVDLEKDVHSGLIGPLLVCHTNTLNPAHGRQVTVQEFALFFTIFDETK
 MULESSI 1806 FSDVDLERDMHSGLIGPLLICHANTLNPAHGRQVSVQEFALLFTIFDETK
PIGLESSI 1620 FSDVDLEKDVHSGLIGPLLICRANTLNAAHGRQVTVQEFALFFTIFDETK

DOGLESSI 1880 SWYFTENLERNCRAPCNVQKEDPTLKENFRFHAINGYVKDTLPGLVMAQD
HUMLESSI 1888 SWYFTENMERNCRAPCNIQMEDPTFKENYRFHAINGYIMDTLPGLVMAQD
 MULESSI 1856 SWYFTENVKRNCKTPCNFQMEDPTLKENYRFHAINGYVMDTLPGLVMAQD
PIGLESSI 1670 SWYFTENVERNCRAPCHLQMEDPTLKENYRFHAINGYVMDTLPGLVMAQN

DOGLESSI 1930 QKVRWYLLSMGSNENIHSIHFSGHVFTVRKKEEYKMAVYNLYPGVFETVE
HUMLESSI 1938 QRIRWYLLSMGSNENIHSIHFSGHVFTVRKKEEYKMALYNLYPGVFETVE
 MULESSI 1906 QRIRWYLLSMGNNENIQSIHFSGHVFTVRKKEEYKMAVYNLYPGVFETLE
PIGLESSI 1720 QRIRWYLLSMGSNENIHSIHFSGHVFSVRKKEEYKMAVYNLYPGVFETVE
```

FIGURE 2E

```
DOGLESSI  1980  MLPSQVGIWRIECLIGEHLQAGMSTLFLVYSKKCQTPLGMASGHIRDFQI
HUMLESSI  1988  MLPSKAGIWRVECLIGEHLHAGMSTLFLVYSNKCQTPLGMASGHIRDFQI
 MULESSI  1956  MIPSRAGIWRVECLIGEHLQAGMSTLFLVYSKQCQIPLGMASGSIRDFQI
PIGLESSI  1770  MLPSKVGIWRIECLIGEHLQAGMSTTFLVYSKECQAPLGMASGRIRDFQI

DOGLESSI  2030  TASGQYGQWAPKLARLHYSGSINAWSTKDPFSWIKVDLLAPMIIHGIMTQ
HUMLESSI  2038  TASGQYGQWAPKLARLHYSGSINAWSTKEPFSWIKVDLLAPMIIHGIKTQ
 MULESSI  2006  TASGHYGQWAPNLARLHYSGSINAWSTKEPFSWIKVDLLAPMIVHGIKTQ
PIGLESSI  1820  TASGQYGQWAPKLARLHYSGSINAWSTKDPHSWIKVDLLAPMIIHGIMTQ

DOGLESSI  2080  GARQKFSSLYVSQFIIMYSLDGNKWHSYRGNSTGTLMVFFGNVDSSGIKH
HUMLESSI  2088  GARQKFSSLYISQFIIMYSLDGKKWQTYRGNSTGTLMVFFGNVDSSGIKH
 MULESSI  2056  GARQKFSSLYISQFIIMYSLDGKKWLSYQGNSTGTLMVFFGNVDSSGIKH
PIGLESSI  1870  GARQKFSSLYISQFIIMYSLDGRNWQSYRGNSTGTLMVFFGNVDASGIKH

DOGLESSI  2130  NIFNPPIIAQYIRLHPTHYSIRSTLRMELLGCDFNSCSMPLGMESKAISD
HUMLESSI  2138  NIFNPPIIARYIRLHPTHYSIRSTLRMELMGCDLNSCSMPLGMESKAISD
 MULESSI  2106  NSFNPPIIARYIRLHPTHSSIRSTLRMELMGCDLNSCSIPLGMESKVISD
PIGLESSI  1920  NIFNPPIVARYIRLHPTHYSIRSTLRMELMGCDLNSCSMPLGMQNKAISD

DOGLESSI  2180  AQITASSYLSSMLATWSPSQARLHLQGRTNAWRPQANNPKEWLQVDFRKT
HUMLESSI  2188  AQITASSYFTNMFATWSPSKARLHLQGRSNAWRPQVNNPKEWLQVDFQKT
 MULESSI  2156  TQITASSYFTNMFATWSPSQARLHLQGRTNAWRPQVNDPKQWLQVDLQKT
PIGLESSI  1970  SQITASSHLSNIFATWSPSQARLHLQGRTNAWRPRVSSAEEWLQVDLQKT

DOGLESSI  2230  MKVTGITTQGVKSLLISMYVKEFLISSSQDGHNWTLFLQNGKVKVFQGNR
HUMLESSI  2238  MKVTGVTTQGVKSLLTSMYVKEFLISSSQDGHQWTLFFQNGKVKVFQGNQ
 MULESSI  2206  MKVTGIITQGVKSLFTSMFVKEFLISSSQDGHHWTQILYNGKVKVFQGNQ
PIGLESSI  2020  VKVTGITTQGVKSLLSSMYVKEFLVSSSQDGRRWTLFLQDGHTKVFQGNQ

DOGLESSI  2280  DSSTPVRNRLEPPLVARYVRLHPQSWAHHIALRLEVLGCDTQQPA-
HUMLESSI  2288  DSFTPVVNSLDPPLLTRYLRIHPQSWVHQIALRMEVLGCEAQD-LY
 MULESSI  2256  DSSTPMMNSLDPPLLTRYLRIHPQIWEHQIALRLEILGCEAQQQY-
PIGLESSI  2070  DSSTPVVNALDPPLFTRYLRIHPTSWAQHIALRLEVLGCEAQDLY-
```

FIGURE 2F

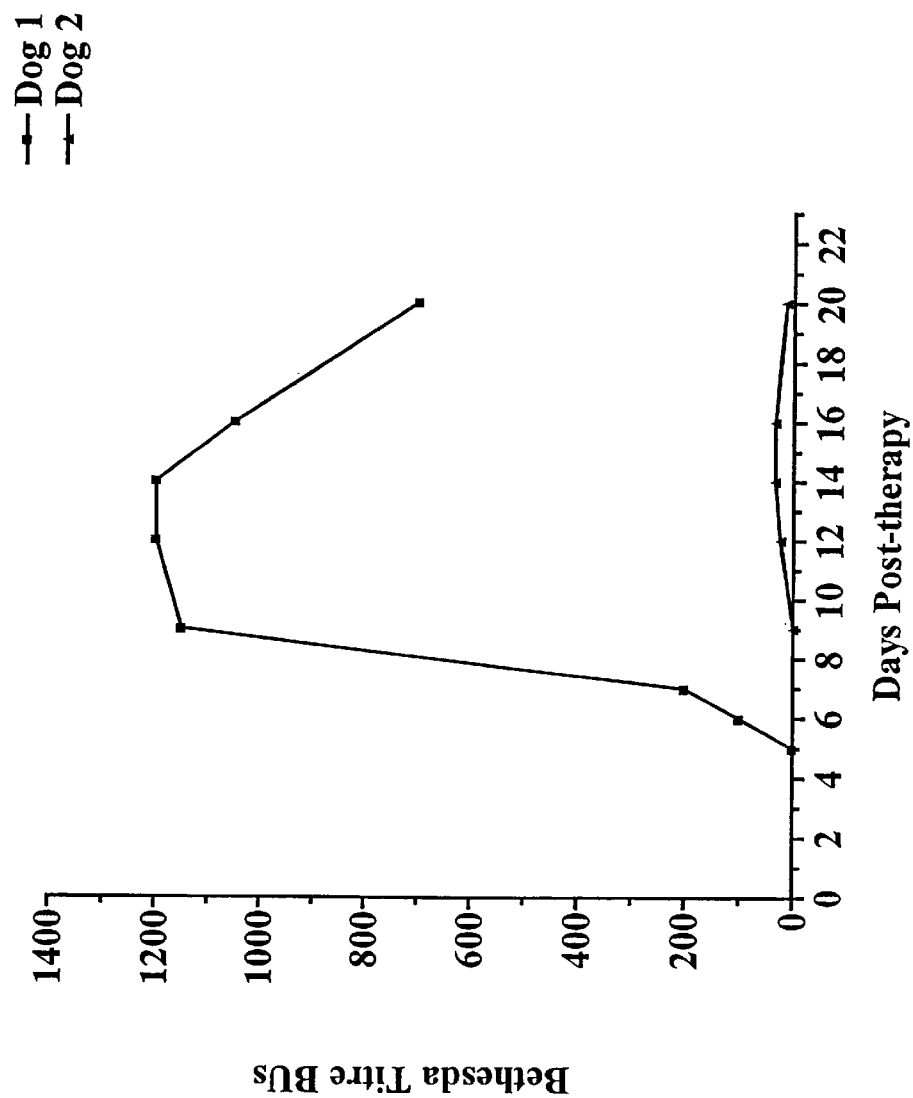

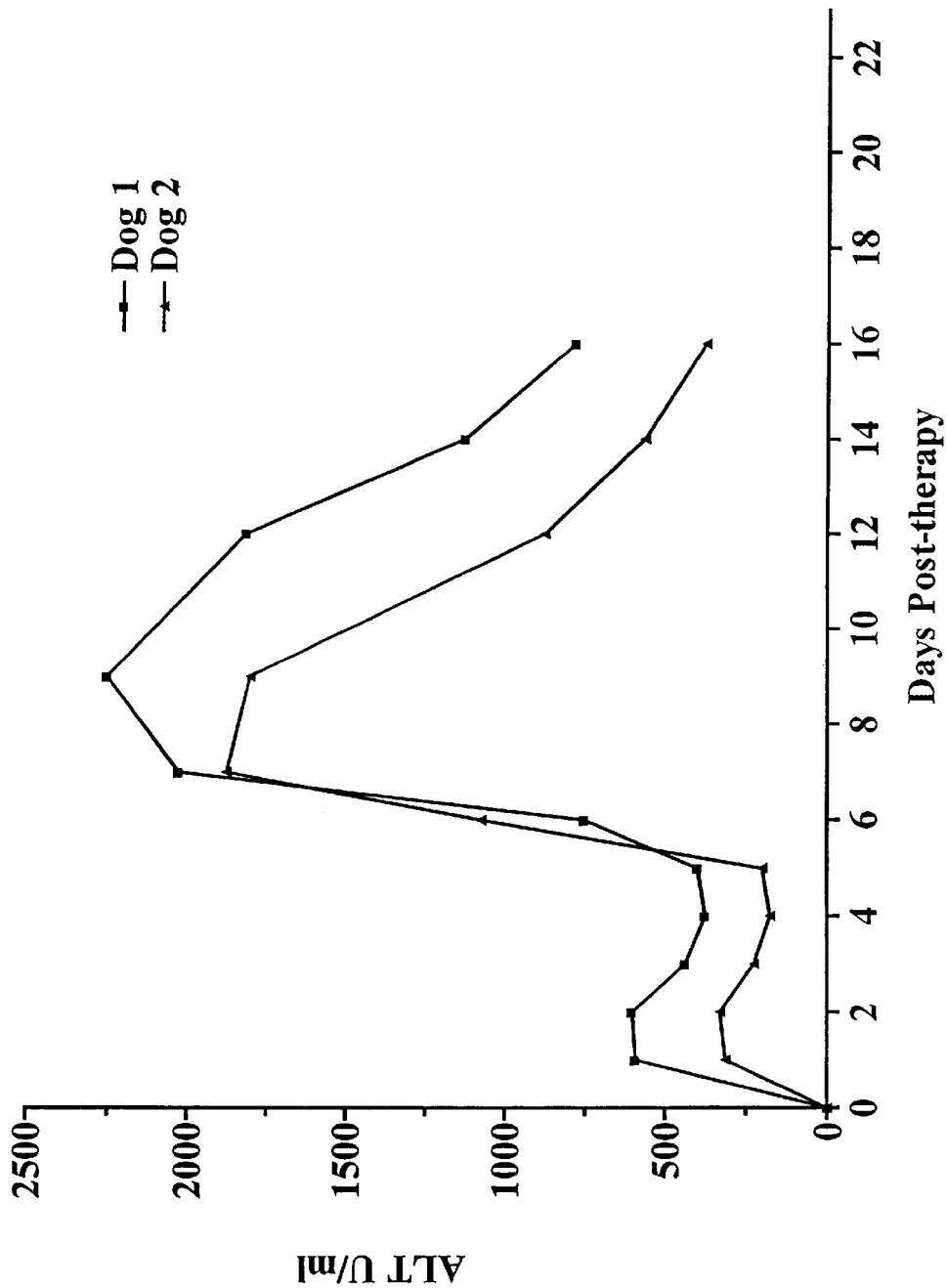

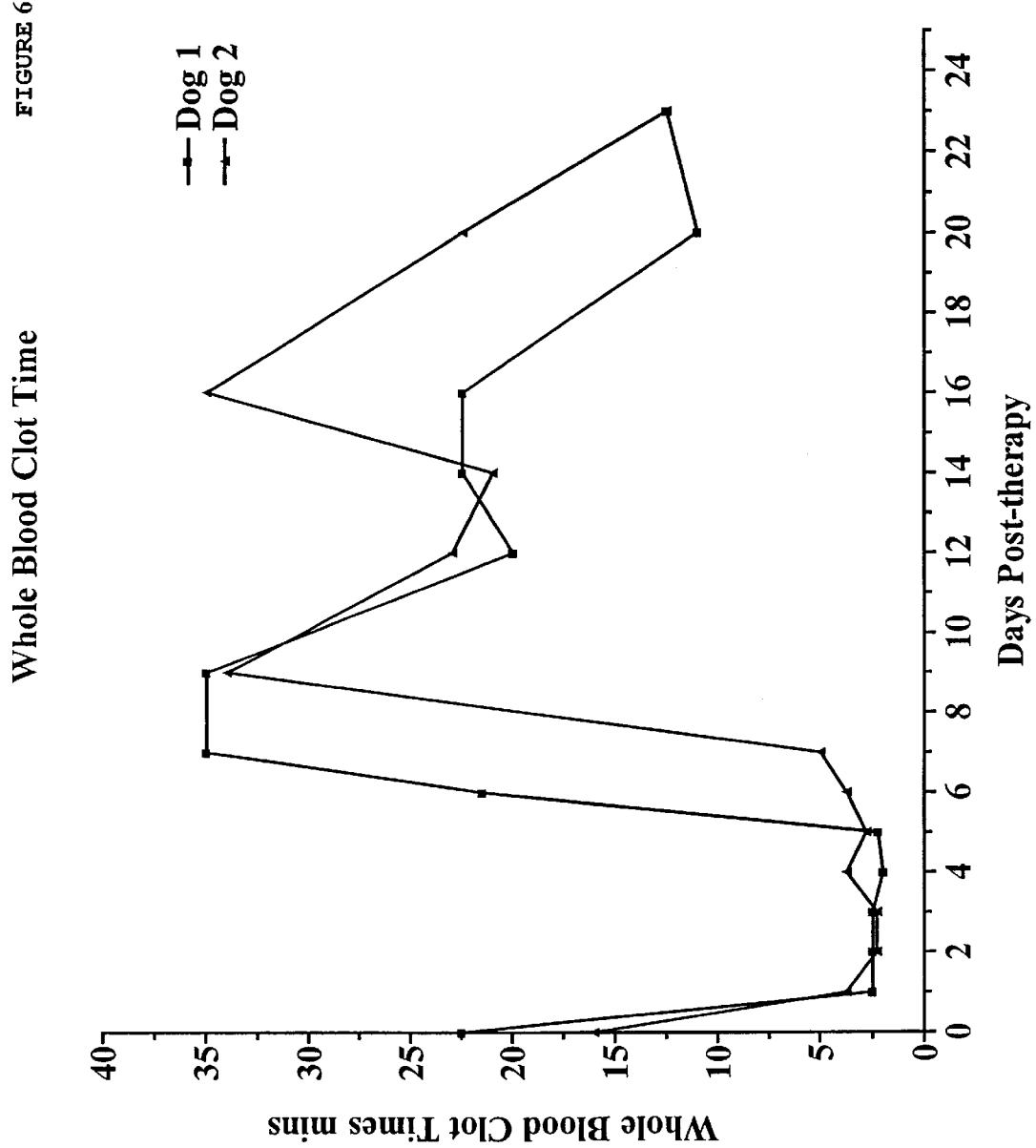

SEQUENCE LISTING

```
<160> NUMBER OF SEQ ID NOS: 63

<210> SEQ ID NO 1
<211> LENGTH: 7032
<212> TYPE: DNA
<213> ORGANISM: Canis familiaris
<220> FEATURE:
<221> NAME/KEY: CDS
<222> LOCATION: 1..7029

<400> SEQUENCE: 1 atg caa gta gag ctc tac acc tgc tgc ttt ctg tgc ctt ttg ccc ttc        48
Met Gln Val Glu Leu Tyr Thr Cys Cys Phe Leu Cys Leu Leu Pro Phe
```

-continued

| | 1 | | | | 5 | | | | 10 | | | | 15 | | | |
|---|---|---|---|---|---|---|---|---|---|---|---|---|---|---|---|---|
| agc | ctt | agt | gcc | acc | aga | aaa | tac | tac | ctc | ggt | gca | gtg | gaa | ctg | tcc | 96 |
| Ser | Leu | Ser | Ala | Thr | Arg | Lys | Tyr | Tyr | Leu | Gly | Ala | Val | Glu | Leu | Ser | |
| | | | | 20 | | | | | 25 | | | | | 30 | | |
| tgg | gac | tat | atg | caa | agt | gac | ctg | ctc | agt | gcg | ctg | cac | gcg | gac | aca | 144 |
| Trp | Asp | Tyr | Met | Gln | Ser | Asp | Leu | Leu | Ser | Ala | Leu | His | Ala | Asp | Thr | |
| | | 35 | | | | | 40 | | | | | 45 | | | | |
| agc | ttt | tct | tcc | agg | gtg | cca | gga | tct | ttg | cca | ctc | acc | acg | tca | gtc | 192 |
| Ser | Phe | Ser | Ser | Arg | Val | Pro | Gly | Ser | Leu | Pro | Leu | Thr | Thr | Ser | Val | |
| | 50 | | | | | 55 | | | | | 60 | | | | | |
| acg | tac | aga | aag | act | gtg | ttt | gta | gag | ttt | aca | gat | gac | ctt | ttc | aac | 240 |
| Thr | Tyr | Arg | Lys | Thr | Val | Phe | Val | Glu | Phe | Thr | Asp | Asp | Leu | Phe | Asn | |
| 65 | | | | | 70 | | | | | 75 | | | | | 80 | |
| att | gcc | aag | ccc | agg | cca | ccg | tgg | atg | ggc | ctg | ctg | ggt | cct | acc | atc | 288 |
| Ile | Ala | Lys | Pro | Arg | Pro | Pro | Trp | Met | Gly | Leu | Leu | Gly | Pro | Thr | Ile | |
| | | | | 85 | | | | | 90 | | | | | 95 | | |
| cag | gct | gag | gtt | tat | gac | aca | gtg | gtc | att | gtc | ctt | aag | aac | atg | gct | 336 |
| Gln | Ala | Glu | Val | Tyr | Asp | Thr | Val | Val | Ile | Val | Leu | Lys | Asn | Met | Ala | |
| | | | 100 | | | | | 105 | | | | | 110 | | | |
| tct | cat | cct | gtc | agc | ctt | cac | gct | gtt | ggt | gta | tcc | tat | tgg | aaa | gct | 384 |
| Ser | His | Pro | Val | Ser | Leu | His | Ala | Val | Gly | Val | Ser | Tyr | Trp | Lys | Ala | |
| | | 115 | | | | | 120 | | | | | 125 | | | | |
| tct | gaa | ggt | gct | gag | tat | gag | gat | cag | acc | agc | caa | aag | gag | aag | gaa | 432 |
| Ser | Glu | Gly | Ala | Glu | Tyr | Glu | Asp | Gln | Thr | Ser | Gln | Lys | Glu | Lys | Glu | |
| | 130 | | | | | 135 | | | | | 140 | | | | | |
| gat | gat | aat | gtc | att | cct | ggt | gaa | agc | cat | acc | tat | gtc | tgg | cag | gtc | 480 |
| Asp | Asp | Asn | Val | Ile | Pro | Gly | Glu | Ser | His | Thr | Tyr | Val | Trp | Gln | Val | |
| 145 | | | | | 150 | | | | | 155 | | | | | 160 | |
| ctg | aaa | gag | aat | ggc | cca | atg | gcc | tct | gat | cca | cca | tgt | ctc | acc | tac | 528 |
| Leu | Lys | Glu | Asn | Gly | Pro | Met | Ala | Ser | Asp | Pro | Pro | Cys | Leu | Thr | Tyr | |
| | | | | 165 | | | | | 170 | | | | | 175 | | |
| tca | tat | ttt | tca | cac | gtg | gac | ctg | gtg | aaa | gac | ctg | aat | tca | ggc | ctc | 576 |
| Ser | Tyr | Phe | Ser | His | Val | Asp | Leu | Val | Lys | Asp | Leu | Asn | Ser | Gly | Leu | |
| | | | 180 | | | | | 185 | | | | | 190 | | | |
| att | gga | gcc | ctg | ctg | gtt | tgc | aaa | gaa | ggg | agt | ctg | gcc | aaa | gaa | agg | 624 |
| Ile | Gly | Ala | Leu | Leu | Val | Cys | Lys | Glu | Gly | Ser | Leu | Ala | Lys | Glu | Arg | |
| | | 195 | | | | | 200 | | | | | 205 | | | | |
| aca | cag | acc | ttg | cag | gaa | ttt | gtc | cta | ctt | ttt | gct | gta | ttt | gat | gaa | 672 |
| Thr | Gln | Thr | Leu | Gln | Glu | Phe | Val | Leu | Leu | Phe | Ala | Val | Phe | Asp | Glu | |
| | 210 | | | | | 215 | | | | | 220 | | | | | |
| ggg | aaa | agt | tgg | cac | tca | gaa | aca | aat | gcg | tct | ttg | aca | cag | gct | gag | 720 |
| Gly | Lys | Ser | Trp | His | Ser | Glu | Thr | Asn | Ala | Ser | Leu | Thr | Gln | Ala | Glu | |
| 225 | | | | | 230 | | | | | 235 | | | | | 240 | |
| gcc | cag | cat | gag | ctg | cac | acc | atc | aat | ggc | tat | gta | aac | agg | tct | ctg | 768 |
| Ala | Gln | His | Glu | Leu | His | Thr | Ile | Asn | Gly | Tyr | Val | Asn | Arg | Ser | Leu | |
| | | | | 245 | | | | | 250 | | | | | 255 | | |
| cca | ggt | ctt | act | gtg | tgt | cac | aag | aga | tca | gtc | tat | tgg | cat | gtg | att | 816 |
| Pro | Gly | Leu | Thr | Val | Cys | His | Lys | Arg | Ser | Val | Tyr | Trp | His | Val | Ile | |
| | | | 260 | | | | | 265 | | | | | 270 | | | |
| gga | atg | ggc | acc | acc | ccc | gaa | gtg | cac | tca | att | ttt | ctc | gaa | ggt | cac | 864 |
| Gly | Met | Gly | Thr | Thr | Pro | Glu | Val | His | Ser | Ile | Phe | Leu | Glu | Gly | His | |
| | | 275 | | | | | 280 | | | | | 285 | | | | |
| aca | ttt | ctt | gtg | agg | aac | cac | cgc | cag | gcc | tcc | ttg | gag | atc | tca | cca | 912 |
| Thr | Phe | Leu | Val | Arg | Asn | His | Arg | Gln | Ala | Ser | Leu | Glu | Ile | Ser | Pro | |
| | 290 | | | | | 295 | | | | | 300 | | | | | |
| att | act | ttc | ctt | act | gct | cag | aca | ttc | ctg | atg | gac | ctt | ggc | cag | ttt | 960 |
| Ile | Thr | Phe | Leu | Thr | Ala | Gln | Thr | Phe | Leu | Met | Asp | Leu | Gly | Gln | Phe | |
| 305 | | | | | 310 | | | | | 315 | | | | | 320 | |
| cta | ctg | ttt | tgt | cat | atc | cct | tcc | cat | caa | cat | gat | ggt | atg | gaa | gct | 1008 |

```
Leu Leu Phe Cys His Ile Pro Ser His Gln His Asp Gly Met Glu Ala
            325                 330                 335 tat gtc aaa gta gat agc tgc cca gag gaa ccc cag ctg cgc atg aaa    1056
Tyr Val Lys Val Asp Ser Cys Pro Glu Glu Pro Gln Leu Arg Met Lys
            340                 345                 350 aat aat gaa gat aaa gat tat gat gat ggt ctt tat gat tct gac atg    1104
Asn Asn Glu Asp Lys Asp Tyr Asp Asp Gly Leu Tyr Asp Ser Asp Met
            355                 360                 365 gac gta gtt agc ttt gat gac gac agc tct tct ccc ttt atc caa atc    1152
Asp Val Val Ser Phe Asp Asp Asp Ser Ser Ser Pro Phe Ile Gln Ile
            370                 375                 380 cgc tca gtt gcc aag aag cat cct aaa act tgg gtc cac tat att gct    1200
Arg Ser Val Ala Lys Lys His Pro Lys Thr Trp Val His Tyr Ile Ala
385                 390                 395                 400 gct gag gag gag gac tgg gac tat gct ccc tca ggc ccc acc ccc aat    1248
Ala Glu Glu Glu Asp Trp Asp Tyr Ala Pro Ser Gly Pro Thr Pro Asn
                405                 410                 415 gat aga agt cat aaa aat ctg tat ttg aac aat ggt cct cag cgg att    1296
Asp Arg Ser His Lys Asn Leu Tyr Leu Asn Asn Gly Pro Gln Arg Ile
            420                 425                 430 ggt aag aag tac aaa aaa gtc cga ttt gtg gca tac aca gat gag aca    1344
Gly Lys Lys Tyr Lys Lys Val Arg Phe Val Ala Tyr Thr Asp Glu Thr
            435                 440                 445 ttt aag act cgt gaa gct att cag tat gaa tca gga atc ctg gga cct    1392
Phe Lys Thr Arg Glu Ala Ile Gln Tyr Glu Ser Gly Ile Leu Gly Pro
            450                 455                 460 tta ctt tat gga gaa gtt gga gac aca ctg ctg att ata ttt aag aat    1440
Leu Leu Tyr Gly Glu Val Gly Asp Thr Leu Leu Ile Ile Phe Lys Asn
465                 470                 475                 480 caa gcc agc cgg cca tat aac atc tac cct cat ggg atc aat tat gtc    1488
Gln Ala Ser Arg Pro Tyr Asn Ile Tyr Pro His Gly Ile Asn Tyr Val
                485                 490                 495 act cct ctg cac aca ggg aga ttg cca aaa ggt gtg aaa cat ttg aaa    1536
Thr Pro Leu His Thr Gly Arg Leu Pro Lys Gly Val Lys His Leu Lys
            500                 505                 510 gat atg cca att ctg ccg gga gag ata ttc aag tat aaa tgg aca gtg    1584
Asp Met Pro Ile Leu Pro Gly Glu Ile Phe Lys Tyr Lys Trp Thr Val
            515                 520                 525 acc gta gaa gat gga cca act aaa tca gat cct cgg tgc ctg acc cga    1632
Thr Val Glu Asp Gly Pro Thr Lys Ser Asp Pro Arg Cys Leu Thr Arg
            530                 535                 540 tat tac tca agc ttc att aat ctg gag aga gat cta gct tca gga ctc    1680
Tyr Tyr Ser Ser Phe Ile Asn Leu Glu Arg Asp Leu Ala Ser Gly Leu
545                 550                 555                 560 att ggc cct ctt ctc atc tgc tac aaa gaa tct gta gat caa aga gga    1728
Ile Gly Pro Leu Leu Ile Cys Tyr Lys Glu Ser Val Asp Gln Arg Gly
                565                 570                 575 aac cag atg atg tca gac aag aga aat gtc atc ctg ttt tct gta ttt    1776
Asn Gln Met Met Ser Asp Lys Arg Asn Val Ile Leu Phe Ser Val Phe
            580                 585                 590 gat gag aat cga agc tgg tac ctc aca gag aat atg cag cgc ttc ctc    1824
Asp Glu Asn Arg Ser Trp Tyr Leu Thr Glu Asn Met Gln Arg Phe Leu
            595                 600                 605 ccc aat gca gat gta gtg cag ccc cat gac cca gag ttc caa ctc tct    1872
Pro Asn Ala Asp Val Val Gln Pro His Asp Pro Glu Phe Gln Leu Ser
            610                 615                 620 aac atc atg cac agc atc aat ggc tat gtt ttt gac aac ttg cag ctg    1920
Asn Ile Met His Ser Ile Asn Gly Tyr Val Phe Asp Asn Leu Gln Leu
625                 630                 635                 640
```

```
tca gtt tgt ttg cat gag gtg gcg tac tgg tac att cta agt gtt gga    1968
Ser Val Cys Leu His Glu Val Ala Tyr Trp Tyr Ile Leu Ser Val Gly
                645                 650                 655 gca caa act gac ttc ctg tct gtc ttc ttc tct gga tat acc ttc aaa    2016
Ala Gln Thr Asp Phe Leu Ser Val Phe Phe Ser Gly Tyr Thr Phe Lys
            660                 665                 670 cac aaa atg gtc tat gaa gac aca ctt acc ctc ttc cca ttc tca gga    2064
His Lys Met Val Tyr Glu Asp Thr Leu Thr Leu Phe Pro Phe Ser Gly
        675                 680                 685 gaa act gtc ttc atg tca atg gaa aac cca ggt ctg tgg gtt ctg ggg    2112
Glu Thr Val Phe Met Ser Met Glu Asn Pro Gly Leu Trp Val Leu Gly
    690                 695                 700 tgc cac aac tca gac ttt cgg aac aga ggc atg aca gcc tta ctg aag    2160
Cys His Asn Ser Asp Phe Arg Asn Arg Gly Met Thr Ala Leu Leu Lys
705                 710                 715                 720 gtt tct agt tgt aac agg aac att gat gat tat tat gag gac aca tac    2208
Val Ser Ser Cys Asn Arg Asn Ile Asp Asp Tyr Tyr Glu Asp Thr Tyr
                725                 730                 735 gaa gat att cca act ccc ctg cta aat gaa aac aat gta att aaa cct    2256
Glu Asp Ile Pro Thr Pro Leu Leu Asn Glu Asn Asn Val Ile Lys Pro
            740                 745                 750 aga agc ttc tcc cag aat tca agg cac cct agc act aag gaa aag caa    2304
Arg Ser Phe Ser Gln Asn Ser Arg His Pro Ser Thr Lys Glu Lys Gln
        755                 760                 765 ttg aaa gcc acc aca act cca gaa aat gac ata gag aag att gac ctt    2352
Leu Lys Ala Thr Thr Thr Pro Glu Asn Asp Ile Glu Lys Ile Asp Leu
    770                 775                 780 caa tct gga gaa aga aca cag ctg att aaa gca caa agt gtc tcc tct    2400
Gln Ser Gly Glu Arg Thr Gln Leu Ile Lys Ala Gln Ser Val Ser Ser
785                 790                 795                 800 agt gat ttg ttg atg ctg ttg gga cag aat cct act cca cgt gga ctg    2448
Ser Asp Leu Leu Met Leu Leu Gly Gln Asn Pro Thr Pro Arg Gly Leu
                805                 810                 815 ttc tta tct gat ctc cga gag gcc aca gat aga gcc gat gac cat tca    2496
Phe Leu Ser Asp Leu Arg Glu Ala Thr Asp Arg Ala Asp Asp His Ser
            820                 825                 830 cgt gga gca ata gaa aga aac aag ggc cca cct gaa gtg gca agt ctc    2544
Arg Gly Ala Ile Glu Arg Asn Lys Gly Pro Pro Glu Val Ala Ser Leu
        835                 840                 845 aga cca gag ctc cgt cac agt gag gac aga gaa ttt act cct gag cca    2592
Arg Pro Glu Leu Arg His Ser Glu Asp Arg Glu Phe Thr Pro Glu Pro
    850                 855                 860 gaa ctg cag tta aga tta aat gag aat ttg ggg aca aat aca aca gta    2640
Glu Leu Gln Leu Arg Leu Asn Glu Asn Leu Gly Thr Asn Thr Thr Val
865                 870                 875                 880 gag ttg aag aaa ctt gat tta aaa att tct agt tca tca gac agt cta    2688
Glu Leu Lys Lys Leu Asp Leu Lys Ile Ser Ser Ser Ser Asp Ser Leu
                885                 890                 895 atg act tca cca aca att cca tca gat aag ttg gca gca gct act gaa    2736
Met Thr Ser Pro Thr Ile Pro Ser Asp Lys Leu Ala Ala Ala Thr Glu
            900                 905                 910 aag aca ggt tcc tta gga ccc cca aat atg tca gtt cac ttt aac agt    2784
Lys Thr Gly Ser Leu Gly Pro Pro Asn Met Ser Val His Phe Asn Ser
        915                 920                 925 cat tta ggt acc att gta ttt ggc aat aat tca tcc cac ctt att cag    2832
His Leu Gly Thr Ile Val Phe Gly Asn Asn Ser Ser His Leu Ile Gln
    930                 935                 940 tct ggt gta cct ttg gaa ttg agt gaa gaa gat aat gat tcc aag ttg    2880
Ser Gly Val Pro Leu Glu Leu Ser Glu Glu Asp Asn Asp Ser Lys Leu
945                 950                 955                 960
```

-continued

```
tta gaa gca cct tta atg aat att caa gaa agt tca ctg aga gaa aat        2928
Leu Glu Ala Pro Leu Met Asn Ile Gln Glu Ser Ser Leu Arg Glu Asn
            965                 970                 975 gta tta tca atg gag agt aat agg tta ttt aaa gaa gaa aga att cgt        2976
Val Leu Ser Met Glu Ser Asn Arg Leu Phe Lys Glu Glu Arg Ile Arg
        980                 985                 990 gga cct gct tca tta atc aaa gat aat gct tta ttc aaa gtt aat atc        3024
Gly Pro Ala Ser Leu Ile Lys Asp Asn Ala Leu Phe Lys Val Asn Ile
    995                1000                1005 tct tcg gta aag aca aac agg gca cca gtt aac tta aca act aat aga        3072
Ser Ser Val Lys Thr Asn Arg Ala Pro Val Asn Leu Thr Thr Asn Arg
1010                1015                1020 aag act cgt gtt gct atc cca aca tta tta att gag aac agt acc tca        3120
Lys Thr Arg Val Ala Ile Pro Thr Leu Leu Ile Glu Asn Ser Thr Ser
1025                1030                1035                1040 gtc tgg caa gat att atg tta gaa agg aat act gag ttt aaa gaa gta        3168
Val Trp Gln Asp Ile Met Leu Glu Arg Asn Thr Glu Phe Lys Glu Val
            1045                1050                1055 act tct ttg att cat aat gaa acg ttt atg gac aga aat act aca gct        3216
Thr Ser Leu Ile His Asn Glu Thr Phe Met Asp Arg Asn Thr Thr Ala
        1060                1065                1070 ctg ggg cta aat cat gtg tca aat aaa act act tta tca aaa aat gtg        3264
Leu Gly Leu Asn His Val Ser Asn Lys Thr Thr Leu Ser Lys Asn Val
    1075                1080                1085 gaa atg gcc cac caa aaa aaa gaa gac cct gtg cca cta cgt gca gaa        3312
Glu Met Ala His Gln Lys Lys Glu Asp Pro Val Pro Leu Arg Ala Glu
1090                1095                1100 aat cca gat cta tca tcc tcc aag ata ccg ttc ttg cca gat tgg ata        3360
Asn Pro Asp Leu Ser Ser Ser Lys Ile Pro Phe Leu Pro Asp Trp Ile
1105                1110                1115                1120 aag acc cat ggc aag aac tcc cta agc tct gag caa agg ccc agt cca        3408
Lys Thr His Gly Lys Asn Ser Leu Ser Ser Glu Gln Arg Pro Ser Pro
            1125                1130                1135 aaa caa tta aca tct tta gga tca gaa aaa tct gtg aaa gat cag aac        3456
Lys Gln Leu Thr Ser Leu Gly Ser Glu Lys Ser Val Lys Asp Gln Asn
        1140                1145                1150 ttt ttg tca gag gag aag gtg gta gta gga gag gat gaa ttt acg aag        3504
Phe Leu Ser Glu Glu Lys Val Val Val Gly Glu Asp Glu Phe Thr Lys
    1155                1160                1165 gac aca gaa ctc caa gag att ttt cca aac aac aag agc ata ttt ttt        3552
Asp Thr Glu Leu Gln Glu Ile Phe Pro Asn Asn Lys Ser Ile Phe Phe
1170                1175                1180 gct aac ttg gct aat gtc caa gaa aat gat aca tac aat caa gaa aaa        3600
Ala Asn Leu Ala Asn Val Gln Glu Asn Asp Thr Tyr Asn Gln Glu Lys
1185                1190                1195                1200 aaa tct ccg gaa gag ata gaa aga aag gaa aaa tta acc cag gag aat        3648
Lys Ser Pro Glu Glu Ile Glu Arg Lys Glu Lys Leu Thr Gln Glu Asn
            1205                1210                1215 gtg gct ttg cct cag gca cat act atg att ggc act aag aac ttc ctg        3696
Val Ala Leu Pro Gln Ala His Thr Met Ile Gly Thr Lys Asn Phe Leu
        1220                1225                1230 aag aac ctt ttc tta cta agc act aag caa aat gta gca ggt tta gaa        3744
Lys Asn Leu Phe Leu Leu Ser Thr Lys Gln Asn Val Ala Gly Leu Glu
    1235                1240                1245 gag cag cca tat act cca ata ctt caa gac acc agg tca tta aat gat        3792
Glu Gln Pro Tyr Thr Pro Ile Leu Gln Asp Thr Arg Ser Leu Asn Asp
1250                1255                1260 tcg cca cat agt gaa ggg att cat atg gcc aat ttc tca aaa ata agg        3840
Ser Pro His Ser Glu Gly Ile His Met Ala Asn Phe Ser Lys Ile Arg
```

```
1265                1270                1275                1280 gaa gaa gca aac ttg gaa ggc ttg gga aat caa aca aac caa atg gta      3888
Glu Glu Ala Asn Leu Glu Gly Leu Gly Asn Gln Thr Asn Gln Met Val
                1285                1290                1295 gag agg ttt cca agc act acg agg atg tct tct aat gca agt cag cat      3936
Glu Arg Phe Pro Ser Thr Thr Arg Met Ser Ser Asn Ala Ser Gln His
        1300                1305                1310 gtt atc act caa cgt ggt aag cgg agt ttg aaa caa ccc aga ctc tca      3984
Val Ile Thr Gln Arg Gly Lys Arg Ser Leu Lys Gln Pro Arg Leu Ser
        1315                1320                1325 caa gga gaa ata aag ttt gaa agg aag gtt att gca aat gac act tca      4032
Gln Gly Glu Ile Lys Phe Glu Arg Lys Val Ile Ala Asn Asp Thr Ser
        1330                1335                1340 acc cag tgg tcc aaa aac atg aac tat ttg gcc cag gga acc ctc aca      4080
Thr Gln Trp Ser Lys Asn Met Asn Tyr Leu Ala Gln Gly Thr Leu Thr
1345                1350                1355                1360 cag ata gag tat aat gag aaa gaa aaa agg gcc att act cag tcc ccc      4128
Gln Ile Glu Tyr Asn Glu Lys Glu Lys Arg Ala Ile Thr Gln Ser Pro
                1365                1370                1375 cta tca gat tgt tct atg agg aat cat gtc acc att caa atg aat gac      4176
Leu Ser Asp Cys Ser Met Arg Asn His Val Thr Ile Gln Met Asn Asp
        1380                1385                1390 tct gca tta ccc gtt gca aag gaa tca gca tct cca tca gtt aga cat      4224
Ser Ala Leu Pro Val Ala Lys Glu Ser Ala Ser Pro Ser Val Arg His
        1395                1400                1405 aca gat ctg acc aag atc cca tcc caa cac aac tct tct cat ctt cca      4272
Thr Asp Leu Thr Lys Ile Pro Ser Gln His Asn Ser Ser His Leu Pro
        1410                1415                1420 gca tca gcc tgt aat tat acc ttt aga gag agg act tct gga gtc caa      4320
Ala Ser Ala Cys Asn Tyr Thr Phe Arg Glu Arg Thr Ser Gly Val Gln
1425                1430                1435                1440 gaa ggc agt cat ttc tta caa gaa gcc aaa aga aat aac ctc tct tta      4368
Glu Gly Ser His Phe Leu Gln Glu Ala Lys Arg Asn Asn Leu Ser Leu
                1445                1450                1455 gcc ttt gta acc tta gga ata act gaa ggg caa gga aag ttc agc tcc      4416
Ala Phe Val Thr Leu Gly Ile Thr Glu Gly Gln Gly Lys Phe Ser Ser
        1460                1465                1470 ctg ggg aaa agt gcc aca aac caa ccc atg tac aag aaa ctt gaa aac      4464
Leu Gly Lys Ser Ala Thr Asn Gln Pro Met Tyr Lys Lys Leu Glu Asn
        1475                1480                1485 act gtt ctc ttg caa cca ggc ttg tcc gaa aca tct gac aaa gtt gaa      4512
Thr Val Leu Leu Gln Pro Gly Leu Ser Glu Thr Ser Asp Lys Val Glu
        1490                1495                1500 tta ctt tct caa gtt cat gtt gat caa gaa gac tct ttc cct aca aaa      4560
Leu Leu Ser Gln Val His Val Asp Gln Glu Asp Ser Phe Pro Thr Lys
1505                1510                1515                1520 act agc aat gat tct cct ggc cac ctg gat ctc atg gga aag atc ttc      4608
Thr Ser Asn Asp Ser Pro Gly His Leu Asp Leu Met Gly Lys Ile Phe
                1525                1530                1535 ctt cag aaa aca cag gga cct gtt aaa atg aat aaa aca aat agc cct      4656
Leu Gln Lys Thr Gln Gly Pro Val Lys Met Asn Lys Thr Asn Ser Pro
        1540                1545                1550 gga aaa gtg ccc ttt ctg aaa tgg gca aca gaa agc tct gaa aag att      4704
Gly Lys Val Pro Phe Leu Lys Trp Ala Thr Glu Ser Ser Glu Lys Ile
        1555                1560                1565 ccc tcc aag ctg ctg ggt gtc ctt gct tgg gat aac cac tat gat acc      4752
Pro Ser Lys Leu Leu Gly Val Leu Ala Trp Asp Asn His Tyr Asp Thr
        1570                1575                1580 cag ata cca agt gaa gag tgg aaa tcc caa aaa aag tca cag acg aac      4800
```

-continued

```
Gln Ile Pro Ser Glu Glu Trp Lys Ser Gln Lys Lys Ser Gln Thr Asn
1585                1590                1595                1600 aca gct ttt aaa agg aaa gac acc att ttg ccc ctg ggc cct tgt gaa     4848
Thr Ala Phe Lys Arg Lys Asp Thr Ile Leu Pro Leu Gly Pro Cys Glu
            1605                1610                1615 aat aat gat tca aca gca gca ata aat gaa gga caa gat aag ccc caa     4896
Asn Asn Asp Ser Thr Ala Ala Ile Asn Glu Gly Gln Asp Lys Pro Gln
        1620                1625                1630 aga gaa gct atg tgg gca aag caa gga gag cct gga agg ttg tgc tct     4944
Arg Glu Ala Met Trp Ala Lys Gln Gly Glu Pro Gly Arg Leu Cys Ser
    1635                1640                1645 caa aac cca cca gtc tca aaa cac cat caa agg gaa ata acc gtt act     4992
Gln Asn Pro Pro Val Ser Lys His His Gln Arg Glu Ile Thr Val Thr
1650                1655                1660 act ctt cag cca gag gaa gac aaa ttt gag tat gat gac acc ttc tca     5040
Thr Leu Gln Pro Glu Glu Asp Lys Phe Glu Tyr Asp Asp Thr Phe Ser
1665                1670                1675                1680 att gaa atg aag aga gaa gat ttt gac atc tac ggc gac tat gaa aat     5088
Ile Glu Met Lys Arg Glu Asp Phe Asp Ile Tyr Gly Asp Tyr Glu Asn
            1685                1690                1695 cag ggc ctc cgc agc ttt caa aag aaa aca cga cac tat ttc att gct     5136
Gln Gly Leu Arg Ser Phe Gln Lys Lys Thr Arg His Tyr Phe Ile Ala
        1700                1705                1710 gca gtg gag cgt ctc tgg gat tat ggg atg agt aga tct ccc cat ata     5184
Ala Val Glu Arg Leu Trp Asp Tyr Gly Met Ser Arg Ser Pro His Ile
    1715                1720                1725 cta aga aac agg gct caa agt ggg gat gtc cag cag ttc aag aag gtg     5232
Leu Arg Asn Arg Ala Gln Ser Gly Asp Val Gln Gln Phe Lys Lys Val
1730                1735                1740 gtt ttc cag gaa ttt act gat gga tcc ttt act cag ccc tta tac cgt     5280
Val Phe Gln Glu Phe Thr Asp Gly Ser Phe Thr Gln Pro Leu Tyr Arg
1745                1750                1755                1760 gga gaa ctg aac gaa cac ttg gga ctc ttg ggg cca tat ata aga gca     5328
Gly Glu Leu Asn Glu His Leu Gly Leu Leu Gly Pro Tyr Ile Arg Ala
            1765                1770                1775 gaa gtt gaa gac aat atc gtg gta act ttc aaa aac cag gcc tct cgt     5376
Glu Val Glu Asp Asn Ile Val Val Thr Phe Lys Asn Gln Ala Ser Arg
        1780                1785                1790 ccc tac tcc ttc tat tct agt ctt att tct tat gac gaa gat gag gga     5424
Pro Tyr Ser Phe Tyr Ser Ser Leu Ile Ser Tyr Asp Glu Asp Glu Gly
    1795                1800                1805 caa gga gca gaa cct aga aga aag ttt gtc aac cct aat gaa acc aaa     5472
Gln Gly Ala Glu Pro Arg Arg Lys Phe Val Asn Pro Asn Glu Thr Lys
1810                1815                1820 att tac ttt tgg aaa gtg cag cat cat atg gca ccc act aaa gat gag     5520
Ile Tyr Phe Trp Lys Val Gln His His Met Ala Pro Thr Lys Asp Glu
1825                1830                1835                1840 ttt gac tgc aaa gcc tgg gct tat ttt tct gat gtt gat ctg gag aaa     5568
Phe Asp Cys Lys Ala Trp Ala Tyr Phe Ser Asp Val Asp Leu Glu Lys
            1845                1850                1855 gat gtg cac tca ggc ttg att gga ccc ctt ctg atc tgc cgc agt aac     5616
Asp Val His Ser Gly Leu Ile Gly Pro Leu Leu Ile Cys Arg Ser Asn
        1860                1865                1870 aca ctg aac cct gct cat ggg aga caa gtg aca gtg cag gag ttt gcc     5664
Thr Leu Asn Pro Ala His Gly Arg Gln Val Thr Val Gln Glu Phe Ala
    1875                1880                1885 ctg gtt ttc act ata ttc gat gag act aag agc tgg tac ttc act gaa     5712
Leu Val Phe Thr Ile Phe Asp Glu Thr Lys Ser Trp Tyr Phe Thr Glu
1890                1895                1900
```

-continued

```
aac ctg gaa agg aac tgc aga gct ccc tgc aat gtc cag aag gag gac    5760
Asn Leu Glu Arg Asn Cys Arg Ala Pro Cys Asn Val Gln Lys Glu Asp
1905                1910                1915                1920 cct act cta aaa gaa aac ttc cgc ttc cat gca atc aac ggc tat gtg    5808
Pro Thr Leu Lys Glu Asn Phe Arg Phe His Ala Ile Asn Gly Tyr Val
            1925                1930                1935 aag gat aca ctc cct ggc tta gta atg gct cag gat caa aag gtt cga    5856
Lys Asp Thr Leu Pro Gly Leu Val Met Ala Gln Asp Gln Lys Val Arg
        1940                1945                1950 tgg tat ctg ctc agc atg ggc agc aac gaa aac att cat tcc att cac    5904
Trp Tyr Leu Leu Ser Met Gly Ser Asn Glu Asn Ile His Ser Ile His
    1955                1960                1965 ttc agt gga cat gtg ttc act gta cgg aaa aaa gag gaa tat aaa atg    5952
Phe Ser Gly His Val Phe Thr Val Arg Lys Lys Glu Glu Tyr Lys Met
1970                1975                1980 gca gtc tac aac ctc tat cca ggt gtt ttt gag act gtg gaa atg cta    6000
Ala Val Tyr Asn Leu Tyr Pro Gly Val Phe Glu Thr Val Glu Met Leu
1985                1990                1995                2000 cca tcc caa gtt gga atc tgg cgg ata gaa tgc ctt atc ggc gag cac    6048
Pro Ser Gln Val Gly Ile Trp Arg Ile Glu Cys Leu Ile Gly Glu His
            2005                2010                2015 ctg caa gcc ggg atg agc act ctg ttt ctg gtg tac agc aag aag tgt    6096
Leu Gln Ala Gly Met Ser Thr Leu Phe Leu Val Tyr Ser Lys Lys Cys
        2020                2025                2030 cag act cca ctg ggg atg gct tcc gga cac att aga gat ttt cag att    6144
Gln Thr Pro Leu Gly Met Ala Ser Gly His Ile Arg Asp Phe Gln Ile
    2035                2040                2045 aca gct tca gga caa tat gga cag tgg gcc cca aag ctg gcc aga ctt    6192
Thr Ala Ser Gly Gln Tyr Gly Gln Trp Ala Pro Lys Leu Ala Arg Leu
2050                2055                2060 cat tat tcc gga tca atc aat gcc tgg agc acc aag gat ccc ttt tcc    6240
His Tyr Ser Gly Ser Ile Asn Ala Trp Ser Thr Lys Asp Pro Phe Ser
2065                2070                2075                2080 tgg atc aag gtg gat ctc ttg gca ccg atg att att cac ggc atc atg    6288
Trp Ile Lys Val Asp Leu Leu Ala Pro Met Ile Ile His Gly Ile Met
            2085                2090                2095 acc cag ggg gcc cgc cag aag ttc tcc agc ctc tac gtg tct cag ttt    6336
Thr Gln Gly Ala Arg Gln Lys Phe Ser Ser Leu Tyr Val Ser Gln Phe
        2100                2105                2110 atc atc atg tac agt ctg gat ggc aac aag tgg cac agt tac cga ggg    6384
Ile Ile Met Tyr Ser Leu Asp Gly Asn Lys Trp His Ser Tyr Arg Gly
    2115                2120                2125 aat tcc acg ggg acc tta atg gtc ttc ttt ggc aac gtg gat tca tct    6432
Asn Ser Thr Gly Thr Leu Met Val Phe Phe Gly Asn Val Asp Ser Ser
2130                2135                2140 ggg atc aaa cac aat att ttt aac cct ccg att att gct cag tac atc    6480
Gly Ile Lys His Asn Ile Phe Asn Pro Pro Ile Ile Ala Gln Tyr Ile
2145                2150                2155                2160 cgt ttg cac cca acc cat tac agc atc cgc agc act ctt cgc atg gag    6528
Arg Leu His Pro Thr His Tyr Ser Ile Arg Ser Thr Leu Arg Met Glu
            2165                2170                2175 ctc ttg ggc tgt gac ttc aac agt tgc agc atg ccg ctg ggg atg gag    6576
Leu Leu Gly Cys Asp Phe Asn Ser Cys Ser Met Pro Leu Gly Met Glu
        2180                2185                2190 agt aaa gca ata tca gat gct cag atc act gcc tcg tcc tac cta agc    6624
Ser Lys Ala Ile Ser Asp Ala Gln Ile Thr Ala Ser Ser Tyr Leu Ser
    2195                2200                2205 agt atg ctt gcc act tgg tct cct tcc caa gcc cgg ctg cac ctg cag    6672
Ser Met Leu Ala Thr Trp Ser Pro Ser Gln Ala Arg Leu His Leu Gln
2210                2215                2220
```

```
ggc agg act aat gcc tgg aga cct cag gca aat aac cca aaa gag tgg      6720
Gly Arg Thr Asn Ala Trp Arg Pro Gln Ala Asn Asn Pro Lys Glu Trp
2225            2230                2235                2240 ctg caa gtg gac ttc cgg aag acc atg aaa gtc aca gga ata acc acc      6768
Leu Gln Val Asp Phe Arg Lys Thr Met Lys Val Thr Gly Ile Thr Thr
                2245                2250                2255 cag ggg gtg aaa tct ctc ctc atc agc atg tat gtg aag gag ttc ctc      6816
Gln Gly Val Lys Ser Leu Leu Ile Ser Met Tyr Val Lys Glu Phe Leu
            2260                2265                2270 atc tcc agt agt caa gat ggc cat aac tgg act ctg ttt ctt cag aat      6864
Ile Ser Ser Ser Gln Asp Gly His Asn Trp Thr Leu Phe Leu Gln Asn
        2275                2280                2285 ggc aaa gtc aag gtc ttc cag gga aac cgg gac tcc tcc acg cct gtg      6912
Gly Lys Val Lys Val Phe Gln Gly Asn Arg Asp Ser Ser Thr Pro Val
    2290                2295                2300 cgg aac cgt ctc gaa ccc ccg ctg gtg gct cgc tac gtg cgc ctg cac      6960
Arg Asn Arg Leu Glu Pro Pro Leu Val Ala Arg Tyr Val Arg Leu His
2305                2310                2315                2320 ccg cag agc tgg gcg cac cac atc gcc ctg agg ctg gag gtc ctg ggc      7008
Pro Gln Ser Trp Ala His His Ile Ala Leu Arg Leu Glu Val Leu Gly
                2325                2330                2335 tgc gac acc cag cag ccc gcc tga                                      7032
Cys Asp Thr Gln Gln Pro Ala
            2340
```

<210> SEQ ID NO 2
<211> LENGTH: 2343
<212> TYPE: PRT
<213> ORGANISM: Canis familiaris

<400> SEQUENCE: 2

```
Met Gln Val Glu Leu Tyr Thr Cys Cys Phe Leu Cys Leu Leu Pro Phe
1               5                   10                  15

Ser Leu Ser Ala Thr Arg Lys Tyr Tyr Leu Gly Ala Val Glu Leu Ser
            20                  25                  30

Trp Asp Tyr Met Gln Ser Asp Leu Leu Ser Ala Leu His Ala Asp Thr
        35                  40                  45

Ser Phe Ser Ser Arg Val Pro Gly Ser Leu Pro Leu Thr Thr Ser Val
    50                  55                  60

Thr Tyr Arg Lys Thr Val Phe Val Glu Phe Thr Asp Asp Leu Phe Asn
65                  70                  75                  80

Ile Ala Lys Pro Arg Pro Pro Trp Met Gly Leu Leu Gly Pro Thr Ile
                85                  90                  95

Gln Ala Glu Val Tyr Asp Thr Val Ile Val Leu Lys Asn Met Ala
            100                 105                 110

Ser His Pro Val Ser Leu His Ala Val Gly Val Ser Tyr Trp Lys Ala
        115                 120                 125

Ser Glu Gly Ala Glu Tyr Glu Asp Gln Thr Ser Gln Lys Glu Lys Glu
    130                 135                 140

Asp Asp Asn Val Ile Pro Gly Glu Ser His Thr Tyr Val Trp Gln Val
145                 150                 155                 160

Leu Lys Glu Asn Gly Pro Met Ala Ser Asp Pro Pro Cys Leu Thr Tyr
                165                 170                 175

Ser Tyr Phe Ser His Val Asp Leu Val Lys Asp Leu Asn Ser Gly Leu
            180                 185                 190

Ile Gly Ala Leu Leu Val Cys Lys Glu Gly Ser Leu Ala Lys Glu Arg
        195                 200                 205
```

-continued

```
Thr Gln Thr Leu Gln Glu Phe Val Leu Leu Phe Ala Val Phe Asp Glu
    210                 215                 220
Gly Lys Ser Trp His Ser Glu Thr Asn Ala Ser Leu Thr Gln Ala Glu
225                 230                 235                 240
Ala Gln His Glu Leu His Thr Ile Asn Gly Tyr Val Asn Arg Ser Leu
                245                 250                 255
Pro Gly Leu Thr Val Cys His Lys Arg Ser Val Tyr Trp His Val Ile
                260                 265                 270
Gly Met Gly Thr Thr Pro Glu Val His Ser Ile Phe Leu Glu Gly His
            275                 280                 285
Thr Phe Leu Val Arg Asn His Arg Gln Ala Ser Leu Glu Ile Ser Pro
    290                 295                 300
Ile Thr Phe Leu Thr Ala Gln Thr Phe Leu Met Asp Leu Gly Gln Phe
305                 310                 315                 320
Leu Leu Phe Cys His Ile Pro Ser His Gln His Asp Gly Met Glu Ala
                325                 330                 335
Tyr Val Lys Val Asp Ser Cys Pro Glu Glu Pro Gln Leu Arg Met Lys
                340                 345                 350
Asn Asn Glu Asp Lys Asp Tyr Asp Asp Gly Leu Tyr Asp Ser Asp Met
            355                 360                 365
Asp Val Val Ser Phe Asp Asp Asp Ser Ser Ser Pro Phe Ile Gln Ile
    370                 375                 380
Arg Ser Val Ala Lys Lys His Pro Lys Thr Trp Val His Tyr Ile Ala
385                 390                 395                 400
Ala Glu Glu Glu Asp Trp Asp Tyr Ala Pro Ser Gly Pro Thr Pro Asn
                405                 410                 415
Asp Arg Ser His Lys Asn Leu Tyr Leu Asn Asn Gly Pro Gln Arg Ile
                420                 425                 430
Gly Lys Lys Tyr Lys Lys Val Arg Phe Val Ala Tyr Thr Asp Glu Thr
            435                 440                 445
Phe Lys Thr Arg Glu Ala Ile Gln Tyr Glu Ser Gly Ile Leu Gly Pro
    450                 455                 460
Leu Leu Tyr Gly Glu Val Gly Asp Thr Leu Leu Ile Ile Phe Lys Asn
465                 470                 475                 480
Gln Ala Ser Arg Pro Tyr Asn Ile Tyr Pro His Gly Ile Asn Tyr Val
                485                 490                 495
Thr Pro Leu His Thr Gly Arg Leu Pro Lys Gly Val Lys His Leu Lys
            500                 505                 510
Asp Met Pro Ile Leu Pro Gly Glu Ile Phe Lys Tyr Lys Trp Thr Val
    515                 520                 525
Thr Val Glu Asp Gly Pro Thr Lys Ser Asp Pro Arg Cys Leu Thr Arg
530                 535                 540
Tyr Tyr Ser Ser Phe Ile Asn Leu Glu Arg Asp Leu Ala Ser Gly Leu
545                 550                 555                 560
Ile Gly Pro Leu Leu Ile Cys Tyr Lys Glu Ser Val Asp Gln Arg Gly
                565                 570                 575
Asn Gln Met Met Ser Asp Lys Arg Asn Val Ile Leu Phe Ser Val Phe
            580                 585                 590
Asp Glu Asn Arg Ser Trp Tyr Leu Thr Glu Asn Met Gln Arg Phe Leu
    595                 600                 605
Pro Asn Ala Asp Val Val Gln Pro His Asp Pro Glu Phe Gln Leu Ser
610                 615                 620
```

-continued

Asn Ile Met His Ser Ile Asn Gly Tyr Val Phe Asp Asn Leu Gln Leu
625                 630                 635                 640

Ser Val Cys Leu His Glu Val Ala Tyr Trp Tyr Ile Leu Ser Val Gly
            645                 650                 655

Ala Gln Thr Asp Phe Leu Ser Val Phe Phe Ser Gly Tyr Thr Phe Lys
                660                 665                 670

His Lys Met Val Tyr Glu Asp Thr Leu Thr Leu Phe Pro Phe Ser Gly
            675                 680                 685

Glu Thr Val Phe Met Ser Met Glu Asn Pro Gly Leu Trp Val Leu Gly
        690                 695                 700

Cys His Asn Ser Asp Phe Arg Asn Arg Gly Met Thr Ala Leu Leu Lys
705                 710                 715                 720

Val Ser Ser Cys Asn Arg Asn Ile Asp Asp Tyr Tyr Glu Asp Thr Tyr
                725                 730                 735

Glu Asp Ile Pro Thr Pro Leu Leu Asn Glu Asn Asn Val Ile Lys Pro
                740                 745                 750

Arg Ser Phe Ser Gln Asn Ser Arg His Pro Ser Thr Lys Glu Lys Gln
            755                 760                 765

Leu Lys Ala Thr Thr Thr Pro Glu Asn Asp Ile Glu Lys Ile Asp Leu
770                 775                 780

Gln Ser Gly Glu Arg Thr Gln Leu Ile Lys Ala Gln Ser Val Ser Ser
785                 790                 795                 800

Ser Asp Leu Leu Met Leu Leu Gly Gln Asn Pro Thr Pro Arg Gly Leu
                805                 810                 815

Phe Leu Ser Asp Leu Arg Glu Ala Thr Asp Arg Ala Asp Asp His Ser
                820                 825                 830

Arg Gly Ala Ile Glu Arg Asn Lys Gly Pro Pro Glu Val Ala Ser Leu
            835                 840                 845

Arg Pro Glu Leu Arg His Ser Glu Asp Arg Glu Phe Thr Pro Glu Pro
    850                 855                 860

Glu Leu Gln Leu Arg Leu Asn Glu Asn Leu Gly Thr Asn Thr Thr Val
865                 870                 875                 880

Glu Leu Lys Lys Leu Asp Leu Lys Ile Ser Ser Ser Asp Ser Leu
                885                 890                 895

Met Thr Ser Pro Thr Ile Pro Ser Asp Lys Leu Ala Ala Ala Thr Glu
            900                 905                 910

Lys Thr Gly Ser Leu Gly Pro Pro Asn Met Ser Val His Phe Asn Ser
        915                 920                 925

His Leu Gly Thr Ile Val Phe Gly Asn Asn Ser Ser His Leu Ile Gln
    930                 935                 940

Ser Gly Val Pro Leu Glu Leu Ser Glu Glu Asp Asn Asp Ser Lys Leu
945                 950                 955                 960

Leu Glu Ala Pro Leu Met Asn Ile Gln Glu Ser Ser Leu Arg Glu Asn
                965                 970                 975

Val Leu Ser Met Glu Ser Asn Arg Leu Phe Lys Glu Arg Ile Arg
            980                 985                 990

Gly Pro Ala Ser Leu Ile Lys Asp Asn Ala Leu Phe Lys Val Asn Ile
        995                 1000                1005

Ser Ser Val Lys Thr Asn Arg Ala Pro Val Asn Leu Thr Thr Asn Arg
    1010                1015                1020

Lys Thr Arg Val Ala Ile Pro Thr Leu Leu Ile Glu Asn Ser Thr Ser
1025                1030                1035                1040

Val Trp Gln Asp Ile Met Leu Glu Arg Asn Thr Glu Phe Lys Glu Val

-continued

```
                1045                1050                1055
Thr Ser Leu Ile His Asn Glu Thr Phe Met Asp Arg Asn Thr Thr Ala
            1060                1065                1070

Leu Gly Leu Asn His Val Ser Asn Lys Thr Thr Leu Ser Lys Asn Val
        1075                1080                1085

Glu Met Ala His Gln Lys Lys Glu Asp Pro Val Pro Leu Arg Ala Glu
    1090                1095                1100

Asn Pro Asp Leu Ser Ser Lys Ile Pro Phe Leu Pro Asp Trp Ile
1105                1110                1115                1120

Lys Thr His Gly Lys Asn Ser Leu Ser Ser Glu Gln Arg Pro Ser Pro
            1125                1130                1135

Lys Gln Leu Thr Ser Leu Gly Ser Glu Lys Ser Val Lys Asp Gln Asn
        1140                1145                1150

Phe Leu Ser Glu Glu Lys Val Val Gly Glu Asp Glu Phe Thr Lys
            1155                1160                1165

Asp Thr Glu Leu Gln Glu Ile Phe Pro Asn Asn Lys Ser Ile Phe Phe
    1170                1175                1180

Ala Asn Leu Ala Asn Val Gln Glu Asn Asp Thr Tyr Asn Gln Glu Lys
1185                1190                1195                1200

Lys Ser Pro Glu Glu Ile Glu Arg Lys Glu Lys Leu Thr Gln Glu Asn
            1205                1210                1215

Val Ala Leu Pro Gln Ala His Thr Met Ile Gly Thr Lys Asn Phe Leu
        1220                1225                1230

Lys Asn Leu Phe Leu Leu Ser Thr Lys Gln Asn Val Ala Gly Leu Glu
            1235                1240                1245

Glu Gln Pro Tyr Thr Pro Ile Leu Gln Asp Thr Arg Ser Leu Asn Asp
    1250                1255                1260

Ser Pro His Ser Glu Gly Ile His Met Ala Asn Phe Ser Lys Ile Arg
1265                1270                1275                1280

Glu Glu Ala Asn Leu Glu Gly Leu Gly Asn Gln Thr Asn Gln Met Val
            1285                1290                1295

Glu Arg Phe Pro Ser Thr Thr Arg Met Ser Ser Asn Ala Ser Gln His
        1300                1305                1310

Val Ile Thr Gln Arg Gly Lys Arg Ser Leu Lys Gln Pro Arg Leu Ser
            1315                1320                1325

Gln Gly Glu Ile Lys Phe Glu Arg Lys Val Ile Ala Asn Asp Thr Ser
    1330                1335                1340

Thr Gln Trp Ser Lys Asn Met Asn Tyr Leu Ala Gln Gly Thr Leu Thr
1345                1350                1355                1360

Gln Ile Glu Tyr Asn Glu Lys Glu Lys Arg Ala Ile Thr Gln Ser Pro
            1365                1370                1375

Leu Ser Asp Cys Ser Met Arg Asn His Val Thr Ile Gln Met Asn Asp
        1380                1385                1390

Ser Ala Leu Pro Val Ala Lys Glu Ser Ala Ser Pro Ser Val Arg His
        1395                1400                1405

Thr Asp Leu Thr Lys Ile Pro Ser Gln His Asn Ser Ser His Leu Pro
    1410                1415                1420

Ala Ser Ala Cys Asn Tyr Thr Phe Arg Glu Arg Thr Ser Gly Val Gln
1425                1430                1435                1440

Glu Gly Ser His Phe Leu Gln Glu Ala Lys Arg Asn Asn Leu Ser Leu
            1445                1450                1455

Ala Phe Val Thr Leu Gly Ile Thr Glu Gly Gln Gly Lys Phe Ser Ser
        1460                1465                1470
```

```
Leu Gly Lys Ser Ala Thr Asn Gln Pro Met Tyr Lys Lys Leu Glu Asn
        1475                1480                1485

Thr Val Leu Leu Gln Pro Gly Leu Ser Glu Thr Ser Asp Lys Val Glu
    1490                1495                1500

Leu Leu Ser Gln Val His Val Asp Gln Glu Asp Ser Phe Pro Thr Lys
1505                1510                1515                1520

Thr Ser Asn Asp Ser Pro Gly His Leu Asp Leu Met Gly Lys Ile Phe
                1525                1530                1535

Leu Gln Lys Thr Gln Gly Pro Val Lys Met Asn Lys Thr Asn Ser Pro
        1540                1545                1550

Gly Lys Val Pro Phe Leu Lys Trp Ala Thr Glu Ser Ser Glu Lys Ile
        1555                1560                1565

Pro Ser Lys Leu Leu Gly Val Leu Ala Trp Asp Asn His Tyr Asp Thr
        1570                1575                1580

Gln Ile Pro Ser Glu Glu Trp Lys Ser Gln Lys Lys Ser Gln Thr Asn
1585                1590                1595                1600

Thr Ala Phe Lys Arg Lys Asp Thr Ile Leu Pro Leu Gly Pro Cys Glu
                1605                1610                1615

Asn Asn Asp Ser Thr Ala Ala Ile Asn Glu Gly Gln Asp Lys Pro Gln
        1620                1625                1630

Arg Glu Ala Met Trp Ala Lys Gln Gly Glu Pro Gly Arg Leu Cys Ser
        1635                1640                1645

Gln Asn Pro Pro Val Ser Lys His His Gln Arg Glu Ile Thr Val Thr
        1650                1655                1660

Thr Leu Gln Pro Glu Glu Asp Lys Phe Glu Tyr Asp Asp Thr Phe Ser
1665                1670                1675                1680

Ile Glu Met Lys Arg Glu Asp Phe Asp Ile Tyr Gly Asp Tyr Glu Asn
                1685                1690                1695

Gln Gly Leu Arg Ser Phe Gln Lys Lys Thr Arg His Tyr Phe Ile Ala
        1700                1705                1710

Ala Val Glu Arg Leu Trp Asp Tyr Gly Met Ser Arg Ser Pro His Ile
        1715                1720                1725

Leu Arg Asn Arg Ala Gln Ser Gly Asp Val Gln Gln Phe Lys Lys Val
        1730                1735                1740

Val Phe Gln Glu Phe Thr Asp Gly Ser Phe Thr Gln Pro Leu Tyr Arg
1745                1750                1755                1760

Gly Glu Leu Asn Glu His Leu Gly Leu Leu Gly Pro Tyr Ile Arg Ala
                1765                1770                1775

Glu Val Glu Asp Asn Ile Val Val Thr Phe Lys Asn Gln Ala Ser Arg
        1780                1785                1790

Pro Tyr Ser Phe Tyr Ser Ser Leu Ile Ser Tyr Asp Glu Asp Glu Gly
        1795                1800                1805

Gln Gly Ala Glu Pro Arg Arg Lys Phe Val Asn Pro Asn Glu Thr Lys
        1810                1815                1820

Ile Tyr Phe Trp Lys Val Gln His His Met Ala Pro Thr Lys Asp Glu
1825                1830                1835                1840

Phe Asp Cys Lys Ala Trp Ala Tyr Phe Ser Asp Val Asp Leu Glu Lys
                1845                1850                1855

Asp Val His Ser Gly Leu Ile Gly Pro Leu Leu Ile Cys Arg Ser Asn
        1860                1865                1870

Thr Leu Asn Pro Ala His Gly Arg Gln Val Thr Val Gln Glu Phe Ala
        1875                1880                1885
```

-continued

```
Leu Val Phe Thr Ile Phe Asp Glu Thr Lys Ser Trp Tyr Phe Thr Glu
    1890                1895                1900
Asn Leu Glu Arg Asn Cys Arg Ala Pro Cys Asn Val Gln Lys Glu Asp
1905                1910                1915                1920
Pro Thr Leu Lys Glu Asn Phe Arg Phe His Ala Ile Asn Gly Tyr Val
                1925                1930                1935
Lys Asp Thr Leu Pro Gly Leu Val Met Ala Gln Asp Gln Lys Val Arg
            1940                1945                1950
Trp Tyr Leu Leu Ser Met Gly Ser Asn Glu Asn Ile His Ser Ile His
        1955                1960                1965
Phe Ser Gly His Val Phe Thr Val Arg Lys Lys Glu Glu Tyr Lys Met
    1970                1975                1980
Ala Val Tyr Asn Leu Tyr Pro Gly Val Phe Glu Thr Val Glu Met Leu
1985                1990                1995                2000
Pro Ser Gln Val Gly Ile Trp Arg Ile Glu Cys Leu Ile Gly Glu His
                2005                2010                2015
Leu Gln Ala Gly Met Ser Thr Leu Phe Leu Val Tyr Ser Lys Lys Cys
            2020                2025                2030
Gln Thr Pro Leu Gly Met Ala Ser Gly His Ile Arg Asp Phe Gln Ile
        2035                2040                2045
Thr Ala Ser Gly Gln Tyr Gly Gln Trp Ala Pro Lys Leu Ala Arg Leu
    2050                2055                2060
His Tyr Ser Gly Ser Ile Asn Ala Trp Ser Thr Lys Asp Pro Phe Ser
2065                2070                2075                2080
Trp Ile Lys Val Asp Leu Leu Ala Pro Met Ile Ile His Gly Ile Met
                2085                2090                2095
Thr Gln Gly Ala Arg Gln Lys Phe Ser Ser Leu Tyr Val Ser Gln Phe
            2100                2105                2110
Ile Ile Met Tyr Ser Leu Asp Gly Asn Lys Trp His Ser Tyr Arg Gly
        2115                2120                2125
Asn Ser Thr Gly Thr Leu Met Val Phe Phe Gly Asn Val Asp Ser Ser
    2130                2135                2140
Gly Ile Lys His Asn Ile Phe Asn Pro Pro Ile Ile Ala Gln Tyr Ile
2145                2150                2155                2160
Arg Leu His Pro Thr His Tyr Ser Ile Arg Ser Thr Leu Arg Met Glu
                2165                2170                2175
Leu Leu Gly Cys Asp Phe Asn Ser Cys Ser Met Pro Leu Gly Met Glu
            2180                2185                2190
Ser Lys Ala Ile Ser Asp Ala Gln Ile Thr Ala Ser Ser Tyr Leu Ser
        2195                2200                2205
Ser Met Leu Ala Thr Trp Ser Pro Ser Gln Ala Arg Leu His Leu Gln
    2210                2215                2220
Gly Arg Thr Asn Ala Trp Arg Pro Gln Ala Asn Asn Pro Lys Glu Trp
2225                2230                2235                2240
Leu Gln Val Asp Phe Arg Lys Thr Met Lys Val Thr Gly Ile Thr Thr
                2245                2250                2255
Gln Gly Val Lys Ser Leu Leu Ile Ser Met Tyr Val Lys Glu Phe Leu
            2260                2265                2270
Ile Ser Ser Ser Gln Asp Gly His Asn Trp Thr Leu Phe Leu Gln Asn
        2275                2280                2285
Gly Lys Val Lys Val Phe Gln Gly Asn Arg Asp Ser Ser Thr Pro Val
    2290                2295                2300
Arg Asn Arg Leu Glu Pro Pro Leu Val Ala Arg Tyr Val Arg Leu His
```

```
                2305                2310                2315                2320
Pro Gln Ser Trp Ala His His Ile Ala Leu Arg Leu Glu Val Leu Gly
                    2325                2330                2335
Cys Asp Thr Gln Gln Pro Ala
                2340

<210> SEQ ID NO 3
<211> LENGTH: 2332
<212> TYPE: PRT
<213> ORGANISM: Homo sapiens

<400> SEQUENCE: 3

Ala Thr Arg Arg Tyr Tyr Leu Gly Ala Val Glu Leu Ser Trp Asp Tyr
1               5                   10                  15
Met Gln Ser Asp Leu Gly Glu Leu Pro Val Asp Ala Arg Phe Pro Pro
                20                  25                  30
Arg Val Pro Lys Ser Phe Pro Phe Asn Thr Ser Val Val Tyr Lys Lys
            35                  40                  45
Thr Leu Phe Val Glu Phe Thr Val His Leu Phe Asn Ile Ala Lys Pro
        50                  55                  60
Arg Pro Pro Trp Met Gly Leu Leu Gly Pro Thr Ile Gln Ala Glu Val
65                  70                  75                  80
Tyr Asp Thr Val Val Ile Thr Leu Lys Asn Met Ala Ser His Pro Val
                85                  90                  95
Ser Leu His Ala Val Gly Val Ser Tyr Trp Lys Ala Ser Glu Gly Ala
            100                 105                 110
Glu Tyr Asp Asp Gln Thr Ser Gln Arg Glu Lys Glu Asp Asp Lys Val
        115                 120                 125
Phe Pro Gly Gly Ser His Ile Tyr Val Trp Gln Val Leu Lys Glu Asn
130                 135                 140
Gly Pro Met Ala Ser Asp Pro Leu Cys Leu Thr Tyr Ser Tyr Leu Ser
145                 150                 155                 160
His Val Asp Leu Val Lys Asp Leu Asn Ser Gly Leu Ile Gly Ala Leu
                165                 170                 175
Leu Val Cys Gly Arg Glu Gly Ser Leu Ala Lys Glu Lys Thr Gln Thr
            180                 185                 190
Leu His Lys Phe Ile Leu Leu Phe Ala Val Phe Asp Glu Gly Lys Ser
        195                 200                 205
Trp His Ser Glu Thr Lys Asn Ser Leu Met Gln Asp Arg Asp Ala Ala
210                 215                 220
Ser Ala Arg Ala Trp Pro Lys Met His Thr Val Asn Gly Tyr Val Asn
225                 230                 235                 240
Arg Ser Leu Pro Gly Leu Ile Gly Cys His Arg Lys Ser Val Tyr Trp
                245                 250                 255
His Val Ile Gly Met Gly Thr Thr Pro Glu Val His Ser Ile Phe Leu
            260                 265                 270
Glu Gly His Thr Phe Leu Val Arg Asn His Arg Gln Ala Ser Leu Glu
        275                 280                 285
Ile Ser Pro Ile Thr Phe Leu Thr Ala Gln Thr Leu Leu Met Asp Leu
        290                 295                 300
Gly Gln Phe Leu Leu Phe Cys His Ile Ser Ser His Gln His Asp Gly
305                 310                 315                 320
Met Glu Ala Tyr Val Lys Val Asp Ser Cys Pro Glu Glu Pro Gln Leu
                325                 330                 335
```

```
Arg Met Lys Asn Asn Glu Glu Ala Glu Asp Tyr Asp Asp Asp Leu Thr
            340                 345                 350

Asp Ser Glu Met Asp Val Val Arg Phe Asp Asp Asn Ser Pro Ser
            355                 360                 365

Phe Ile Gln Ile Arg Ser Val Ala Lys Lys His Pro Lys Thr Trp Val
            370                 375                 380

His Tyr Ile Ala Ala Glu Glu Asp Trp Asp Tyr Ala Pro Leu Val
385                 390                 395                 400

Leu Ala Pro Asp Asp Arg Ser Tyr Lys Ser Gln Tyr Leu Asn Asn Gly
                405                 410                 415

Pro Gln Arg Ile Gly Arg Lys Tyr Lys Val Arg Phe Met Ala Tyr
                420                 425                 430

Thr Asp Glu Thr Phe Lys Thr Arg Glu Ala Ile Gln His Glu Ser Gly
            435                 440                 445

Ile Leu Gly Pro Leu Leu Tyr Gly Glu Val Gly Asp Thr Leu Leu Ile
            450                 455                 460

Ile Phe Lys Asn Gln Ala Ser Arg Pro Tyr Asn Ile Tyr Pro His Gly
465                 470                 475                 480

Ile Thr Asp Val Arg Pro Leu Tyr Ser Arg Arg Leu Pro Lys Gly Val
                485                 490                 495

Lys His Leu Lys Asp Phe Pro Ile Leu Pro Gly Glu Ile Phe Lys Tyr
            500                 505                 510

Lys Trp Thr Val Thr Val Glu Asp Gly Pro Thr Lys Ser Asp Pro Arg
            515                 520                 525

Cys Leu Thr Arg Tyr Tyr Ser Ser Phe Val Asn Met Glu Arg Asp Leu
            530                 535                 540

Ala Ser Gly Leu Ile Gly Pro Leu Leu Ile Cys Tyr Lys Glu Ser Val
545                 550                 555                 560

Asp Gln Arg Gly Asn Gln Ile Met Ser Asp Lys Arg Asn Val Ile Leu
                565                 570                 575

Phe Ser Val Phe Asp Glu Asn Arg Ser Trp Tyr Leu Thr Glu Asn Ile
                580                 585                 590

Gln Arg Phe Leu Pro Asn Pro Ala Gly Val Gln Leu Glu Asp Pro Glu
            595                 600                 605

Phe Gln Ala Ser Asn Ile Met His Ser Ile Asn Gly Tyr Val Phe Asp
            610                 615                 620

Ser Leu Gln Leu Ser Val Cys Leu His Glu Val Ala Tyr Trp Tyr Ile
625                 630                 635                 640

Leu Ser Ile Gly Ala Gln Thr Asp Phe Leu Ser Val Phe Phe Ser Gly
                645                 650                 655

Tyr Thr Phe Lys His Lys Met Val Tyr Glu Asp Thr Leu Thr Leu Phe
                660                 665                 670

Pro Phe Ser Gly Glu Thr Val Phe Met Ser Met Glu Asn Pro Gly Leu
            675                 680                 685

Trp Ile Leu Gly Cys His Asn Ser Asp Phe Arg Asn Gly Met Thr Ala
            690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Pro Ser Thr Arg
            740                 745                 750

Gln Lys Gln Phe Asn Ala Thr Thr Ile Pro Glu Asn Asp Ile Glu Lys
```

-continued

```
              755                 760                 765
Thr Asp Pro Trp Phe Ala His Arg Thr Pro Met Pro Lys Ile Gln Asn
770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
                820                 825                 830

Glu Met Thr His Phe Arg Pro Gln Leu His His Ser Gly Asp Met Val
                835                 840                 845

Phe Thr Pro Glu Ser Gly Leu Gln Leu Arg Leu Asn Glu Lys Leu Gly
850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
                900                 905                 910

Tyr Asp Ser Gln Leu Asp Thr Thr Leu Phe Gly Lys Lys Ser Ser Pro
                915                 920                 925

Leu Thr Glu Ser Gly Gly Pro Leu Ser Leu Ser Glu Glu Asn Asn Asp
930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
                980                 985                 990

Val Ser Ile Ser Leu Leu Lys Thr Asn Lys Thr Ser Asn Asn Ser Ala
                995                 1000                1005

Thr Asn Arg Lys Thr His Ile Asp Gly Pro Ser Leu Leu Ile Glu Asn
    1010                1015                1020

Ser Pro Ser Val Trp Gln Asn Ile Leu Glu Ser Asp Thr Glu Phe Lys
1025                1030                1035                1040

Lys Val Thr Pro Leu Ile His Asp Arg Met Leu Met Asp Lys Asn Ala
                1045                1050                1055

Thr Ala Leu Arg Leu Asn His Met Ser Asn Lys Thr Thr Ser Ser Lys
                1060                1065                1070

Asn Met Glu Met Val Gln Gln Lys Lys Glu Gly Pro Ile Pro Pro Asp
                1075                1080                1085

Ala Gln Asn Pro Asp Met Ser Phe Phe Lys Met Leu Phe Leu Pro Glu
    1090                1095                1100

Ser Ala Arg Trp Ile Gln Arg Thr His Gly Lys Asn Ser Leu Asn Ser
1105                1110                1115                1120

Gly Gln Gly Pro Ser Pro Lys Gln Leu Val Ser Leu Gly Pro Glu Lys
                1125                1130                1135

Ser Val Glu Gly Gln Asn Phe Leu Ser Glu Lys Asn Lys Val Val Val
                1140                1145                1150

Gly Lys Gly Glu Phe Thr Lys Asp Val Gly Leu Lys Glu Met Val Phe
                1155                1160                1165

Pro Ser Ser Asn Arg Leu Phe Leu Thr Asn Leu Asp Asn Leu His Glu
    1170                1175                1180
```

-continued

Asn Asn Thr His Asn Gln Glu Lys Lys Ile Gln Glu Glu Ile Glu Lys
1185            1190                1195                1200

Lys Glu Thr Leu Ile Gln Glu Asn Val Val Leu Pro Gln Ile His Thr
        1205                1210                1215

Val Thr Gly Thr Lys Asn Phe Met Lys Asn Leu Phe Leu Leu Ser Thr
            1220                1225                1230

Arg Gln Asn Val Glu Gly Ser Tyr Glu Gly Ala Tyr Ala Pro Val Leu
                1235                1240                1245

Gln Asp Phe Arg Ser Leu Asn Asp Ser Thr Asn Arg Thr Lys Lys His
    1250                1255                1260

Thr Ala His Phe Ser Lys Lys Gly Glu Glu Asn Leu Glu Gly Leu
1265            1270                1275                1280

Gly Asn Gln Thr Lys Gln Ile Val Glu Lys Tyr Ala Cys Thr Thr Arg
            1285                1290                1295

Ile Ser Pro Asn Thr Ser Gln Gln Asn Phe Val Thr Gln Arg Ser Lys
                1300                1305                1310

Arg Ala Leu Lys Gln Phe Arg Leu Pro Leu Glu Glu Thr Glu Leu Glu
        1315                1320                1325

Lys Arg Ile Ile Val Asp Asp Thr Ser Thr Gln Trp Ser Lys Asn Met
1330                1335                1340

Lys His Leu Thr Pro Ser Thr Leu Thr Gln Ile Asp Tyr Asn Glu Lys
1345                1350                1355                1360

Glu Lys Gly Ala Ile Thr Gln Ser Pro Leu Ser Asp Cys Leu Thr Arg
                1365                1370                1375

Ser His Ser Ile Pro Gln Ala Asn Arg Ser Pro Leu Pro Ile Ala Lys
            1380                1385                1390

Val Ser Ser Phe Pro Ser Ile Arg Pro Ile Tyr Leu Thr Arg Val Leu
            1395                1400                1405

Phe Gln Asp Asn Ser Ser His Leu Pro Ala Ala Ser Tyr Arg Lys Lys
    1410                1415                1420

Asp Ser Gly Val Gln Glu Ser Ser His Phe Leu Gln Gly Ala Lys Lys
1425            1430                1435                1440

Asn Asn Leu Ser Leu Ala Ile Leu Thr Leu Glu Met Thr Gly Asp Gln
            1445                1450                1455

Arg Glu Val Gly Ser Leu Gly Thr Ser Ala Thr Asn Ser Val Thr Tyr
            1460                1465                1470

Lys Lys Val Glu Asn Thr Val Leu Pro Lys Pro Asp Leu Pro Lys Thr
        1475                1480                1485

Ser Gly Lys Val Glu Leu Leu Pro Lys Val His Ile Tyr Gln Lys Asp
    1490                1495                1500

Leu Phe Pro Thr Glu Thr Ser Asn Gly Ser Pro Gly His Leu Asp Leu
1505            1510                1515                1520

Val Glu Gly Ser Leu Leu Gln Gly Thr Glu Gly Ala Ile Lys Trp Asn
            1525                1530                1535

Glu Ala Asn Arg Pro Gly Lys Val Pro Phe Leu Arg Val Ala Thr Glu
            1540                1545                1550

Ser Ser Ala Lys Thr Pro Ser Lys Leu Leu Asp Pro Leu Ala Trp Asp
        1555                1560                1565

Asn His Tyr Gly Thr Gln Ile Pro Lys Glu Glu Trp Lys Ser Gln Glu
    1570                1575                1580

Lys Ser Pro Glu Lys Thr Ala Phe Lys Lys Asp Thr Ile Leu Ser
1585            1590                1595                1600

```
Leu Asn Ala Cys Glu Ser Asn His Ala Ile Ala Ala Ile Asn Glu Gly
            1605                1610                1615

Gln Asn Lys Pro Glu Ile Glu Val Thr Trp Ala Lys Gln Gly Arg Thr
        1620                1625                1630

Glu Arg Leu Cys Ser Gln Asn Pro Val Leu Lys Arg His Gln Arg
    1635                1640                1645

Glu Ile Thr Arg Thr Thr Leu Gln Ser Asp Gln Glu Glu Ile Asp Tyr
    1650                1655                1660

Asp Asp Thr Ile Ser Val Glu Met Lys Lys Glu Asp Phe Asp Ile Tyr
1665                1670                1675                1680

Asp Glu Asp Glu Asn Gln Ser Pro Arg Ser Phe Gln Lys Lys Thr Arg
            1685                1690                1695

His Tyr Phe Ile Ala Ala Val Glu Arg Leu Trp Asp Tyr Gly Met Ser
            1700                1705                1710

Ser Ser Pro His Val Leu Arg Asn Arg Ala Gln Ser Gly Ser Val Pro
        1715                1720                1725

Gln Phe Lys Lys Val Val Phe Gln Glu Phe Thr Asp Gly Ser Phe Thr
    1730                1735                1740

Gln Pro Leu Tyr Arg Gly Glu Leu Asn Glu His Leu Gly Leu Leu Gly
1745                1750                1755                1760

Pro Tyr Ile Arg Ala Glu Val Glu Asp Asn Ile Met Val Thr Phe Arg
            1765                1770                1775

Asn Gln Ala Ser Arg Pro Tyr Ser Phe Tyr Ser Ser Leu Ile Ser Tyr
            1780                1785                1790

Glu Glu Asp Gln Arg Gln Gly Ala Glu Pro Pro Lys Asn Phe Val Lys
        1795                1800                1805

Pro Asn Glu Thr Lys Thr Tyr Phe Trp Lys Val Gln His His Met Ala
    1810                1815                1820

Pro Thr Lys Asp Glu Phe Asp Cys Lys Ala Trp Ala Tyr Phe Ser Asp
1825                1830                1835                1840

Val Asp Leu Glu Lys Asp Val His Ser Gly Leu Ile Gly Pro Leu Leu
            1845                1850                1855

Val Cys His Thr Asn Thr Leu Asn Pro Ala His Gly Arg Gln Val Thr
            1860                1865                1870

Val Gln Glu Phe Ala Leu Phe Phe Thr Ile Phe Asp Glu Thr Lys Ser
        1875                1880                1885

Trp Tyr Phe Thr Glu Asn Met Glu Arg Asn Cys Arg Ala Pro Cys Asn
    1890                1895                1900

Ile Gln Met Glu Asp Pro Thr Phe Lys Glu Asn Tyr Arg Phe His Ala
1905                1910                1915                1920

Ile Asn Gly Tyr Ile Met Asp Thr Leu Pro Gly Leu Val Met Ala Gln
            1925                1930                1935

Asp Gln Arg Ile Arg Trp Tyr Leu Leu Ser Met Gly Ser Asn Glu Asn
            1940                1945                1950

Ile His Ser Ile His Phe Ser Gly His Val Phe Thr Val Arg Lys Lys
        1955                1960                1965

Glu Glu Tyr Lys Met Ala Leu Tyr Asn Leu Tyr Pro Gly Val Phe Glu
    1970                1975                1980

Thr Val Glu Met Leu Pro Ser Lys Ala Gly Ile Trp Arg Val Glu Cys
1985                1990                1995                2000

Leu Ile Gly Glu His Leu His Ala Gly Met Ser Thr Leu Phe Leu Val
            2005                2010                2015

Tyr Ser Asn Lys Cys Gln Thr Pro Leu Gly Met Ala Ser Gly His Ile
```

-continued

Arg Asp Phe Gln Ile Thr Ala Ser Gly Gln Tyr Gly Gln Trp Ala Pro
                2035                2040                2045

Lys Leu Ala Arg Leu His Tyr Ser Gly Ser Ile Asn Ala Trp Ser Thr
        2050                2055                2060

Lys Glu Pro Phe Ser Trp Ile Lys Val Asp Leu Leu Ala Pro Met Ile
2065                2070                2075                2080

Ile His Gly Ile Lys Thr Gln Gly Ala Arg Gln Lys Phe Ser Ser Leu
                2085                2090                2095

Tyr Ile Ser Gln Phe Ile Ile Met Tyr Ser Leu Asp Gly Lys Lys Trp
                2100                2105                2110

Gln Thr Tyr Arg Gly Asn Ser Thr Gly Thr Leu Met Val Phe Phe Gly
                2115                2120                2125

Asn Val Asp Ser Ser Gly Ile Lys His Asn Ile Phe Asn Pro Pro Ile
2130                2135                2140

Ile Ala Arg Tyr Ile Arg Leu His Pro Thr His Tyr Ser Ile Arg Ser
2145                2150                2155                2160

Thr Leu Arg Met Glu Leu Met Gly Cys Asp Leu Asn Ser Cys Ser Met
                2165                2170                2175

Pro Leu Gly Met Glu Ser Lys Ala Ile Ser Asp Ala Gln Ile Thr Ala
                2180                2185                2190

Ser Ser Tyr Phe Thr Asn Met Phe Ala Thr Trp Ser Pro Ser Lys Ala
                2195                2200                2205

Arg Leu His Leu Gln Gly Arg Ser Asn Ala Trp Arg Pro Gln Val Asn
                2210                2215                2220

Asn Pro Lys Glu Trp Leu Gln Val Asp Phe Gln Lys Thr Met Lys Val
2225                2230                2235                2240

Thr Gly Val Thr Thr Gln Gly Val Lys Ser Leu Leu Thr Ser Met Tyr
                2245                2250                2255

Val Lys Glu Phe Leu Ile Ser Ser Ser Gln Asp Gly His Gln Trp Thr
                2260                2265                2270

Leu Phe Phe Gln Asn Gly Lys Val Lys Val Phe Gln Gly Asn Gln Asp
                2275                2280                2285

Ser Phe Thr Pro Val Val Asn Ser Leu Asp Pro Pro Leu Leu Thr Arg
                2290                2295                2300

Tyr Leu Arg Ile His Pro Gln Ser Trp Val His Gln Ile Ala Leu Arg
2305                2310                2315                2320

Met Glu Val Leu Gly Cys Glu Ala Gln Asp Leu Tyr
                2325                2330

<210> SEQ ID NO 4
<211> LENGTH: 2304
<212> TYPE: PRT
<213> ORGANISM: Mus musculus

<400> SEQUENCE: 4

Ala Ile Arg Arg Tyr Tyr Leu Gly Ala Val Glu Leu Ser Trp Asn Tyr
1               5                   10                  15

Ile Gln Ser Asp Leu Leu Ser Val Leu His Thr Asp Ser Arg Phe Leu
                20                  25                  30

Pro Arg Met Ser Thr Ser Phe Pro Phe Asn Thr Ser Ser Ile Met Tyr
            35                  40                  45

Lys Lys Thr Val Phe Val Glu Phe Thr Asp Gln Leu Phe Asn Ile Ala
50                  55                  60

-continued

```
Lys Pro Arg Pro Pro Trp Met Gly Leu Leu Gly Pro Thr Ile Trp Thr
 65                  70                  75                  80

Glu Val His Asp Thr Val Ile Thr Leu Lys Asn Met Ala Ser His
                 85                  90                  95

Pro Val Ser Leu His Ala Val Gly Val Ser Tyr Trp Lys Ala Ser Glu
                100                 105                 110

Gly Asp Glu Tyr Glu Asp Gln Thr Ser Gln Met Glu Lys Glu Asp Asp
                115                 120                 125

Lys Val Phe Pro Gly Glu Ser His Thr Tyr Val Trp Gln Val Leu Lys
    130                 135                 140

Glu Asn Gly Pro Met Ala Ser Asp Pro Pro Cys Leu Thr Tyr Ser Tyr
145                 150                 155                 160

Met Ser His Val Asp Leu Val Lys Asp Leu Asn Ser Gly Leu Ile Gly
                165                 170                 175

Ala Leu Leu Val Cys Lys Glu Gly Ser Leu Ser Lys Glu Arg Thr Gln
                180                 185                 190

Met Leu Tyr Gln Phe Val Leu Leu Phe Ala Val Phe Asp Glu Gly Lys
                195                 200                 205

Ser Trp His Ser Glu Thr Asn Asp Ser Tyr Thr Asn Asp Ser Tyr Thr
    210                 215                 220

Gln Ser Met Asp Ser Ala Ser Ala Arg Asp Trp Pro Lys Met His Thr
225                 230                 235                 240

Val Asn Gly Tyr Val Asn Arg Ser Leu Pro Gly Leu Ile Gly Cys His
                245                 250                 255

Arg Lys Ser Val Tyr Trp His Val Ile Gly Met Gly Thr Thr Pro Glu
                260                 265                 270

Ile His Ser Ile Phe Leu Glu Gly His Thr Phe Phe Val Arg Asn His
                275                 280                 285

Arg Gln Ala Ser Leu Glu Ile Ser Pro Ile Thr Phe Leu Thr Ala Gln
    290                 295                 300

Thr Leu Leu Ile Asp Leu Gly Gln Phe Leu Leu Phe Cys His Ile Ser
305                 310                 315                 320

Ser His Lys His Asp Gly Met Glu Ala Tyr Val Lys Val Asp Ser Cys
                325                 330                 335

Pro Glu Glu Ser Gln Trp Gln Lys Lys Asn Asn Asn Glu Glu Met Glu
                340                 345                 350

Asp Tyr Asp Asp Asp Leu Tyr Ser Glu Met Asp Met Phe Thr Leu Asp
                355                 360                 365

Tyr Asp Ser Ser Pro Phe Ile Gln Ile Arg Ser Val Ala Lys Lys Tyr
    370                 375                 380

Pro Lys Thr Trp Ile His Tyr Ile Ser Ala Glu Glu Asp Trp Asp
385                 390                 395                 400

Tyr Ala Pro Ser Val Pro Thr Ser Asp Asn Gly Ser Tyr Lys Ser Gln
                405                 410                 415

Tyr Leu Ser Asn Gly Pro His Arg Ile Gly Arg Lys Tyr Lys Lys Val
                420                 425                 430

Arg Phe Ile Ala Tyr Thr Asp Glu Thr Phe Lys Thr Arg Glu Thr Ile
                435                 440                 445

Gln His Glu Ser Gly Leu Leu Gly Pro Leu Leu Tyr Gly Glu Val Gly
                450                 455                 460

Asp Thr Leu Leu Ile Ile Phe Lys Asn Gln Ala Ser Arg Pro Tyr Asn
465                 470                 475                 480

Ile Tyr Pro His Gly Ile Thr Asp Val Ser Pro Leu His Ala Arg Arg
```

-continued

```
                    485                 490                 495
Leu Pro Arg Gly Ile Lys His Val Lys Asp Leu Pro Ile His Pro Gly
                500                 505                 510
Glu Ile Phe Lys Tyr Lys Trp Thr Val Thr Val Glu Asp Gly Pro Thr
                515                 520                 525
Lys Ser Asp Pro Arg Cys Leu Thr Arg Tyr Tyr Ser Ser Phe Ile Asn
            530                 535                 540
Pro Glu Arg Asp Leu Ala Ser Gly Leu Ile Gly Pro Leu Leu Ile Cys
545                 550                 555                 560
Tyr Lys Glu Ser Val Asp Gln Arg Gly Asn Gln Met Met Ser Asp Lys
                565                 570                 575
Arg Asn Val Ile Leu Phe Ser Ile Phe Asp Glu Asn Gln Ser Trp Ile
            580                 585                 590
Thr Glu Asn Met Gln Arg Phe Leu Pro Asn Ala Ala Lys Thr Gln Pro
            595                 600                 605
Gln Asp Pro Gly Phe Gln Ala Ser Asn Ile Met His Ser Ile Asn Gly
    610                 615                 620
Tyr Val Phe Asp Ser Leu Glu Leu Thr Val Cys Leu His Glu Val Ala
625                 630                 635                 640
Tyr Trp His Ile Leu Ser Val Gly Ala Gln Thr Asp Phe Leu Ser Ile
                645                 650                 655
Phe Phe Ser Gly Tyr Thr Phe Lys His Lys Met Val Tyr Glu Asp Thr
                660                 665                 670
Leu Thr Leu Phe Pro Phe Ser Gly Glu Thr Val Phe Met Ser Met Glu
            675                 680                 685
Asn Pro Gly Leu Trp Val Leu Gly Cys His Asn Ser Asp Phe Arg Lys
    690                 695                 700
Arg Gly Met Thr Ala Leu Leu Lys Val Ser Ser Cys Asp Lys Ser Thr
705                 710                 715                 720
Ser Asp Tyr Tyr Glu Glu Ile Tyr Glu Asp Ile Pro Thr Gln Leu Val
                725                 730                 735
Asn Glu Asn Asn Val Ile Asp Pro Arg Ser Phe Phe Gln Asn Thr Asn
            740                 745                 750
His Pro Asn Thr Arg Lys Lys Lys Phe Lys Asp Ser Thr Ile Pro Lys
            755                 760                 765
Asn Asp Met Glu Lys Ile Glu Pro Gln Phe Glu Glu Ile Ala Glu Met
770                 775                 780
Leu Lys Val Gln Ser Val Ser Val Ser Asp Met Leu Met Leu Leu Gly
785                 790                 795                 800
Gln Ser His Pro Thr Pro His Gly Leu Phe Leu Ser Asp Gly Gln Glu
            805                 810                 815
Ala Ile Tyr Glu Ala Ile His Asp Asp His Ser Pro Asn Ala Ile Asp
            820                 825                 830
Ser Asn Glu Gly Pro Ser Lys Val Thr Gln Leu Arg Pro Glu Ser His
    835                 840                 845
His Ser Glu Lys Ile Val Phe Thr Pro Gln Pro Gly Leu Gln Leu Arg
    850                 855                 860
Ser Asn Lys Ser Leu Glu Thr Thr Ile Glu Val Lys Trp Lys Lys Leu
865                 870                 875                 880
Gly Leu Gln Val Ser Ser Leu Pro Ser Asn Leu Met Thr Thr Thr Ile
                885                 890                 895
Leu Ser Asp Asn Leu Lys Ala Thr Phe Glu Lys Thr Asp Ser Ser Gly
            900                 905                 910
```

-continued

```
Phe Pro Asp Met Pro Val His Ser Ser Lys Leu Ser Thr Thr Ala
    915                 920                 925
Phe Gly Lys Lys Ala Tyr Ser Leu Val Gly Ser His Val Pro Leu Asn
    930                 935                 940
Ala Ser Glu Glu Asn Ser Asp Ser Asn Ile Leu Asp Ser Thr Leu Met
945                 950                 955                 960
Tyr Ser Gln Glu Ser Leu Pro Arg Asp Asn Ile Leu Ser Ile Glu Asn
                965                 970                 975
Asp Arg Leu Leu Arg Glu Lys Arg Phe His Gly Ile Ala Leu Leu Thr
                980                 985                 990
Lys Asp Asn Thr Leu Phe Lys Asp Asn Val Ser Leu Met Lys Thr Asn
                995                 1000                1005
Lys Thr Tyr Asn His Ser Thr Thr Asn Glu Lys Leu His Thr Glu Ser
    1010                1015                1020
Pro Thr Ser Ile Glu Asn Ser Thr Asp Leu Gln Asp Ala Ile Leu
1025                1030                1035                1040
Lys Val Asn Ser Glu Ile Gln Glu Val Thr Ala Leu Ile His Asp Gly
                1045                1050                1055
Thr Leu Leu Gly Lys Asn Ser Thr Tyr Leu Arg Leu Asn His Met Leu
    1060                1065                1070
Asn Arg Thr Thr Ser Thr Lys Asn Lys Asp Ile Phe His Arg Lys Asp
    1075                1080                1085
Glu Asp Pro Ile Pro Gln Asp Glu Glu Asn Thr Ile Met Pro Phe Ser
    1090                1095                1100
Lys Met Leu Phe Leu Ser Glu Ser Ser Asn Trp Phe Lys Lys Thr Asn
1105                1110                1115                1120
Gly Asn Asn Ser Leu Asn Ser Glu Gln Glu His Ser Pro Lys Gln Leu
                1125                1130                1135
Val Tyr Leu Met Phe Lys Lys Tyr Val Lys Asn Gln Ser Phe Leu Ser
                1140                1145                1150
Glu Lys Asn Lys Val Thr Val Glu Gln Asp Gly Phe Thr Lys Asn Ile
    1155                1160                1165
Gly Leu Lys Asp Met Ala Phe Pro His Asn Met Ser Ile Phe Leu Thr
    1170                1175                1180
Thr Leu Ser Asn Val His Glu Asn Gly Arg His Asn Gln Glu Lys Asn
1185                1190                1195                1200
Ile Gln Glu Glu Ile Glu Lys Glu Ala Leu Ile Glu Glu Lys Val Val
                1205                1210                1215
Leu Pro Gln Val His Glu Ala Thr Gly Ser Lys Asn Phe Leu Lys Asp
                1220                1225                1230
Ile Leu Ile Leu Gly Thr Arg Gln Asn Ile Ser Leu Tyr Glu Val His
    1235                1240                1245
Val Pro Val Leu Gln Asn Ile Thr Ser Ile Asn Asn Ser Thr Asn Thr
    1250                1255                1260
Val Gln Ile His Met Glu His Phe Phe Lys Arg Arg Lys Asp Lys Glu
1265                1270                1275                1280
Thr Asn Ser Glu Gly Leu Val Asn Lys Thr Arg Glu Met Val Lys Asn
                1285                1290                1295
Tyr Pro Ser Gln Lys Asn Ile Thr Thr Gln Arg Ser Lys Arg Ala Leu
                1300                1305                1310
Gly Gln Phe Arg Leu Ser Thr Gln Trp Leu Lys Thr Ile Asn Cys Ser
    1315                1320                1325
```

```
Thr Gln Cys Ile Ile Lys Gln Ile Asp His Ser Lys Glu Met Lys Lys
    1330                1335                1340

Phe Ile Thr Lys Ser Ser Leu Ser Asp Ser Ser Val Ile Lys Ser Thr
1345                1350                1355                1360

Thr Gln Thr Asn Ser Ser Asp Ser His Ile Val Lys Thr Ser Ala Phe
            1365                1370                1375

Pro Pro Ile Asp Leu Lys Arg Ser Pro Phe Gln Asn Lys Phe Ser His
        1380                1385                1390

Val Gln Ala Ser Ser Tyr Ile Tyr Asp Phe Lys Thr Lys Ser Ser Arg
    1395                1400                1405

Ile Gln Glu Ser Asn Asn Phe Leu Lys Glu Thr Lys Ile Asn Asn Pro
    1410                1415                1420

Ser Leu Ala Ile Leu Pro Trp Asn Met Phe Ile Asp Gln Gly Lys Phe
1425                1430                1435                1440

Thr Ser Pro Gly Lys Ser Asn Thr Asn Ser Val Thr Tyr Lys Lys Arg
            1445                1450                1455

Glu Asn Ile Ile Phe Leu Lys Pro Thr Leu Pro Glu Glu Ser Gly Lys
        1460                1465                1470

Ile Glu Leu Leu Pro Gln Val Ser Ile Gln Glu Glu Ile Leu Pro
    1475                1480                1485

Thr Glu Thr Ser His Gly Ser Pro Gly His Leu Asn Leu Met Lys Glu
    1490                1495                1500

Val Phe Leu Gln Lys Ile Gln Gly Pro Thr Lys Trp Asn Lys Ala Lys
1505                1510                1515                1520

Arg His Gly Glu Ser Ile Lys Gly Lys Thr Glu Ser Ser Lys Asn Thr
            1525                1530                1535

Arg Ser Lys Leu Leu Asn His His Ala Trp Asp Tyr His Tyr Ala Ala
            1540                1545                1550

Gln Ile Pro Lys Asp Met Trp Lys Ser Lys Glu Lys Ser Pro Glu Ile
    1555                1560                1565

Ile Ser Ile Lys Gln Glu Asp Thr Ile Leu Ser Leu Arg Pro His Gly
    1570                1575                1580

Asn Ser His Ser Ile Gly Ala Asn Glu Lys Gln Asn Trp Pro Gln Arg
1585                1590                1595                1600

Glu Thr Thr Trp Val Lys Gln Gly Gln Thr Gln Arg Thr Cys Ser Gln
            1605                1610                1615

Ile Pro Pro Val Leu Lys Arg His Gln Arg Glu Leu Ser Ala Phe Gln
        1620                1625                1630

Ser Glu Gln Glu Ala Thr Asp Tyr Asp Asp Ala Ile Thr Ile Glu Thr
            1635                1640                1645

Ile Glu Asp Phe Asp Ile Tyr Ser Glu Asp Ile Lys Gln Gly Pro Arg
    1650                1655                1660

Ser Phe Gln Gln Lys Thr Arg His Tyr Phe Ile Ala Ala Val Glu Arg
1665                1670                1675                1680

Leu Trp Asp Tyr Gly Met Ser Thr Ser His Val Leu Arg Asn Arg Tyr
            1685                1690                1695

Gln Ser Asp Asn Val Pro Gln Phe Lys Lys Val Val Phe Gln Glu Phe
            1700                1705                1710

Thr Asp Gly Ser Phe Ser Gln Pro Leu Tyr Arg Gly Glu Leu Asn Glu
        1715                1720                1725

His Leu Gly Leu Leu Gly Pro Tyr Ile Arg Ala Glu Val Glu Asp Asn
    1730                1735                1740

Ile Met Val Thr Phe Lys Asn Gln Ala Ser Arg Pro Tyr Ser Phe Tyr
```

```
                1745                1750                1755                1760
Ser Ser Leu Ile Ser Tyr Lys Glu Asp Gln Arg Gly Glu Glu Pro Arg
                    1765                1770                1775

Arg Asn Phe Val Lys Pro Asn Glu Thr Lys Ile Tyr Phe Trp Lys Val
            1780                1785                1790

Gln His His Met Ala Pro Thr Glu Asp Glu Phe Asp Cys Lys Ala Trp
        1795                1800                1805

Ala Tyr Phe Ser Asp Val Asp Leu Glu Arg Asp Met His Ser Gly Leu
    1810                1815                1820

Ile Gly Pro Leu Leu Ile Cys His Ala Asn Thr Leu Asn Pro Ala His
1825                1830                1835                1840

Gly Arg Gln Val Ser Val Gln Glu Phe Ala Leu Leu Phe Thr Ile Phe
                1845                1850                1855

Asp Glu Thr Lys Ser Trp Tyr Phe Thr Glu Asn Val Lys Arg Asn Cys
            1860                1865                1870

Lys Thr Pro Cys Asn Phe Gln Met Glu Asp Pro Thr Leu Lys Glu Asn
        1875                1880                1885

Tyr Arg Phe His Ala Ile Asn Gly Tyr Val Met Asp Thr Leu Pro Gly
    1890                1895                1900

Leu Val Met Ala Gln Asp Gln Arg Ile Arg Trp Tyr Leu Leu Ser Met
1905                1910                1915                1920

Gly Asn Asn Glu Asn Ile Gln Ser Ile His Phe Ser Gly His Val Phe
                1925                1930                1935

Thr Val Arg Lys Lys Glu Glu Tyr Lys Met Ala Val Tyr Asn Leu Tyr
            1940                1945                1950

Pro Gly Val Phe Glu Thr Leu Glu Met Ile Pro Ser Arg Ala Gly Ile
        1955                1960                1965

Trp Arg Val Glu Cys Leu Ile Gly Glu His Leu Gln Ala Gly Met Ser
    1970                1975                1980

Thr Leu Phe Leu Val Tyr Ser Lys Gln Cys Gln Ile Pro Leu Gly Met
1985                1990                1995                2000

Ala Ser Gly Ser Ile Arg Asp Phe Gln Ile Thr Ala Ser Gly His Tyr
                2005                2010                2015

Gly Gln Trp Ala Pro Asn Leu Ala Arg His Tyr Ser Gly Ser Ile Asn
            2020                2025                2030

Ala Trp Ser Thr Lys Glu Pro Phe Ser Trp Ile Lys Val Asp Leu Leu
        2035                2040                2045

Ala Pro Met Ile Val His Gly Ile Lys Thr Gln Gly Ala Arg Gln Lys
    2050                2055                2060

Phe Ser Ser Leu Tyr Ile Ser Gln Phe Ile Ile Met Tyr Ser Leu Asp
2065                2070                2075                2080

Gly Lys Lys Trp Leu Ser Tyr Gln Gly Asn Ser Thr Gly Thr Leu Met
                2085                2090                2095

Val Phe Phe Gly Asn Val Asp Ser Ser Gly Ile Lys His Asn Ser Phe
            2100                2105                2110

Asn Pro Pro Ile Ile Ala Arg Tyr Ile Arg Leu His Pro Thr His Ser
        2115                2120                2125

Ser Ile Arg Ser Thr Leu Arg Met Glu Leu Met Gly Cys Asp Leu Asn
    2130                2135                2140

Ser Cys Ser Ile Pro Leu Gly Met Glu Ser Lys Val Ile Ser Asp Thr
2145                2150                2155                2160

Gln Ile Thr Ala Ser Ser Tyr Phe Thr Asn Met Phe Ala Thr Trp Ser
                2165                2170                2175
```

-continued

```
Pro Ser Gln Ala Arg Leu His Leu Gln Gly Arg Thr Asn Ala Trp Arg
        2180                2185                2190

Pro Gln Val Asn Asp Pro Lys Gln Trp Leu Gln Val Asp Leu Gln Lys
        2195                2200                2205

Thr Met Lys Val Thr Gly Ile Ile Thr Gln Gly Val Lys Ser Leu Phe
        2210                2215                2220

Thr Ser Met Phe Val Lys Glu Phe Leu Ile Ser Ser Ser Gln Asp Gly
2225                2230                2235                2240

His His Trp Thr Gln Ile Leu Tyr Asn Gly Lys Val Lys Val Phe Gln
        2245                2250                2255

Gly Asn Gln Asp Ser Ser Thr Pro Met Met Asn Ser Leu Asp Pro Pro
        2260                2265                2270

Leu Leu Thr Arg Tyr Leu Arg Ile His Pro Gln Ile Trp Glu His Gln
        2275                2280                2285

Ile Ala Leu Arg Leu Glu Ile Leu Gly Cys Glu Ala Gln Gln Gln Tyr
        2290                2295                2300

<210> SEQ ID NO 5
<211> LENGTH: 2115
<212> TYPE: PRT
<213> ORGANISM: Sus spp.

<400> SEQUENCE: 5

Ala Ile Arg Arg Tyr Tyr Leu Gly Ala Val Glu Leu Ser Trp Asp Tyr
1               5                   10                  15

Arg Gln Ser Glu Leu Leu Arg Glu Leu His Val Asp Thr Arg Phe Pro
            20                  25                  30

Ala Thr Ala Pro Gly Ala Leu Pro Leu Gly Pro Ser Val Leu Tyr Lys
        35                  40                  45

Lys Thr Val Phe Val Glu Phe Thr Asp Gln Leu Phe Ser Val Ala Arg
    50                  55                  60

Pro Arg Pro Pro Trp Met Gly Leu Leu Gly Pro Thr Ile Gln Ala Glu
65              70                  75                  80

Val Tyr Asp Thr Val Val Thr Leu Lys Asn Met Ala Ser His Pro
            85                  90                  95

Val Ser Leu His Ala Val Gly Val Ser Phe Trp Lys Ser Ser Glu Gly
            100                 105                 110

Ala Glu Tyr Glu Asp His Thr Ser Gln Arg Glu Lys Glu Asp Asp Lys
        115                 120                 125

Val Leu Pro Gly Lys Ser Gln Thr Tyr Val Trp Gln Val Leu Lys Glu
    130                 135                 140

Asn Gly Pro Thr Ala Ser Asp Pro Pro Cys Leu Thr Tyr Ser Tyr Leu
145                 150                 155                 160

Ser His Val Asp Leu Val Lys Asp Leu Asn Ser Gly Leu Ile Gly Ala
                165                 170                 175

Leu Leu Val Cys Arg Glu Gly Ser Leu Thr Arg Glu Arg Thr Gln Asn
            180                 185                 190

Leu His Glu Phe Val Leu Leu Phe Ala Val Phe Asp Glu Gly Lys Ser
        195                 200                 205

Trp His Ser Ala Arg Asn Asp Ser Trp Thr Arg Ala Met Asp Pro Ala
        210                 215                 220

Pro Ala Arg Ala Gln Pro Ala Met His Thr Val Asn Gly Tyr Val Asn
225                 230                 235                 240

Arg Ser Leu Pro Gly Leu Ile Gly Cys His Lys Lys Ser Val Tyr Trp
```

-continued

```
                245                 250                 255
His Val Ile Gly Met Gly Thr Ser Pro Glu Val His Ser Ile Phe Leu
                260                 265                 270
Glu Gly His Thr Phe Leu Val Arg His His Arg Gln Ala Ser Leu Glu
            275                 280                 285
Ile Ser Pro Leu Thr Phe Leu Thr Ala Gln Thr Phe Leu Met Asp Leu
        290                 295                 300
Gly Gln Phe Leu Leu Phe Cys His Ile Ser Ser His His Gly Gly
305                 310                 315                 320
Met Glu Ala His Val Arg Val Glu Ser Cys Ala Glu Pro Gln Leu
                325                 330                 335
Arg Arg Lys Ala Asp Glu Glu Asp Tyr Asp Asp Asn Leu Tyr Asp
                340                 345                 350
Ser Asp Met Asp Val Val Arg Leu Asp Gly Asp Asp Val Ser Pro Phe
            355                 360                 365
Ile Gln Ile Arg Ser Val Ala Lys Lys His Pro Lys Thr Trp Val His
        370                 375                 380
Tyr Ile Ser Ala Glu Glu Glu Asp Trp Asp Tyr Ala Pro Ala Val Pro
385                 390                 395                 400
Ser Pro Ser Asp Arg Ser Tyr Lys Ser Leu Tyr Leu Asn Ser Gly Pro
                405                 410                 415
Gln Arg Ile Gly Arg Lys Tyr Lys Lys Ala Arg Phe Val Ala Tyr Thr
                420                 425                 430
Asp Val Thr Phe Lys Thr Arg Lys Ala Ile Pro Tyr Glu Ser Gly Ile
            435                 440                 445
Leu Gly Pro Leu Leu Tyr Gly Glu Val Gly Asp Thr Leu Leu Ile Ile
        450                 455                 460
Phe Lys Asn Lys Ala Ser Arg Pro Tyr Asn Ile Tyr Pro His Gly Ile
465                 470                 475                 480
Thr Asp Val Ser Ala Leu His Pro Gly Arg Leu Leu Lys Gly Trp Lys
                485                 490                 495
His Leu Lys Asp Met Pro Ile Leu Pro Gly Glu Thr Phe Lys Tyr Lys
                500                 505                 510
Trp Thr Val Thr Val Glu Asp Gly Pro Thr Lys Ser Asp Pro Arg Cys
            515                 520                 525
Leu Thr Arg Tyr Tyr Ser Ser Ser Ile Asn Leu Glu Lys Asp Leu Ala
        530                 535                 540
Ser Gly Leu Ile Gly Pro Leu Leu Ile Cys Tyr Lys Glu Ser Val Asp
545                 550                 555                 560
Gln Arg Gly Gly Asn Gln Met Met Ser Asp Lys Arg Asn Val Ile Leu
                565                 570                 575
Phe Ser Val Phe Asp Glu Asn Gln Ser Trp Tyr Leu Ala Glu Asn Ile
            580                 585                 590
Gln Arg Phe Leu Pro Asn Pro Asp Gly Leu Gln Pro Gln Asp Pro Glu
        595                 600                 605
Phe Gln Ala Ser Asn Ile Met His Ser Ile Asn Gly Tyr Val Phe Asp
    610                 615                 620
Ser Leu Gln Leu Ser Val Cys Leu His Glu Val Ala Tyr Trp Tyr Ile
625                 630                 635                 640
Leu Ser Val Gly Ala Gln Thr Asp Phe Leu Ser Val Phe Phe Ser Gly
                645                 650                 655
Tyr Thr Phe Lys His Lys Met Val Tyr Glu Asp Thr Leu Thr Leu Phe
                660                 665                 670
```

```
Pro Phe Ser Gly Glu Thr Val Phe Met Ser Met Glu Asn Pro Gly Leu
            675                 680                 685

Trp Val Leu Gly Cys His Asn Ser Asp Leu Arg Asn Arg Gly Met Thr
        690                 695                 700

Ala Leu Leu Lys Val Tyr Ser Cys Asp Arg Asp Ile Gly Asp Tyr Tyr
705                 710                 715                 720

Asp Asn Thr Tyr Glu Asp Ile Pro Gly Phe Leu Leu Ser Gly Lys Asn
                725                 730                 735

Val Ile Glu Pro Arg Ser Phe Ala Gln Asn Ser Arg Pro Pro Ser Ala
            740                 745                 750

Ser Gln Lys Gln Phe Gln Thr Ile Thr Ser Pro Glu Asp Asp Val Glu
        755                 760                 765

Leu Asp Pro Gln Ser Gly Glu Arg Thr Gln Ala Leu Glu Glu Leu Ser
    770                 775                 780

Val Pro Ser Gly Asp Gly Ser Met Leu Leu Gly Gln Asn Pro Ala Pro
785                 790                 795                 800

His Gly Ser Ser Ser Asp Leu Gln Glu Ala Arg Asn Glu Ala Asp
                805                 810                 815

Asp Tyr Leu Pro Gly Ala Arg Glu Arg Asn Thr Ala Pro Ser Ala Ala
            820                 825                 830

Ala Arg Leu Arg Pro Glu Leu His His Ser Ala Glu Arg Val Leu Thr
835                 840                 845

Pro Glu Pro Glu Lys Glu Leu Lys Lys Leu Asp Ser Lys Met Ser Ser
    850                 855                 860

Ser Ser Asp Leu Leu Lys Thr Ser Pro Thr Ile Pro Ser Asp Thr Leu
865                 870                 875                 880

Ser Ala Glu Thr Glu Arg Thr His Ser Leu Gly Pro Pro His Pro Gln
                885                 890                 895

Val Asn Phe Arg Ser Gln Leu Gly Ala Ile Val Leu Gly Lys Asn Ser
            900                 905                 910

Ser His Phe Ile Gly Ala Gly Val Pro Leu Gly Ser Thr Glu Glu Asp
        915                 920                 925

His Glu Ser Ser Leu Gly Glu Asn Val Ser Pro Val Glu Ser Asp Gly
    930                 935                 940

Ile Phe Glu Lys Glu Arg Ala His Gly Pro Ala Ser Leu Thr Lys Asp
945                 950                 955                 960

Asp Val Leu Phe Lys Val Asn Ile Ser Leu Val Lys Thr Asn Lys Ala
                965                 970                 975

Arg Val Tyr Leu Lys Thr Asn Arg Lys Ile His Ile Asp Asp Ala Ala
            980                 985                 990

Leu Leu Thr Glu Asn Arg Ala Ser Ala Thr Phe Met Asp Lys Asn Thr
        995                 1000                1005

Thr Ala Ser Gly Leu Asn His Val Ser Asn Trp Ile Lys Gly Pro Leu
    1010                1015                1020

Gly Lys Asn Pro Leu Ser Ser Glu Arg Gly Pro Ser Pro Glu Leu Leu
1025                1030                1035                1040

Thr Ser Ser Gly Ser Gly Lys Ser Val Lys Gly Gln Ser Ser Gly Gln
                1045                1050                1055

Gly Arg Ile Arg Val Ala Val Glu Glu Glu Leu Ser Lys Gly Lys
            1060                1065                1070

Glu Met Met Leu Pro Asn Ser Glu Leu Thr Phe Leu Thr Asn Ser Ala
        1075                1080                1085
```

-continued

```
Asp Val Gln Gly Asn Asp Thr His Ser Gln Gly Lys Lys Ser Arg Glu
        1090                1095               1100
Glu Met Glu Arg Arg Glu Lys Leu Val Gln Glu Lys Val Asp Leu Pro
1105                1110                1115                1120
Gln Val Tyr Thr Ala Thr Gly Thr Lys Asn Phe Leu Arg Asn Ile Phe
                1125                1130                1135
His Gln Ser Thr Glu Pro Ser Val Glu Gly Phe Asp Gly Gly Ser His
                1140                1145                1150
Ala Pro Val Pro Gln Asp Ser Arg Ser Leu Asn Asp Ser Ala Glu Arg
                1155                1160                1165
Ala Glu Thr His Ile Ala His Phe Ser Ala Ile Arg Glu Glu Ala Pro
                1170                1175                1180
Leu Glu Ala Pro Gly Asn Arg Thr Gly Pro Gly Pro Arg Ser Ala Val
1185                1190                1195                1200
Pro Arg Arg Arg Val Lys Gln Ser Leu Lys Gln Ile Arg Leu Pro Leu
                1205                1210                1215
Glu Glu Ile Lys Pro Glu Arg Gly Val Val Leu Asn Ala Thr Ser Thr
                1220                1225                1230
Arg Trp Ser Glu Ser Ser Pro Ile Leu Gln Gly Ala Lys Arg Asn Asn
                1235                1240                1245
Leu Ser Leu Pro Phe Leu Thr Leu Glu Met Ala Gly Gly Gln Gly Lys
                1250                1255                1260
Ile Ser Ala Leu Gly Lys Ser Ala Ala Gly Pro Leu Ala Ser Gly Lys
1265                1270                1275                1280
Leu Glu Lys Ala Val Leu Ser Ser Ala Gly Leu Ser Glu Ala Ser Gly
                1285                1290                1295
Lys Ala Glu Phe Leu Pro Lys Val Arg Val His Arg Glu Asp Leu Leu
                1300                1305                1310
Pro Gln Lys Thr Ser Asn Val Ser Cys Ala His Gly Asp Leu Gly Gln
                1315                1320                1325
Glu Ile Phe Leu Gln Lys Thr Arg Gly Pro Val Asn Leu Asn Lys Val
                1330                1335                1340
Asn Arg Pro Gly Arg Thr Pro Ser Lys Leu Leu Gly Pro Pro Met Pro
1345                1350                1355                1360
Lys Glu Trp Glu Ser Leu Glu Lys Ser Pro Lys Ser Thr Ala Leu Arg
                1365                1370                1375
Thr Lys Asp Ile Ile Ser Leu Pro Leu Asp Arg His Glu Ser Asn His
                1380                1385                1390
Ser Ile Ala Ala Lys Asn Glu Gly Gln Ala Glu Thr Gln Arg Glu Ala
                1395                1400                1405
Ala Trp Thr Lys Gln Gly Gly Pro Gly Arg Leu Cys Ala Pro Lys Pro
                1410                1415                1420
Pro Val Leu Arg Arg His Gln Arg Asp Ile Ser Leu Pro Thr Phe Gln
1425                1430                1435                1440
Pro Glu Glu Asp Lys Met Asp Tyr Asp Ile Phe Ser Thr Glu Thr
                1445                1450                1455
Lys Gly Glu Asp Phe Asp Ile Tyr Gly Glu Asp Glu Asn Gln Asp Pro
                1460                1465                1470
Arg Ser Phe Gln Lys Arg Thr Arg His Tyr Phe Ile Ala Ala Val Glu
                1475                1480                1485
Gln Leu Trp Asp Tyr Gly Met Ser Glu Ser Pro Arg Ala Leu Arg Asn
                1490                1495                1500
Arg Ala Gln Asn Gly Glu Val Pro Arg Phe Lys Lys Val Val Phe Arg
```

-continued

```
        1505                1510                1515                1520

Glu Phe Ala Asp Gly Ser Phe Thr Gln Pro Ser Tyr Arg Gly Glu Leu
                1525                1530                1535

Asn Lys His Leu Gly Leu Leu Gly Pro Tyr Ile Arg Ala Glu Val Asp
                1540                1545                1550

Asn Ile Met Val Thr Phe Lys Asn Gln Ala Ser Arg Pro Tyr Ser Phe
                1555                1560                1565

Tyr Ser Ser Leu Ile Ser Tyr Pro Asp Asp Gln Glu Gln Gly Ala Glu
                1570                1575                1580

Pro Arg His Asn Phe Val Gln Pro Asn Glu Thr Arg Thr Tyr Phe Trp
1585                1590                1595                1600

Lys Val Gln His His Met Ala Pro Thr Glu Asp Glu Phe Asp Cys Lys
                1605                1610                1615

Ala Trp Ala Tyr Phe Ser Asp Val Asp Leu Glu Lys Asp Val His Ser
                1620                1625                1630

Gly Leu Ile Gly Pro Leu Leu Ile Cys Arg Ala Asn Thr Leu Asn Ala
                1635                1640                1645

Ala His Gly Arg Gln Val Thr Val Gln Glu Phe Ala Leu Phe Phe Thr
                1650                1655                1660

Ile Phe Asp Glu Thr Lys Ser Trp Tyr Phe Thr Glu Asn Val Glu Arg
1665                1670                1675                1680

Asn Cys Arg Ala Pro Cys His Leu Gln Met Glu Asp Pro Thr Leu Lys
                1685                1690                1695

Glu Asn Tyr Arg Phe His Ala Ile Asn Gly Tyr Val Met Asp Thr Leu
                1700                1705                1710

Pro Gly Leu Val Met Ala Gln Asn Gln Arg Ile Arg Trp Tyr Leu Leu
                1715                1720                1725

Ser Met Gly Ser Asn Glu Asn Ile His Ser Ile His Phe Ser Gly His
                1730                1735                1740

Val Phe Ser Val Arg Lys Lys Glu Glu Tyr Lys Met Ala Val Tyr Asn
1745                1750                1755                1760

Leu Tyr Pro Gly Val Phe Glu Thr Val Glu Met Leu Pro Ser Lys Val
                1765                1770                1775

Gly Ile Trp Arg Ile Glu Cys Leu Ile Gly Glu His Leu Gln Ala Gly
                1780                1785                1790

Met Ser Thr Thr Phe Leu Val Tyr Ser Lys Glu Cys Gln Ala Pro Leu
                1795                1800                1805

Gly Met Ala Ser Gly Arg Ile Arg Asp Phe Gln Ile Thr Ala Ser Gly
                1810                1815                1820

Gln Tyr Gly Gln Trp Ala Pro Lys Leu Ala Arg Leu His Tyr Ser Gly
1825                1830                1835                1840

Ser Ile Asn Ala Trp Ser Thr Lys Asp Pro His Ser Trp Ile Lys Val
                1845                1850                1855

Asp Leu Leu Ala Pro Met Ile Ile His Gly Ile Met Thr Gln Gly Ala
                1860                1865                1870

Arg Gln Lys Phe Ser Ser Leu Tyr Ile Ser Gln Phe Ile Ile Met Tyr
                1875                1880                1885

Ser Leu Asp Gly Arg Asn Trp Gln Ser Tyr Arg Gly Asn Ser Thr Gly
                1890                1895                1900

Thr Leu Met Val Phe Phe Gly Asn Val Asp Ala Ser Gly Ile Lys His
1905                1910                1915                1920

Asn Ile Phe Asn Pro Pro Ile Val Ala Arg Tyr Ile Arg Leu His Pro
                1925                1930                1935
```

```
Thr His Tyr Ser Ile Arg Ser Thr Arg Leu Met Glu Leu Met Gly Cys
            1940                1945                1950

Asp Leu Asn Ser Cys Ser Met Pro Leu Gly Met Gln Asn Lys Ala Ile
        1955                1960                1965

Ser Asp Ser Gln Ile Thr Ala Ser Ser His Leu Ser Asn Ile Phe Ala
    1970                1975                1980

Thr Trp Ser Pro Ser Gln Ala Arg Leu His Leu Gln Gly Arg Thr Asn
1985                1990                1995                2000

Ala Trp Arg Pro Arg Val Ser Ser Ala Glu Glu Trp Leu Gln Val Asp
                2005                2010                2015

Leu Gln Lys Thr Val Lys Val Thr Gly Ile Thr Thr Gln Gly Val Lys
            2020                2025                2030

Ser Leu Leu Ser Ser Met Tyr Val Lys Glu Phe Leu Val Ser Ser Ser
        2035                2040                2045

Gln Asp Gly Arg Arg Trp Thr Leu Phe Leu Gln Asp Gly His Thr Lys
    2050                2055                2060

Val Phe Gln Gly Asn Gln Asp Ser Ser Thr Pro Val Val Asn Ala Leu
2065                2070                2075                2080

Asp Pro Pro Leu Phe Thr Arg Tyr Leu Arg Ile His Pro Thr Ser Trp
                2085                2090                2095

Ala Gln His Ile Ala Leu Arg Leu Glu Val Leu Gly Cys Glu Ala Gln
            2100                2105                2110

Asp Leu Tyr
        2115

<210> SEQ ID NO 6
<211> LENGTH: 21
<212> TYPE: DNA
<213> ORGANISM: Synthetic oligonucleotide

<400> SEQUENCE: 6
ccgcgtagga ccattgttca a                                         21

<210> SEQ ID NO 7
<211> LENGTH: 21
<212> TYPE: DNA
<213> ORGANISM: Synthetic oligonucleotide

<400> SEQUENCE: 7
gggagctaaa gatattttag a                                         21

<210> SEQ ID NO 8
<211> LENGTH: 20
<212> TYPE: DNA
<213> ORGANISM: Synthetic oligonucleotide

<400> SEQUENCE: 8
ggctccaatg aggtctgaat                                           20

<210> SEQ ID NO 9
<211> LENGTH: 20
<212> TYPE: DNA
<213> ORGANISM: Synthetic oligonucleotide

<400> SEQUENCE: 9
gctggtctga tcctcatact                                           20

<210> SEQ ID NO 10
```

```
<211> LENGTH: 19
<212> TYPE: DNA
<213> ORGANISM: Synthetic oligonucleotide

<400> SEQUENCE: 10
gccaccagaa gatactacc                                              19

<210> SEQ ID NO 11
<211> LENGTH: 21
<212> TYPE: DNA
<213> ORGANISM: Synthetic oligonucleotide

<400> SEQUENCE: 11
tttataactt ctgtcatcgg g                                           21

<210> SEQ ID NO 12
<211> LENGTH: 21
<212> TYPE: DNA
<213> ORGANISM: Synthetic oligonucleotide

<400> SEQUENCE: 12
ccaggctgag gtttatgata c                                           21

<210> SEQ ID NO 13
<211> LENGTH: 20
<212> TYPE: DNA
<213> ORGANISM: Synthetic oligonucleotide

<400> SEQUENCE: 13
ctcctctcag cagcattata                                             20

<210> SEQ ID NO 14
<211> LENGTH: 20
<212> TYPE: DNA
<213> ORGANISM: Synthetic oligonucleotide

<400> SEQUENCE: 14
ttgcctagtg ctagggtgtc                                             20

<210> SEQ ID NO 15
<211> LENGTH: 21
<212> TYPE: DNA
<213> ORGANISM: Synthetic oligonucleotide

<400> SEQUENCE: 15
gccaagaagc atcctaaaac t                                           21

<210> SEQ ID NO 16
<211> LENGTH: 21
<212> TYPE: DNA
<213> ORGANISM: Synthetic oligonucleotide

<400> SEQUENCE: 16
tcttgaattc tgggagaagc t                                           21

<210> SEQ ID NO 17
<211> LENGTH: 21
<212> TYPE: DNA
<213> ORGANISM: Synthetic oligonucleotide

<400> SEQUENCE: 17
ggcattgatt gatccggaat a                                           21
```

```
<210> SEQ ID NO 18
<211> LENGTH: 20
<212> TYPE: DNA
<213> ORGANISM: Synthetic oligonucleotide

<400> SEQUENCE: 18
aaaggctgtg ctctcaaaac                                              20

<210> SEQ ID NO 19
<211> LENGTH: 21
<212> TYPE: DNA
<213> ORGANISM: Synthetic oligonucleotide

<400> SEQUENCE: 19
ccactgtcca tattgtcctg a                                            21

<210> SEQ ID NO 20
<211> LENGTH: 21
<212> TYPE: DNA
<213> ORGANISM: Synthetic oligonucleotide

<400> SEQUENCE: 20
ctccacggta taagggctga g                                            21

<210> SEQ ID NO 21
<211> LENGTH: 21
<212> TYPE: DNA
<213> ORGANISM: Synthetic oligonucleotide

<400> SEQUENCE: 21
cagtggagcg tctctgggat t                                            21

<210> SEQ ID NO 22
<211> LENGTH: 20
<212> TYPE: DNA
<213> ORGANISM: Synthetic oligonucleotide

<400> SEQUENCE: 22
atattgtcct gaagctgtaa                                              20

<210> SEQ ID NO 23
<211> LENGTH: 17
<212> TYPE: DNA
<213> ORGANISM: Synthetic oligonucleotide

<400> SEQUENCE: 23
tcggcgagca cctgcaa                                                 17

<210> SEQ ID NO 24
<211> LENGTH: 17
<212> TYPE: DNA
<213> ORGANISM: Synthetic oligonucleotide

<400> SEQUENCE: 24
acagcccaag agctcca                                                 17

<210> SEQ ID NO 25
<211> LENGTH: 24
<212> TYPE: DNA
<213> ORGANISM: Synthetic oligonucleotide

<400> SEQUENCE: 25
gccgggatga gcactctgtt tctg                                         24
```

<210> SEQ ID NO 26
<211> LENGTH: 21
<212> TYPE: DNA
<213> ORGANISM: Synthetic oligonucleotide

<400> SEQUENCE: 26
ttgactgctg gagatgagga a								21

<210> SEQ ID NO 27
<211> LENGTH: 21
<212> TYPE: DNA
<213> ORGANISM: Synthetic oligonucleotide

<400> SEQUENCE: 27
gcacccaacc cattacagca t								21

<210> SEQ ID NO 28
<211> LENGTH: 18
<212> TYPE: DNA
<213> ORGANISM: Synthetic oligonucleotide

<400> SEQUENCE: 28
gcagcccaga acctccat								18

<210> SEQ ID NO 29
<211> LENGTH: 20
<212> TYPE: DNA
<213> ORGANISM: Synthetic oligonucleotide

<400> SEQUENCE: 29
ggggtgaaat ctctcctcat								20

<210> SEQ ID NO 30
<211> LENGTH: 21
<212> TYPE: DNA
<213> ORGANISM: Synthetic oligonucleotide

<400> SEQUENCE: 30
cctccagcct cagagcaatt t								21

<210> SEQ ID NO 31
<211> LENGTH: 21
<212> TYPE: DNA
<213> ORGANISM: Synthetic oligonucleotide

<400> SEQUENCE: 31
ttgatgatta ttatgaggac a								21

<210> SEQ ID NO 32
<211> LENGTH: 21
<212> TYPE: DNA
<213> ORGANISM: Synthetic oligonucleotide

<400> SEQUENCE: 32
aggcaaaact acattctctt g								21

<210> SEQ ID NO 33
<211> LENGTH: 21
<212> TYPE: DNA
<213> ORGANISM: Synthetic oligonucleotide

<400> SEQUENCE: 33
ggtggtagta ggagaggatg a								21

<210> SEQ ID NO 34
<211> LENGTH: 21
<212> TYPE: DNA
<213> ORGANISM: Synthetic oligonucleotide

<400> SEQUENCE: 34
tatttccctt tgatggtgtt t                                              21

<210> SEQ ID NO 35
<211> LENGTH: 20
<212> TYPE: DNA
<213> ORGANISM: Synthetic oligonucleotide

<400> SEQUENCE: 35
aaaggctgtg ctctcaaaac                                                20

<210> SEQ ID NO 36
<211> LENGTH: 22
<212> TYPE: DNA
<213> ORGANISM: Synthetic oligonucleotide

<400> SEQUENCE: 36
actcatccca taaatcccag ag                                             22

<210> SEQ ID NO 37
<211> LENGTH: 21
<212> TYPE: DNA
<213> ORGANISM: Synthetic oligonucleotide

<400> SEQUENCE: 37
ctggagaagc aaaaggttaa t                                              21

<210> SEQ ID NO 38
<211> LENGTH: 21
<212> TYPE: DNA
<213> ORGANISM: Synthetic oligonucleotide

<400> SEQUENCE: 38
ctggagaagc aaaaggttaa t                                              21

<210> SEQ ID NO 39
<211> LENGTH: 21
<212> TYPE: DNA
<213> ORGANISM: Synthetic oligonucleotide

<400> SEQUENCE: 39
ctggctcagg agtaaattct c                                              21

<210> SEQ ID NO 40
<211> LENGTH: 25
<212> TYPE: DNA
<213> ORGANISM: Synthetic oligonucleotide

<400> SEQUENCE: 40
ccagttgaac attttctaga aatac                                          25

<210> SEQ ID NO 41
<211> LENGTH: 26
<212> TYPE: DNA
<213> ORGANISM: Synthetic oligonucleotide

<400> SEQUENCE: 41

-continued ggatctttgc cactcaccac gtcagt                26

<210> SEQ ID NO 42
<211> LENGTH: 28
<212> TYPE: DNA
<213> ORGANISM: Synthetic oligonucleotide

<400> SEQUENCE: 42
ctgagaatgg gaagagggta agtgtgtc              28

<210> SEQ ID NO 43
<211> LENGTH: 21
<212> TYPE: DNA
<213> ORGANISM: Synthetic oligonucleotide

<400> SEQUENCE: 43
gctgtgcatg atgttagaga g                     21

<210> SEQ ID NO 44
<211> LENGTH: 21
<212> TYPE: DNA
<213> ORGANISM: Synthetic oligonucleotide

<400> SEQUENCE: 44 ccaccccaa tgatagaagt c                      21

<210> SEQ ID NO 45
<211> LENGTH: 27
<212> TYPE: DNA
<213> ORGANISM: Synthetic oligonucleotide

<400> SEQUENCE: 45
ctgtgacgga gctctggtct gagactt                27

<210> SEQ ID NO 46
<211> LENGTH: 21
<212> TYPE: DNA
<213> ORGANISM: Synthetic oligonucleotide

<400> SEQUENCE: 46
gttgccatcc agactgtaca t                     21

<210> SEQ ID NO 47
<211> LENGTH: 21
<212> TYPE: DNA
<213> ORGANISM: Synthetic oligonucleotide

<400> SEQUENCE: 47
ccaggcttgt ccgaaacatc t                     21

<210> SEQ ID NO 48
<211> LENGTH: 21
<212> TYPE: DNA
<213> ORGANISM: Synthetic oligonucleotide

<400> SEQUENCE: 48
ctcctgcact gtcacttgtc t                     21

<210> SEQ ID NO 49
<211> LENGTH: 21
<212> TYPE: DNA
<213> ORGANISM: Synthetic oligonucleotide

<400> SEQUENCE: 49

-continued cccagatacc aagtgaagag t                                         21

<210> SEQ ID NO 50
<211> LENGTH: 21
<212> TYPE: DNA
<213> ORGANISM: Synthetic oligonucleotide

<400> SEQUENCE: 50
gcctgagtgc acatctttct c                                         21

<210> SEQ ID NO 51
<211> LENGTH: 24
<212> TYPE: DNA
<213> ORGANISM: Synthetic oligonucleotide

<400> SEQUENCE: 51
cctctcgtcc ctactccttc tatt                                      24

<210> SEQ ID NO 52
<211> LENGTH: 24
<212> TYPE: DNA
<213> ORGANISM: Synthetic oligonucleotide

<400> SEQUENCE: 52
ggatagaggt tgtagactgc catt                                      24

<210> SEQ ID NO 53
<211> LENGTH: 22
<212> TYPE: DNA
<213> ORGANISM: Synthetic oligonucleotide

<400> SEQUENCE: 53
catgggagac aagtgacagt gc                                        22

<210> SEQ ID NO 54
<211> LENGTH: 17
<212> TYPE: DNA
<213> ORGANISM: Synthetic oligonucleotide

<400> SEQUENCE: 54
ccttccgccc gccgcag                                              17

<210> SEQ ID NO 55
<211> LENGTH: 26
<212> TYPE: DNA
<213> ORGANISM: Synthetic oligonucleotide

<400> SEQUENCE: 55
ctggcttagt aatggctcag gatcaa                                    26

<210> SEQ ID NO 56
<211> LENGTH: 21
<212> TYPE: DNA
<213> ORGANISM: Synthetic oligonucleotide

<400> SEQUENCE: 56
ttgactgctg gagatgagga a                                         21

<210> SEQ ID NO 57
<211> LENGTH: 19
<212> TYPE: DNA
<213> ORGANISM: Synthetic oligonucleotide
<210> SEQ ID NO 58
<211> LENGTH: 23
<212> TYPE: DNA
<213> ORGANISM: Synthetic oligonucleotide

<400> SEQUENCE: 58
ggagacctca ggcaaataac cca                    23

<210> SEQ ID NO 59
<211> LENGTH: 20
<212> TYPE: DNA
<213> ORGANISM: Synthetic oligonucleotide

<400> SEQUENCE: 59
gttcgagacg gttccgcaca                        20

<210> SEQ ID NO 60
<211> LENGTH: 21
<212> TYPE: DNA
<213> ORGANISM: Synthetic oligonucleotide

<400> SEQUENCE: 60
ctgtgcggaa ccgtctcgaa c                      21

<210> SEQ ID NO 61
<211> LENGTH: 17
<212> TYPE: DNA
<213> ORGANISM: Synthetic oligonucleotide

<400> SEQUENCE: 61
agacctcgct gtcggcc                           17

<210> SEQ ID NO 62
<211> LENGTH: 206
<212> TYPE: DNA
<213> ORGANISM: Canis familiaris

<400> SEQUENCE: 62
aaggaaacaa tcttatctgt tgctgcctac tgccaatgct gctgtaacat ccagcaggta    60
aaggtcccta acattcacag caacagttgt gggacttttc atgaaatcat agaaaatttg   120
ccttttttct cctgggagct gaagatattt tagggaagaa ttaatctctt gtttctccag   180
ttgaacattt tctagcaata cgagcc                                       206

<210> SEQ ID NO 63
<211> LENGTH: 1526
<212> TYPE: DNA
<213> ORGANISM: Canis familiaris

<400> SEQUENCE: 63
cccgcgcctc tgcggccctg tctccctgc ctccctgccc tgtcccgcg gcttccggg     60 ccctgacccc cacctctcca gcctgtcccc gtggcctcct gggccctgtg ccccacctc   120 cccgccctgt cccccacct ccccggcctt gtccccac ctcccggcc ctgccccctg     180 tccccaagt gctcccacgt tcgccttcc ctccgcggc tgaggcgag gccgcacccc    240 atctggaagg cgtcctccgg ccgacagcga ggtctgtcgc gcagcccac gtcctctgtg  300 cagtgaccgc gtctgcggcg ggcggaaggt atccgggatg tgggagtccg gtctgggtac  360

<400> SEQUENCE: 57
cgcgggacag ggcagggag                         19

```
ctggggagta aaggccccgc ttgccgtcgg cgccgcgaag cccggagcga gcaggccgat    420
ctgggcctcc ctgtagacgc ggtcataggt ccgtgtcctc gtcttcgggg ctcaggaagg    480
gcgacgaccg tagcaggcct cactgggacc ccacgcccac cggggccgag gggaccggag    540
gccgggagga cccgaagtct gcgacccacg gccgcgtcca cggggttcct ggtgcaagag    600
gacaggcctt acactcccac gagacgcgag gaaatcgatg cttttccccc gaactagagc    660
acttcgtggc gaccgtgctg gcgctgctgt gacctcctgg gaaggcagcc cggctgccgc    720
gggggatcgc ggagcagcgg gggcaggtgc acacgttagg gcggatgcac agaggtcggt    780
aactggcttc cccgagcagc ccgggaggca agcggccccc ggaggcgacg tggttctatt    840 tcctgcaaa ggtcagccac cctgctctct cttaatgacc ctgctctgga attcctgtgc     900
tatgggccag atacaccaat ttctgaaatg ctcttggatc tgaaatgccc tttggccctc    960
ctgccgcttt cctccatgat tgctcacata aaaccttgac acacgcacag ccgccttcaa   1020
cagatgtagt ttcacactgg aaataaaaat gtgaacagcg atcttcgtgc ggatgcgctg   1080
aatcgcagga tggacacttt agaaatccga attagtgagt caggaaccag actaaactga   1140
actcagagta gaaagtgaga tcatttatga gaggtaaaaa aaaaaaaaaa attaaattaa   1200
aatggagcct tgatccagga taagacttca tagaaggcaa gagactgaaa aagaaatggg   1260
gggtgcagga tgagtaagtt ctagaactct ctgccgacgc tcttgtgccc ggggtgagca   1320
acactgcctt gggcaccgca gaatgccaca ggctgagcta tgcgaagtgc tctaaccagg   1380
ataaaaattg aaagttgcca agaggaagat cacacattgg atgtggtcaa ataaaacaag   1440
aggaaaaaat ttctttggga tgaaattaca ataatgatca tcaaacaaat tagaatcctc   1500
agatcagagt ctcttagtgc aaagcg                                        1526
```

CANINE FACTOR VIII GENE, PROTEIN AND METHODS OF USE

CROSS REFERENCE TO RELATED APPLICATIONS

The present application is a continuation-in-part of U.S application Ser. No. 09/035,141, filed Mar. 5, 1998, now abandoned which claims the benefit of the filing date of U.S. Provisional Application No. 60/039,953, filed Mar. 6, 1997, the disclosures of which are incorporated herein by reference in their entireties.

BACKGROUND OF THE INVENTION

1. Field of the Invention

The present invention is in the fields of molecular biology and gene therapy. In particular, the invention provides isolated nucleic acid molecules encoding canine factor VIII and mutants, fragments or derivatives thereof. The invention also provides canine factor VIII polypeptides encoded by such isolated nucleic acid molecules, antibodies binding to such polypeptides, genetic constructs comprising such nucleic acid molecules, prokaryotic or eukaryotic host cells or whole animals comprising such genetic constructs, and methods and compositions for use in diagnosing disorders characterized by factor VIII deficiency, and therapeutic methods for treating diseases characterized by factor VIII deficiency.

2. Related Art

Overview

Factor VIII of the blood coagulation cascade is a trace plasma glycoprotein that participates as an essential co-factor in the middle phase of the intrinsic pathway of hemostasis. In humans, the protein is synthesized predominantly in hepatocytes although expression of the protein has also been documented in kidney, spleen and lymphoid tissue (Wion, K. D., et al., *Nature* 317:726–728 (1985)). In plasma, factor VIII circulates in a bimolecular complex with the multimeric protein von Willebrand factor (Hoyer, L. W.,*Blood* 58:1–13 (1981); Fay, P. J., and Smudzin, T. M.,*J. Biol. Chem.* 265:6197–6202 (1990)), which protects it from proteolytic degradation by the natural anticoagulant factor, Protein C (Fay, P. J., and Walker, F. J., *Biochim. Biophys. Acta* 994:142–148 (1989)). Mutations in the gene that encodes factor VIII result in the X-linked inherited bleeding disorder, hemophilia A (Classic Hemophilia) (Hoyer, L. W., *New Engl. J. Med.* 330:38–47 (1994)).

The Human Factor VIII Protein

As alluded to above, factor VIII is synthesized in a variety of cellular sites including the liver, spleen and kidney (Wion, K. D., et al., *Nature* 317:726–728 (1985)). The most dramatic evidence of the involvement of hepatocytes in this process is the documentation of cures of hemophilic bleeding following liver transplantation (Lewis, J. H., et al., *N. Engl. J. Med.* 312:1189–1190 (1985)). In addition, evidence of factor VIII reconstitution following the transplantation of normal spleens into hemophilic dogs indicates that cells within this organ also play an important role in factor VIII synthesis (Webster, W. P., et al., *N.C. Med. J.* 28:505–507 (1967); Norman, J. C., et al., *Surgery* 64:1–16 (1968)).

In humans, factor VIII circulates in the plasma as a series of N-terminal heavy chain/C-terminal light chain heterodimers that are linked by a cationic bridge. The molecular weight of these complexes varies between ~300 kD and ~200 kD as a result of varying degrees of proteolysis of the central B domain of the protein.

The primary translation product encoded by the human factor VIII gene is a 2351 amino acid protein with a typical 19 residue N-terminal signal sequence (Wood, W. I., et al., *Nature* 312:330–336 (1984)). The sequence of the 2332 residue secreted human protein (SEQ ID NO:3) comprises three large tandem repeats of ~350 amino acids (domains A1, A2 and A3) (Fass, D. N., et al., *Proc. Natl. Acad. Sci. USA* 82:1688–1691 (1985)). The amino terminal A1 and A2 domains are separated from the C-terminal A3 domain by the 980-residue B domain. Recombinant human factor VIII molecules from which the B domain has been deleted maintain full factor VIII cofactor activity and circulate in plasma with a normal half-life (Pittman, D. D., et al., *Blood* 81:2925–2935 (1993); Lind, P., et al., *Eur. J. Biochem.* 232:19–27 (1995)).

In plasma, human factor VIII is activated through the cleavage of two Arg-Ser bonds (Arg 372-Ser 373 in the N-terminal heavy chain and Arg 1689-Ser 1690 in the light chain) by the serine protease thrombin (Eaton, D., et al, *Biochemistry* 25:1986–1990 (1986); Pittman, D. D., and Kaufman, R. J., *Proc. Natl. Acad. Sci. USA* 85:2429–2433 (1988)). These same cleavages can be effected by activated factor X. A third peptide bond (Arg 740-Ser 741) is cleaved to release the B domain of the protein. Inactivation of human factor VIII cofactor activity is achieved by activated Protein C cleavage at Arg 336-Met 337 (Fay P. J., and Walker, F. J., *Biochim. Biophys. Acta* 994:142–148 (1989); Eaton, D., et al., *Biochemistry* 25:1986–1990 (1986)).

The other area of human factor VIII structure/function that has been explored extensively, relates to its interaction with von Willebrand factor (VWF). The binding site for VWF on human factor VIII is on the factor VIII light chain between residues Val 1670-Glu 1684 (Foster, P. A., et al.,*J. Biol. Chem.* 263:5230–5234 (1988)). Post-translational sulfation of Tyr 1680 is critical to this process (Pittman, D. D., et al, *Biochemistry* 31:3315–3325 (1992)), and thrombin- or factor Xa-induced cleavage of Arg 1689-Ser 1690 will release VWF from human factor VIII.

The Human Factor VIII Gene

The gene that encodes human factor VIII is located on the long arm of the X chromosome close to the telomere, at cytogenetic band Xq28. The gene was cloned and characterized in 1984 by groups from the two American biotechnology companies Genentech and Genetics Institute (Gitschier, J., et al.,*Nature* 312:326–330 (1984); Toole, J. J., *Nature* 312:342–347 (1984)). The human gene spans 186 kilobases of DNA and comprises 26 exons ranging in size from 69 basepairs (exon 5) to 3.1 kbp (exon 14). All the invariant splice donor and acceptor splice sites conform to the 5'GT/AG 3' rule, and remaining splice consensus sequences are in general agreement with other reported nucleotide frequencies.

THe human gene has 171 nucleotides (nts) of 5' untranslated sequence and 1,805 nucleotides of 3' UTR. In the 5' upstream region, a GATAAA sequence at nt −30 from the transcriptional start site likely represents an alternative TATA element. Preliminary studies of the human factor VIII promoter indicate that there are at least 12 cis-acting elements in the 1 kb of sequence upstream of the mRNA start site (Figueiredo, M. S., and Brownlee, G. G.,*J. Biol. Chem.* 270:11828–11838 (1995); McGlynn, L. K., et al., *Mol. Cell. Biol.* 16:1936–1942 (1996)).

Molecular Genetic Pathology of Human Factor VIII

Two types of sequence changes have been found in the human factor VIII gene: neutral polymorphic changes, and mutations that result in functional factor VIII deficiency.

Human Factor VIII Polymorphisms

To date, nine nucleotide polymorphisms have been documented within or adjacent to the human factor VIII sequence (Peake, I., *Thromb. Haemost.* 67:277–280 (1992); Peake, I. R., et al., *Bull. World Health Org.* 71:429–458 (1993)). Seven of these sequence changes represent single nucleotide alterations demonstrable either by changes in restriction fragment length patterns or by allele specific oligonucleotide hybridization. The remaining two polymorphisms in introns 13 and 22 are examples of CA microsatellite repeats that demonstrate heterozygosity in >70% of individuals (Lalloz, M. R. A., et al., *Lancet* 338:207–211 (1991); Windsor, S., et al., *Br. J. Haematol.* 86:810–815 (1994)). The analysis of human factor VIII polymorphisms continues to represent an important component of genetic studies for carrier testing and prenatal diagnosis in families in which hemophilia A is segregating (Peake, I. R., et al., *Bull. World Health Org.* 71:429–458 (1993)).

Human Factor VIII Mutations

Mutations within the human factor VIII gene give rise to the X-linked bleeding disorder hemophilia A. This disease has a population incidence of ~1 in 10,000 males and represents the most common severe inherited bleeding disorder known in humans (Hoyer, L. W., *New Engl. J. Med.* 330:38–47 (1994)).

To date over 300 different human factor VIII mutations have been documented in patients with hemophilia A. As with other diseases in which widespread interest has been generated in molecular genetic pathology, a worldwide hemophilia A mutation database has been established to which all new human mutations are submitted (Tuddenham, E. G., et al., *Nucl. Acids Res.* 22:3511–3533 (1994)). A review of this database (available via Internet at http://146.179.66.63/usr/www/WebPages/main.dir/main.htm) shows that the majority of the mutations causing this disease are single nucleotide substitutions (total of 183 unique changes) distributed throughout the human factor VIII coding sequence. Many different gene deletions (117) and insertions (12) have also been documented.

Factor VIII in Other Species

Interest in the factor VIII molecule in species other than humans relates to two phenomena. First, spontaneously occurring hemophilia A has been identified in several other species including the dog (Graham, J. B., et al., *J. Exp. Med.* 90:97–111 (1949); Stormorken, H., et al., *Scand. J. Haematol.* 2:174–178 (1965); Giles, A. R., et al., *Blood* 60:727 (1982)), sheep (Neuenschwander, S., et al., *Thromb. Haemost* 68:618–620 (1992)), and horse (Archer, R. K., *Vet. Rec.* 73:338–341 (1961); Archer, R. K., and Allen, B. V., *Vet. Rec.* 91:655–661 (1972)). Second, recent results have indicated great potential in studying human gene therapy strategies in an animal model.

Despite this interest in factor VIII in non-human animals, however, primary sequences of factor VIII are only available for two other species: the mouse (SEQ ID NO:4) (Elder, B., et al., *Genomics* 16:374–379 (1993)) and the pig (SEQ ID NO:5) (Toole, J. J., et al., *Proc. Natl. Acad. Sci. USA* 83:5939–5942 (1986)). The complete porcine cDNA sequence obtained from PCR amplification of factor VIII sequences from a pig spleen cDNA library has recently been reported Healey, J. F., et al., *Blood* 88:4209–4214 (1996)).

A genomic fragment encoding the entire exon 14 and part of exon 15 of porcine factor VIII has been isolated, and the amino acid sequence of this region of the protein deduced (Toole, J. J., et al., *Proc. Natl. Acad. Sci. USA* 83:5939–5942 (1986)). These results showed a marked contrast between the level of amino acid sequence identity between the porcine and human sequences in the B domain (~50% sequence identity and the remainder of the protein (approaching 85% sequence identity). In addition, the porcine B domain shows deletions of over 200 amino acids when compared to the human protein.

The murine factor VIII cDNA sequence has also been reported (Elder, B., et al., *Genomics* 16:374–379 (1993)). The 6.9 kb murine factor VIII coding sequence shares 82% sequence identity with the coding sequence of human factor VIII. Outside of the sequence encoding the B domain the sequence identity at the nucleotide level is 88%. At the amino acid level, an overall identity of 74% is present and this figure increases to 87% when only residues outside of the B domain are considered. Amino acid sequence identity for the B domain is significantly lower at 55% for human versus mouse. The residues present at critical sites for factor VIII cleavage are conserved in the mouse sequence and sites for essential post-translational modification are also maintained. Finally, the shorter 7.2 kb factor VIII transcript derived from the mouse gene represents the consequence of a smaller 3' untranslated region in the mouse.

Since the identification of spontaneously occurring hemophilia A in dogs (Graham, J. B., et al., *J. Exp. Med.* 90:97–111 (1949); Stormorken, H., et al., *Scand J. Haematol.* 2:174–178 (1995); Giles, A. R., et as., *Blood* 60:727 (1982), there has been increasing interest in the use of canines as model systems for the study of the physiology of human diseases characterized by factor VIII deficiencies (e.g., hemophilia A). Furthermore, the canine has shown promise as a model system for the development of methods of detecting and treating such diseases in humans.

It would therefore be advantageous to provide compositions comprising isolated nucleic acid molecules encoding canine factor VIII or polypeptides encoded by such nucleic acid molecules, and diagnostic and therapeutic methods for detecting and treating factor VIII deficiencies (spontaneous or induced) in dogs. These methods and compositions would be particularly useful in modeling similar approaches to diagnosis and treatment of human factor VIII deficiencies. The present invention therefore provides such methods and compositions.

SUMMARY OF THE INVENTION

The present invention provides isolated nucleic acid molecules comprising a polynucleotide having the nucleotide sequence shown in FIG. 1 (SEQ ID NO:1). The invention also relates to isolated nucleic acid molecules comprising a polynucleotide encoding the canine factor VIII polypeptide having the amino acid sequence shown in FIG. 1 (SEQ ID NO:2), or the amino acid sequence encoded by the cDNA clone deposited in a bacterial host as pBK-cmV (1-6#23) canine FVIII (ATCC Accession No. 209475).

The present invention also relates to vectors, particularly expression vectors, which comprise the isolated nucleic acid molecules of the present invention, and to host cells comprising these vectors, as well as to methods of making such vectors and host cells and methods of using the same for production of canine factor VIII polypeptides by recombinant techniques.

The invention further provides an isolated canine factor VIII polypeptide having the amino acid sequence encoded by the isolated nucleic acid molecules of the present invention, and canine factor VIII polypeptides produced by the above-described recombinant methods. An additional embodiment of this aspect of the invention relates to a polypeptide having the amino acid sequence of an epitope-bearing portion of a canine factor VIII polypeptide. In another embodiment, the invention provides an isolated antibody, which may be polyclonal or monoclonal, that binds specifically to a canine factor VIII polypeptide of the invention.

The invention also provides methods useful during diagnosis of a canine factor VIII deficiency-dependent bleeding disorder, and methods for treating a canine afflicted with such a disorder. This aspect of the invention includes gene therapy methods wherein an isolated polynucleotide of the invention is incorporated into a vector which is introduced into the cells of the canine, thereby inducing an increase in the expression of canine factor VIII in the canine; such an approach may be done ex vivo or in vivo.

Another preferred such method comprises administering to the dog a pharmaceutical composition comprising a therapeutically effective amount of an isolated canine factor VIII polypeptide of the invention and a pharmaceutically acceptable carrier or excipient therefor.

BRIEF DESCRIPTION OF THE DRAWINGS

FIG. 1 is a depiction of the complete cDNA nucleotide sequence (SEQ ID NO:1) and deduced complete amino acid (SEQ ID NO:2) sequence of canine Factor VIII protein. The protein has an N-terminal hydrophobic signal sequence of 19 amino acid residues (underlined) and a deduced molecular weight of about 257 kDa. The predicted amino acid sequence of the mature canine factor VIII protein is also shown, at amino acid residues 20–2343.

FIG. 2 is a depiction of the aligned amino acid sequences of canine Factor VIII ("DOGLESS I") (SEQ ID NO:2) and corresponding amino acid sequences of Factor VIII proteins from human ("HUMLESS I") (SEQ ID NO:3), mouse ("MOULESS I") (SEQ ID NO:4) and pig ("PIGLESS I") (SEQ ID NO:5), indicating the regions of amino acid sequence identity between the amino acid sequences of the Factor VIII proteins from these species.

FIG. 4 is a line graph depicting the serum levels of anti-canine factor VIII antibodies in two hemophilic canines over a period of 23 days following infusion of the canines with canine factor VIII genetic constructs of invention.

FIG. 5 is a line graph depicting the levels of alanine transaminase activity (in units/ml) in two hemophilic canines over a period of 23 days following infusion of the canines with canine factor VIII genetic constructs of invention.

FIG. 6 is a line graph depicting the whole blood clotting times (in minutes) in two hemophilic canines over a period of 23 days following infusion of the canines with canine factor VIII genetic constructs of invention.

DETAILED DESCRIPTION OF THE INVENTION

Figure 3:
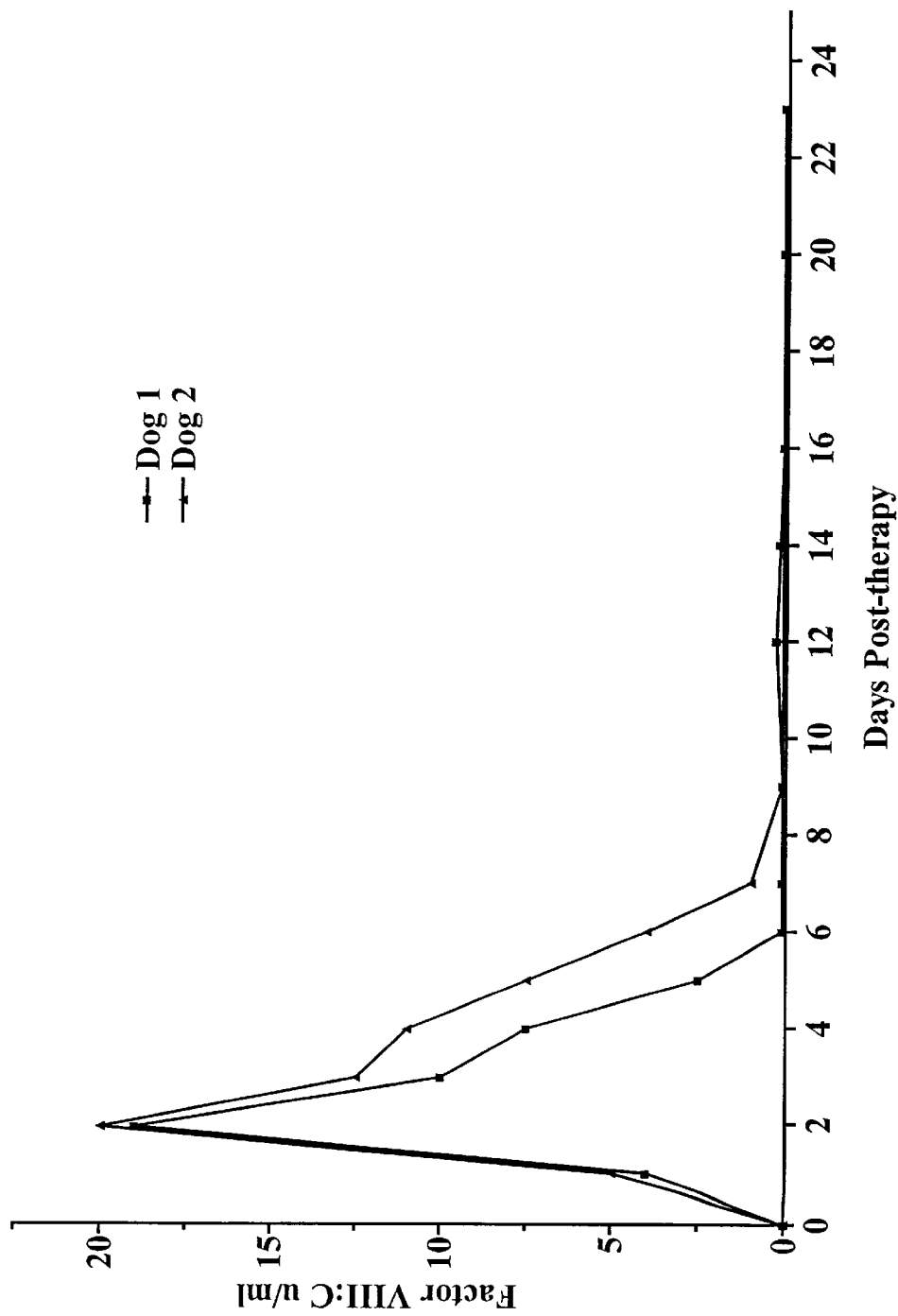
FIG. 3 is a line graph depicting the factor VIII coagulant levels in two hemophilic canines (measured against a human plasma standard) over a period of 23 days following infusion of the canines with canine factor VIII genetic constructs of invention.

The present invention provides isolated nucleic acid molecules comprising a polynucleotide having the nucleotide sequence set forth in FIG. 1 (SEQ ID NO:1), and isolated nucleic acid molecules comprising a polynucleotide encoding a canine factor VIII polypeptide having the amino acid sequence shown in FIG. 1 (SEQ ID NO:2), which was determined by sequencing a cloned cDNA. As used herein, the term "canine" is intended to mean domesticated dogs (Canis familiaris), as well as certain species of feral dogs and related animals such as wolves, foxes, hyenas, jackals, dingoes, etc. The canine factor VIII protein of the present invention shares about 80% overall amino acid sequence identity with the factor VIII proteins of human, mouse and pig (FIG. 2) (SEQ ID NOs:3, 4 and 5, respectively), although the sequence identity varies within individual domains of the protein as described in detail in the Examples below. The nucleotide sequence shown in FIG. 1 (SEQ ID NO:1) was obtained by sequencing a cDNA clone prepared from canine liver total RNA. A clone, designated pBK-cmV (1-6#23) canine FVIII, in which the region encoding amino acids 821 to 1,595 is deleted, was also constructed. This clone was deposited on Nov. 20, 1997, with the American Type Culture Collection (ATCC), 12301 Parklawn Drive, Rockville, Md. 20852 USA, and was given ATCC Accession No. 209475. The deposited canine factor VIII cDNA starts 30 nucleotides upstream of the ATG (methionine) start codon and ends 83 nucleotides downstream of the TGA stop codon. Deleted amino acids 821 to 1,595 correspond to the B-domain. The total size of the construct is 9,342 base pairs.

Nucleic Acid Molecules

Unless otherwise indicated, all nucleotide sequences determined by sequencing a DNA molecule herein were determined using manual DNA sequencing, such as dideoxy sequencing, according to methods that are routine to one of ordinary skill in the art (Sanger, F., and Coulson, A. R., *J. Mol. Biol.* 94:444–448 (1975); Sanger, F., et al., *Proc. Natl. Acad. Sci. USA* 74:5463–5467 (1977)). All amino acid sequences of polypeptides encoded by DNA molecules determined herein were predicted by conceptual translation of a DNA sequence determined as above. Therefore, as is known in the art for any DNA sequence determined by these approaches, any nucleotide sequence determined herein may contain some errors. Nucleotide sequences determined by such methods are typically at least about 90% identical, more typically at least about 95% to at least about 99.9% identical to the actual nucleotide sequence of the sequenced DNA molecule. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Unless otherwise indicated, each "nucleotide sequence" set forth herein is presented as a sequence of deoxyribonucleotides (abbreviated A, G, C and T). However, by "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U). For instance, reference to a canine factor VIII RNA molecule having the sequence of SEQ ID NO:1 set forth using deoxyribonucleotide abbreviations is intended to indicate an RNA molecule having a sequence in which each deoxyribonucleotide A, G or C of SEQ ID NO:1 has been replaced by the corresponding ribonucleotide A, G or C, and each deoxyribonucleotide T has been replaced by a ribonucleotide U.

Using the information provided herein, such as the nucleotide sequence in FIG. 1, a nucleic acid molecule of the present invention encoding a canine factor VIII polypeptide may be obtained using standard cloning and screening procedures, such as those for cloning cDNAs using mRNA as starting material. Preferred such methods include PCR-based cloning methods, such as reverse transcriptase-PCR (RT-PCR) using primers such as those described in the Examples below. Illustrative of the invention, the 3' end of the canine factor VIII coding sequence and the 3' untranslated sequence described in FIG. 1 (SEQ ID NO:1) were discovered in a genomic λ DNA library derived from male beagle whole blood. The canine factor VIII gene was also obtained by concatamerization, according to techniques routine to one of ordinary skill in the art, of RT-PCR-amplified factor VIII fragments obtained from canine liver total RNA. The determined nucleotide sequence of the canine factor VIII cDNA of FIG. 1 (SEQ ID NO:1) contains an open reading frame encoding a protein of 2343 amino acid residues, with an initiation codon at positions 1–3 of the nucleotide sequence in FIG. 1 (SEQ ID NO:1), a predicted N-terminal hydrophobic signal sequence of about 19 amino acid residues (underlined in FIG. 2), and a deduced molecular weight of about 257 kDa. The amino acid sequence of the predicted mature canine factor VIII protein is shown in FIG. 1 (SEQ ID NO:2) from amino acid residue 20 to residue 2343. Overall, the canine factor VIII protein shown in FIG. 1 (SEQ ID NO:2) is about 80% identical in amino acid sequence to factor VIII proteins of human (SEQ ID NO:3), murine (SEQ ID NO:4) and porcine (SEQ ID NO:5) origin (FIG. 2), although this sequence identity varies within the six domains of the proteins as shown below in the Examples.

The present invention also provides the mature form(s) of the canine factor VIII protein of the present invention. Proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein; that is, the cleavage pattern is inherent in the amino acid sequence of the polypeptide. Therefore, the present invention provides a nucleotide sequence encoding a B domain deleted canine factor VIII polypeptide having the amino acid sequence encoded by the deposited cDNA clone designated pBK-cmV (1-6#23) canine FVIII (ATCC Accession No.209475) or having the amino acid sequence depicted in FIG. 1 (SEQ ID NO:2; amino acids from about 20 to about 2343), or by a polynucleotide having a nucleic acid sequence as set forth in FIG. 1 (SEQ ID NO:1). By the mature canine factor VIII polypeptide having the amino acid sequence encoded by the deposited cDNA clone or depicted in FIG. 1 (SEQ ID NO:2; amino acids from about 20 to about 2343), or a polynucleotide having a nucleic acid sequence as set forth in FIG. 1 (SEQ ID NO:1), is meant the mature form(s) of the canine factor VIII protein produced by expression in a mammalian cell (e.g., COS cells, as described below) of the complete open reading frame encoded by the canine DNA sequence of the clone contained in the vector in the deposited host or of a polynucleotide having a nucleic acid sequence as set forth in FIG. 1 (SEQ ID NO:1). As indicated below, the mature canine factor VIII may or may not differ from the predicted "mature" canine factor VIII protein shown in FIG. 1 (SEQ ID NO:2; amino acids from about 20 to about 2343) depending on the accuracy of the predicted cleavage site based on computer analysis.

As one of ordinary skill will appreciate, due to the possibilities of sequencing errors, as well as the variability of cleavage sites for signal sequences in different known proteins, the actual canine factor VIII polypeptide encoded by the deposited cDNA or the polynucleotide depicted in FIG. 1 (SEQ ID NO:1) comprises about 2343 amino acids, but may be anywhere in the range of about 2340 to 2350 amino acids; and the actual N-terminal hydrophobic signal sequence of this protein is about 19 amino acids, but may be anywhere in the range of about 15 to about 25 amino acids.

Nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended anucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells, and those DNA molecules purified (partially or substantially) from a solution whether produced by recombinant DNA or synthetic chemistry techniques. Isolated RNA molecules include in vivo or in vitro RNA transcripts of the DNA molecules of the present invention.

The nucleic acid molecules of the present invention further include genetic constructs comprising canine factor VIII DNA sequences operably linked to regulatory DNA sequences (which may be heterologous regulatory sequences), such as promoters or enhancers as described below, wherein upon expression of these DNA sequences in canine cells, preferably in canine cells in which the DNA sequences are normally repressed or functionally inactive, active canine factor VIII DNA protein is produced. In such constructs, the regulatory sequences may be operably linked to a canine factor VIII polynucleotide encoding mature canine factor VIII protein or any of its variants, precursors, fragments or derivatives described herein. In alternative constructs, the regulatory sequences may be operably linked to a canine factor VIII polynucleotide fragment which does not encode canine factor VIII protein, but which contains a sufficient portion of the canine factor VIII nucleotide sequence to target the genetic construct to the native canine factor VIII locus in a host cell wherein the canine factor VIII gene may be inactive due to repression or mutation. Upon introduction of such constructs into the host cell, the regulatory sequence is integrated into the host cell genome proximal to the canine factor VIII gene via homologous recombination ("gene targeting"), thereby activating or de-repressing canine factor VIII gene expression, as detailed below.

Isolated nucleic acid molecules of the present invention include (a) DNA molecules comprising an open reading frame (ORF) with an initiation codon at positions 1–3 of the nucleotide sequence shown in FIG. 1 (SEQ ID NO:1); (b) DNA molecules comprising the coding sequence for the mature canine factor VIII protein shown in FIG. 1 (SEQ ID NO:2; amino acids 20–2343); and (c) DNA molecules which comprise a sequence substantially different from those described above but which, due to the degeneracy of the genetic code, still encode the canine factor VIII protein. Since the genetic code is well known in the art, it is routine for one of ordinary skill in the art to produce the degenerate variants described above without undue experimentation.

In another aspect, the invention provides isolated nucleic acid molecules encoding the canine factor VIII polypeptide having an amino acid sequence encoded by the above-described deposited cDNA clone designated pBK-cmV (1-6#23) canine FVIII (ATCC Accession No. 209475). Preferably, this nucleic acid molecule will encode the mature polypeptide encoded by the above-described deposited cDNA clone. The invention also provides an isolated nucleic acid molecule having the nucleotide sequence as set forth in FIG. 1 (SEQ ID NO:1) or the nucleotide sequence of the canine factor VIII cDNA contained in the above-described deposited clone, or a nucleic acid molecule having a sequence complementary to any of the above sequences. Such isolated molecules, particularly DNA molecules, are useful as probes for gene mapping, by in situ hybridization with chromosomes, and for detecting expression of the factor VIII gene in canine tissue, for instance, by northern blot analysis.

Nucleic acid molecules of the present invention which encode a canine factor VIII polypeptide may include, but are not limited to, those encoding the amino acid sequence of the mature polypeptide by itself; the coding sequence for the mature polypeptide and additional coding sequences, such as those encoding the about 19-amino acid leader or secretory sequence, such as a pre-, or pro- or prepro- protein sequence; the coding sequence of the mature polypeptide, with or without the aforementioned additional coding sequences, together with additional, non-coding sequences, including for example introns and non-coding 5' and 3' sequences, such as the transcribed, untranslated regions (UTRs) or other 5' flanking sequences that may play a role in transcription (e.g., via providing ribosome- or transcription factor-binding sites), mRNA processing (e.g. splicing and polyadenylation signals) and stability of mRNA; the coding sequence for the mature canine factor VIII polypeptide operably linked to a regulatory DNA sequence, particularly a heterologous regulatory DNA sequence such as a promoter or enhancer; and the coding sequence for the mature canine factor VIII polypeptide linked to one or more coding sequences which code for amino acids that provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described for instance in Gentz et al., *Proc. Natl. Acad. Sci. USA* 86:821–824 (1989), hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). Yet another useful marker peptide for facilitation of purification of canine factor VIII is glutathione S-transferase (GST) encoded by the pGEX fusion vector (see, e.g., Winnacker, *From Genes to Clones*, New York: VCH Publishers, pp. 451–481 (1987)). As discussed below, other such fusion proteins include the canine factor VIII fused to immunoglobulin Fc at the N- or C-terminus.

The present invention further relates to variants of the nucleic acid molecules of the present invention, which encode portions, analogs or derivatives of the canine factor VIII protein. Variants may occur naturally, such as a natural allelic variant. By an "allelic variant" is intended one of several alternate forms of a gene occupying a given locus on a chromosome of an organism (see Lewin, B., ed., *Genes II*, John Wiley & Sons, New York (1985)). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the canine factor VIII protein or portions thereof. Also especially preferred in this regard are conservative substitutions.

Further embodiments of the invention include isolated nucleic acid molecules comprising apolynucleotide having anucleotide sequence at least 90% identical, and more preferably at least 95%, 96%, 97%, 98% or 99% identical to (a) the nucleotide sequence as set forth in FIG. 1 (SEQ ID NO:1); (b) a nucleotide sequence encoding the full-length canine factor VIII polypeptide having the complete amino acid sequence in FIG. 1 (SEQ ID NO:2), including the predicted N-terminal signal sequence; (c) a nucleotide sequence encoding the mature canine factor VIII polypeptide (full-length polypeptide with the signal sequence removed) having the amino acid sequence at positions 20–2343 in FIG. 2 (SEQ ID NO:2); (d) a nucleotide sequence encoding the full-length canine factor VIII polypeptide having the complete amino acid sequence including the N-terminal signal sequence encoded by the deposited cDNA clone designated pBK-cmV (1-6#23) canine FVIII (ATCC Accession No.209475); (e) a nucleotide sequence encoding the mature canine factor VIII polypeptide having the amino acid sequence encoded by the deposited cDNA clone designated pBK-cmV (1-6#23) canine FVIII (ATCC Accession No.209475); or (f) anucleotide sequence complementary to any of the nucleotide sequences in (a), (b), (c), (d) or (e) above.

By a polynucleotide having a nucleotide sequence at least, for example, 95% "identical" to a reference nucleotide sequence encoding a canine factor VIII polypeptide, it is intended that the nucleotide sequence of the polynucleotide is identical to the reference sequence except that the polynucleotide sequence may include up to five point mutations per each 100 nucleotides of the reference nucleotide sequence encoding the canine factor VIII polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIG. 1 (SEQ ID NO:1) can be determined conventionally using known computer programs such as DNAsis software (Hitachi Software, San Bruno, Calif.) for initial sequence alignment followed by ESEE version 3.0 DNA/protein sequence software (cabot@trog.mbb.sfu.ca) for multiple sequence alignments. Alternatively, such determinations may be accomplished using the BESTFIT program (Wisconsin Sequence Analysis Package, Version 8 for Unix, Genetics Computer Group, University Research Park, 575 Science Drive, Madison, Wis. 53711), which employs a local homology algorithm (Smith and Waterman, *Advances in Applied Mathematics* 2: 482–489 (1981)) to find the best segment of homology between two sequences. When using DNAsis, ESEE, BESTFIT or any other sequence alignment program to determine whether a particular sequence is, for instance, 95% identical to a reference sequence according to the present invention, the parameters are set such that the percentage of identity is calculated over the full length of the reference nucleotide sequence and that gaps in homology of up to 5% of the total number of nucleotides in the reference sequence are allowed.

The present invention is directed to nucleic acid molecules at least 90%, 95%, 96%, 97%, 98% or 99% identical to the nucleic acid sequence shown in FIG. 1 (SEQ ID NO:1) or to the nucleotide sequence of the deposited cDNA clone, irrespective of whether they encode a polypeptide having canine factor VIII activity. This is because even where a particular nucleic acid molecule does not encode a polypeptide having canine factor VIII activity, one of skill in the art would still know how to use the nucleic acid molecule, for instance, as a hybridization probe or a polymerase chain reaction (PCR) primer. Uses of the nucleic acid molecules of the present invention that do not encode a polypeptide having canine factor VIII activity include, inter alia, (1) isolating the canine factor VIII gene or allelic variants thereof in a cDNA library; (2) in situ hybridization (e.g., "FISH") to metaphase chromosomal spreads to provide precise chromosomal location of the canine factor VIII gene, as described for human gene localization in Verma et al., *Human Chromosomes: A Manual of Basic Techniques*, Pergamon Press, New York (1988); and (3) northern blot analysis for detecting canine factor VIII mRNA expression in specific tissues.

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence shown in FIG. 1 (SEQ ID NO:1) or to the nucleotide sequence of the deposited cDNA clone will encode a polypeptide having canine factor VIII protein activity. In fact, since degenerate variants of these nucleotide sequences all encode the same polypeptide, this will be clear to the skilled artisan even without performing the above described comparison assay. It will be further recognized by one of ordinary skill in the art that, for such nucleic acid molecules that are not degenerate variants, a reasonable number will also encode a polypeptide having canine factor VIII protein activity. This is because the skilled artisan is fully aware of amino acid substitutions that are either less likely or unlikely to significantly affect protein function (e.g., replacing one aliphatic amino acid with a second aliphatic amino acid). For example, guidance concerning how to make phenotypically silent amino acid substitutions is provided in Bowie, J. U., et al., *Science* 247:1306–1310 (1990), and the references cited therein.

Vectors and Host Cells

The present invention also relates to genetic constructs comprising the isolated nucleic acid molecules of the invention operably linked to regulatory DNA sequences as described in detail below, vectors which comprise these genetic constructs or the isolated DNA molecules of the present invention, and host cells which comprise these vectors. In addition, the invention relates to the production of canine factor VIII polypeptides or fragments thereof by recombinant techniques using these vectors and host cells.

Vectors comprising the genetic constructs or the isolated DNA molecules of the present invention may be introduced into host cells using well-known techniques such as infection, transduction, transfection, electroporation and transformation. The vector may be, for example, a phage, plasmid, viral or retroviral vector, and is preferably an expression vector as described below. Retroviral vectors may be replication-competent or -defective. In the latter case, viral propagation generally will occur only in complementing host cells.

The polynucleotides may be joined to a vector containing a selectable marker for propagation in a host. Generally, a plasmid vector is introduced into mammalian or avian cells in a precipitate, such as a calcium phosphate precipitate, or in a complex with a charged lipid (e.g., LIPO-FECTAMINE™; Life Technologies, Inc.; Rockville, Md.) or in a complex with a virus (such as an adenovirus) or components of a virus (such as viral capside peptides). If the vector is a virus, it may be packaged in vitro using an appropriate packaging cell line and then transduced into host cells.

Preferred are vectors comprising cis-acting control regions to the polynucleotide of interest. Appropriate trans-acting factors may be supplied by the host, by a complementing vector or by the vector itself upon introduction into the host.

In certain preferred embodiments in this regard, the vectors provide for specific expression, which may be inducible and/or cell type-specific. Particularly preferred among such expression vectors are those inducible by environmental factors that are easy to manipulate, such as temperature and nutrient additives.

Expression vectors useful in the present invention include chromosomal-, episomal- and virus-derived vectors, e.g., vectors derived from bacterial plasmids, bacteriophages, yeast episomes, yeast chromosomal elements, viruses such as baculoviruses, papova viruses, vaccinia viruses, adenoviruses, fowl pox viruses, pseudorabies viruses and retroviruses, and vectors derived from combinations thereof, such as cosmids and phagemids.

In a preferred embodiment, an isolated nucleic acid molecule of the invention is operably linked to an appropriate regulatory sequence, preferably a promoter such as the phage lambda PL promoter, promoters from T3, T7 and SP6 phages, the *E. coli* lac, trp and tac promoters, the SV40 early and late promoters, promoters of retroviral LTRs and native human factor VIII promoters and derivatives thereof, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiation codon (AUG) at the beginning and a termination codon (UAA, UGA or UAG) appropriately positioned at the end of the polypeptide to be translated.

As indicated above, the expression vectors will preferably include at least one selectable marker. Such markers include dihydrofolate reductase (dhfr) or neomycin (neo) resistance for eukaryotic cell culture and tetracycline (tet) or ampicillin (amp) resistance genes for culturing in *E. coli* and other bacteria. Representative examples of appropriate hosts include, but are not limited to, bacterial cells, such as *E. coli*, *Streptomyces* and *Salmonella typhimurium* cells; fungal cells, such as yeast cells; insect cells such as Drosophila S2, Spodoptera Sf9 or Sf21 cells and Trichoplusa High-Five cells; other animal cells (particularly mammalian cells and most particularly human cells) such as CHO, COS, Bowes melanoma cells and HepG2 and other liver cell lines; and higher plant cells. Appropriate culture media and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A and pNH46A, available from Stratagene; pcDNA3 available from Invitrogen; and pGEX, ptrxfus, ptrc99a, pET-5, pET-9, pKK223-3, pKK233-3, pDR540 and pRIT5 available from Pharmacia. Among preferred eukaryotic vectors are pWLNEO, pSV2CAT, pOG44, pXT1, pBK and pSG available from Stratagene; and pSVK3, pBPV, pMSG and pSVL available from Pharmacia. Other suitable vectors will be readily apparent to the skilled artisan.

Among known bacterial promoters suitable for use in the present invention include the *E. coli* lacI and lacZ promoters, the T3, T7 and SP6 phage promoters, the gpt promoter, the lambda PR and PL promoters and the trp promoter. Suitable eukaryotic promoters include the CMV immediate early promoter, the HSV thymidine kinase promoter, the early and late SV40 promoters, the promoters of retroviral LTRs, such as those of the Rous sarcoma virus (RSV), and metallothionein promoters, such as the mouse metallothionein-I promoter.

Introduction of the construct into the host cell can be effected by calcium phosphate transfection, DEAE-dextran mediated transfection, cationic lipid-mediated transfection, electroporation, transduction, infection, nucleic acid-coated microprojectile bombardment or other methods. Such methods are described in many standard laboratory manuals, such as Davis et al., *Basic Methods In Molecular Biology* (1986).

In some embodiments, the isolated polynucleotides of the present invention may be operably linked to a regulatory genetic sequence, which may be a homologous or a heterologous regulatory genetic sequence, to form a genetic construct. Genetic constructs according to this aspect of the invention are intended to encompass not only those comprising a polynucleotide encoding mature canine factor VIII protein operably linked to a regulatory DNA sequence, but also those constructs comprising one or more regulatory sequences operably linked to a canine factor VIII polynucleotide fragment which does not encode canine factor VIII protein, but which contains a sufficient portion of the canine factor VIII nucleotide sequence (a "targeting fragment") to target the genetic construct to the native canine factor VIII locus upon introduction into a host cell wherein the canine factor VIII gene may be inactive due to repression or mutation. These constructs may be inserted into a vector as above, and the vectors introduced into a host cell, the genome of which comprises the target gene, by any of the methods described above. The canine factor VIII polynucleotide will then integrate into the host cell genome by homologous recombination. In the case of a construct comprising a homologous or heterologous regulatory sequence linked to a targeting canine factor VIII polynucleotide fragment, the regulatory sequence will be targeted to the native canine factor VIII locus in the host cell, and will amplify or de-repress the expression of the native canine factor VIII gene in the host cell, thereby increasing the level of production of canine factor VIII protein. Alternatively, such gene targeting may be carried out using genetic constructs comprising the above-described canine factor VIII targeting fragment in the absence of a regulatory sequence; such an approach may be used, for example, to correct point mutations in the canine factor VIII gene (see Steeg, C. M., et al., *Proc. Natl. Acad. Sci. USA* 87(12):4680–4684 (1990) for a description of such approaches to correcting point mutations in other mammalian genes). Such methods of producing genetic constructs, introducing genes of interest into a host cell via homologous recombination and producing the encoded polypeptides are generally described in U.S. Pat. No. 5,578,461; WO 94/12650; WO 93/09222; and WO 90/14092, the disclosures of which are expressly incorporated herein by reference in their entireties.

Transcription of the DNA encoding the polypeptides of the present invention by higher eukaryotes may be increased by inserting an enhancer sequence into the vector. Enhancers are cis-acting elements of DNA, usually from about 10 to 300 bp, that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers. In an alternative embodiment of the invention, transcriptional activation of the canine factor VIII gene may be enhanced by inserting one or more concatamerized elements from the native human or canine factor VIII promoter into the vector.

For secretion of the translated protein into the lumen of the endoplasmic reticulum, into the periplasmic space or into the extracellular environment, appropriate secretion signals may be incorporated into the expressed polypeptide. The signals may be endogenous to the polypeptide or they may be heterologous signals.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among other purposes, is a familiar and routine technique in the art. A preferred fusion protein comprises a heterologous region from an immunoglobulin that is useful to solubilize proteins. For example, EP 0 464 533 discloses fusion proteins comprising various portions of constant (Fc) region of immunoglobulin molecules together with another human protein or part thereof. In many cases, the Fc portion of a fusion protein is thoroughly advantageous for use in therapy and diagnosis and thus results, for example, in improved pharmacokinetic properties (EP 0 232 262). On the other hand, for some uses it would be desirable to be able to delete the Fc part after the fusion protein has been expressed, detected and purified in the advantageous manner described. This is the case when the Fc portion proves to be a hindrance to use in therapy, diagnosis or further manufacturing, for example when the fusion protein is to be used as an antigen for immunizations for the preparation of antibodies.

The canine factor VIII protein can be recovered and purified from recombinant cell cultures by well-known methods including ammonium sulfate or ethanol precipitation, acid extraction, anion or cation exchange chromatography, lectin chromatography, gel filtration, hydrophobic interaction chromatography, affinity chromatography and hydroxylapatite chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, insect, mammalian, avian and higher plant cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

Canine Factor VIII Polypeptides and Fragments

The invention further provides an isolated canine factor VIII polypeptide having the amino acid sequence encoded by a polynucleotide having the nucleotide sequence set forth in FIG. 1 (SEQ ID NO:1) or by the deposited cDNA clone, or the amino acid sequence in FIG. 1 (SEQ ID NO:2), or a peptide or polypeptide comprising a portion of the above polypeptides. The terms "peptide" and "oligopeptide" are considered synonymous (as is commonly recognized) and each term can be used interchangeably as the context requires to indicate a chain of at least two amino acids coupled by (a) peptidyl linkage(s). The word "polypeptide" is used herein for chains containing more than ten amino acid residues. All oligopeptide and polypeptide formulas or sequences herein are written from left to right and in the direction from amino terminus to carboxy terminus.

It will be recognized in the art that some amino acid sequences of the canine factor VIII polypeptide can be varied without significant effect on the structure or function of the protein. If such differences in sequence are contemplated, it should be remembered that there will be critical areas on the protein which determine activity. In general, it is possible to replace residues which form the tertiary structure, provided that residues performing a similar function are used. In other instances, the type of residue may be completely unimportant if the alteration occurs at a non-critical region of the protein.

Thus, the invention further includes variations of the canine factor VIII polypeptide, including allelic variants, which show substantial canine factor VIII polypeptide activity or which include regions of the canine factor VIII protein such as the protein portions discussed below. Such mutants include deletions, insertions, inversions, repeats, and type substitutions (for example, substituting one hydrophilic residue for another, but not strongly hydrophilic for strongly hydrophobic as a rule). Small changes or such "neutral" amino acid substitutions will generally have little effect on activity.

Typical conservative substitutions are the replacements, one for another, among the aliphatic amino acids Ala, Val, Leu and Ile; interchange of the hydroxylated residues Ser and Thr; exchange of the acidic residues Asp and Glu; substitution between the amidated residues Asn and Gln; exchange of the basic residues Lys and Arg; and replacements among the aromatic residues Phe and Tyr.

Thus, the fragment, derivative or analog of the polypeptide of FIG. 1 (SEQ ID NO:2), or that encoded by a polynucleotide having a nucleic acid sequence as set forth in FIG. 1 (SEQ ID NO:1) or the nucleotide sequence of the deposited cDNA clone, may be (i) one in which one or more of the amino acid residues are substituted with a conserved or non-conserved amino acid residue (preferably a conserved amino acid residue), and such substituted amino acid residue may be encoded by the genetic code or may be an amino acid (e.g., desmosine, citrulline, ornithine, etc.) that is not encoded by the genetic code; (ii) one in which one or more of the amino acid residues includes a substituent group (e.g., a phosphate, hydroxyl, sulfate or other group) in addition to the normal "R" group of the amino acid; (iii) one in which the mature polypeptide is fused with another compound, such as a compound to increase the half-life of the polypeptide (for example, polyethylene glycol), or (iv) one in which additional amino acids are fused to the mature polypeptide, such as an immunoglobulin Fc region peptide, a leader or secretory sequence, a sequence which is employed for purification of the mature polypeptide (such as GST) or a proprotein sequence. Such fragments, derivatives and analogs are intended to be encompassed by the present invention, and are within the scope of those skilled in the art from the teachings herein and the state of the art at the time of invention.

Of particular interest are substitutions of a positively charged amino acid with another positively charged amino acid or with neutral or negatively charged amino acids. The latter results in proteins with reduced positive charge to improve the physical characteristics of the canine factor VIII protein. The prevention of aggregation is highly desirable. Aggregation of proteins not only results in a loss of activity but can also be problematic when preparing pharmaceutical formulations, because they can be immunogenic (Pinckard et al., *Clin. Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)). Such amino acid changes are preferably of a minor nature, such as conservative amino acid substitutions that do not significantly affect the folding or activity of the protein, examples of which are described above. Amino acids in the canine factor VIII protein of the present invention that are essential for function can be identified by known methods in the art, such as site-directed mutagenesis.

The polypeptides of the present invention are preferably provided in an isolated form, and preferably are substantially purified. A recombinantly produced version of the canine factor VIII polypeptide can be substantially purified by the one-step method described in Smith and Johnson, *Gene* 67:31–40 (1988). As used herein, the term "substantially purified" means a preparation of canine factor VIII polypeptide wherein at least 50%, preferably at least 70%, and more preferably at least 80%, 85%, 90%, 91%, 92%, 93%, 94%, 95%, 96%, 97%, 98% or 99% of contaminating proteins (i.e., those that are not canine factor VIII proteins) have been removed from the preparation.

The polypeptides of the present invention include those which are at least 90% identical, more preferably at least 95% identical, and most preferably at least 96%, 97%, 98% or 99% identical to the polypeptide encoded by a polynucleotide having a nucleic acid sequence as set forth in FIG. 1 (SEQ ID NO:1) or as contained in the deposited cDNA clone, or to the polypeptide of FIG. 1 (SEQ ID NO:2), and also include portions of such polypeptides with at least 30 amino acids and more preferably at least 50 amino acids.

By a polypeptide having an amino acid sequence at least, for example, 95% "identical" to a reference amino acid sequence of a canine factor VIII polypeptide is intended that the amino acid sequence of the polypeptide is identical to the reference sequence except that the polypeptide sequence may include up to five amino acid alterations per each 100 amino acids of the reference amino acid of the canine factor VIII polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino (N–) or carboxy (C–) terminal positions of the reference amino acid sequence or anywhere between those terminal positions, interspersed either individually among residues in the reference sequence or in one or more contiguous groups within the reference sequence.

The polypeptides of the present invention can be used as molecular weight markers on SDS-PAGE gels or on molecular sieve gel filtration columns using methods well known to those of skill in the art. In addition, as described in detail below, the polypeptides of the present invention can be used to raise polyclonal and monoclonal antibodies which are useful in assays for detecting canine factor VIII protein expression or as antagonists capable of inhibiting canine factor VIII protein function or for the isolation of canine factor VIII protein.

In another aspect, the present invention provides a peptide or polypeptide comprising an epitope-bearing portion of a polypeptide of the invention, which may be used to raise antibodies, particularly monoclonal antibodies, that bind specifically to a canine factor VIII polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. These immunogenic epitopes are believed to be confined to a few loci on the molecule. On the other hand, a region of a protein molecule to which an antibody can bind is defined as an "antigenic epitope." The number of immunogenic epitopes of a protein generally is less than the number of antigenic epitopes. See, for instance, Geysen et al., *Proc Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein (see, e.g., Sutcliffe, J. G., et al., *Science* 219:660–666 (1983)). Peptides capable of eliciting protein-reactive sera are frequently represented in the primary sequence of a protein, can be characterized by a set of simple chemical rules, and are not confined to the immunodominant regions of intact proteins (i.e., immunogenic epitopes) or to the amino or carboxy termini. Peptides that are extremely hydrophobic and those of six or fewer residues generally are ineffective at inducing antibodies that bind to the mimicked protein; longer peptides, especially those containing proline residues, usually are effective (Sutcliffe, J. G., et al., *Science* 219:660–666 (1983)).

Epitope-bearing peptides and polypeptides of the invention designed according to the above guidelines preferably contain a sequence of at least seven, more preferably at least nine and most preferably between about 15 to about 30 amino acids contained within the amino acid sequence of a polypeptide of the invention. However, peptides or polypeptides comprising a larger portion of an amino acid sequence of a polypeptide of the invention, containing about 30 to about 50 amino acids, or any length up to and including the entire amino acid sequence of a polypeptide of the invention, also are considered epitope-bearing peptides or polypeptides of the invention and also are useful for inducing antibodies that react with the mimicked protein. Preferably, the amino acid sequence of the epitope-bearing peptide is selected to provide substantial solubility in aqueous solvents (i.e., the sequence includes relatively hydrophilic residues and highly hydrophobic sequences are preferably avoided); sequences containing proline residues are particularly preferred.

Non-limiting examples of epitope-bearing polypeptides or peptides that can be used to generate canine factor VIII-specific antibodies include a polypeptide consisting essentially of amino acid residues from about 1645 to about 1758 in FIG. 2 (SEQ ID NO:2) and a polypeptide consisting essentially of amino acid residues from about 2259 to about 2332 in FIG. 1 (SEQ ID NO:2).

The epitope-bearing peptides and polypeptides of the invention may be produced by any conventional means for making peptides or polypeptides including recombinant means using nucleic acid molecules of the invention. For instance, a short epitope-bearing amino acid sequence may be fused to a larger polypeptide which acts as a carrier during recombinant production and purification, as well as during immunization to produce anti-peptide antibodies. Epitope-bearing peptides also may be synthesized using known methods of chemical synthesis (see, e.g., U.S. Pat. No. 4,631,211; Houghten, R. A., *Proc. Natl. Acad. Sci. USA* 82:5131–5135 (1985)).

As one of skill in the art will appreciate, canine factor VIII polypeptides of the present invention and epitope-bearing fragments thereof may be immobilized onto a solid support, by techniques that are well-known and routine in the art. By "solid support" is intended any solid support to which a peptide can be immobilized. Such solid supports include, but are not limited to nitrocellulose, diazocellulose, glass, polystyrene, polyvinylchloride, polypropylene, polyethylene, dextran, Sepharose, agar, starch, nylon, beads and microtitre plates. Linkage of the peptide of the invention to a solid support can be accomplished by attaching one or both ends of the peptide to the support. Attachment may also be made at one or more internal sites in the peptide. Multiple attachments (both internal and at the ends of the peptide) may also be used according to the invention. Attachment can be via an amino acid linkage group such as a primary amino group, a carboxyl group, or a sulfhydryl (SH) group or by chemical linkage groups such as with cyanogen bromide (CNBr) linkage through a spacer. For non-covalent attachments, addition of an affinity tag sequence to the peptide can be used such as GST (Smith, D. B., and Johnson, K. S., *Gene* 67:31 (1988)), polyhistidines (Hochuli, E., etal., *J. Chromatog.* 411:77 (1987)), or biotin. Such affinity tags may be used for the reversible attachment of the peptide to the support. Such immobilized polypeptides or fragments will be useful, for example, in isolating antibodies directed against canine factor VIII, as described below.

As one of skill in the art will also appreciate, canine factor VIII polypeptides of the present invention and the epitope-bearing fragments thereof described above can be combined with parts of the constant domain of immunoglobulins (Ig), resulting in chimeric polypeptides. These fusion proteins facilitate purification and show an increased half-life in vivo (EP 0 394,827; Traunecker et al., *Nature* 331:84–86 (1988)).

Canine Factor VIII Antibodies

Epitope-bearing peptides and canine factor VIII polypeptides of the invention are used to induce antibodies directed against canine factor VIII according to methods well known in the art. See, for instance, Sutcliffe et al., supra; Wilson et al., supra; and Bittle, F. J., et al., *J. Gen. Virol.* 66:2347–2354 (1985). Canine factor VIII-protein specific antibodies can be raised against the intact canine factor VIII protein or an antigenic polypeptide fragment thereof, which may be presented together with a carrier protein, such as an albumin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')$_2$ fragments) which are capable of specifically binding to canine factor VIII protein. Fab and F(ab')$_2$ fragments lack the Fc fragment of intact antibody, clear more rapidly from the circulation, and may have less non-specific tissue binding than an intact antibody (Wahl et al., *J. Nucl. Med.* 24:316–325 (1983)). Thus, these fragments are preferred.

The antibodies of the present invention may be polyclonal or monoclonal, and may be prepared by any of a variety of methods. For example, polyclonal antibodies may be made by immunizing an animal with the canine factor VIII polypeptides of the invention according to standard techniques (see, e.g., Harlow, E., and Lane, D., *Antibodies: A Laboratory Manual*, Cold Spring Harbor, N.Y.: Cold Spring Harbor Laboratory Press (1988); Kaufman, P. B., et al., In: *Handbook of Molecular and Cellular Methods in Biology and Medicine*, Boca Raton, Fla.: CRC Press, pp. 468–469 (1995)). In the most preferred method, the antibodies of the present invention are monoclonal antibodies (or canine factor VIII protein-binding fragments thereof). Such monoclonal antibodies can be prepared using hybridoma technology that is well-known in the art (Köhler et al., *Nature* 256:495 (1975); Köhler et al., *Eur. J. Immunol.* 6:511 (1976); Köhler et al., *Eur. J. Immunol.* 6:292 (1976); Hammerling etal., In: *Monoclonal Antibodies and T-Cell Hybridomas*, New York: Elsevier, pp. 563–681 (1981); Kaufman, P. B., et al., In: *Handbook of Molecular and Cellular Methods in Biology and Medicine*, Boca Raton, Fla.: CRC Press, pp. 444–467 (1995)).

Alternatively, antibodies capable of binding to canine factor VIII protein may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, canine factor VIII protein-specific antibodies are used to immunize an animal, preferably a mouse. The splenocytes of such an animal are then used to produce hybridoma cells, and the hybridoma cells are screened to identify clones which produce an antibody whose ability to bind to the canine factor VIII protein-specific antibody can be blocked by the canine factor VIII protein antigen. Such antibodies comprise anti-idiotypic antibodies to the canine factor VIII protein-specific antibody and can be used to immunize an animal to induce formation of further canine factor VIII protein-specific antibodies.

In another preferred embodiment of the invention, the present antibodies may be prepared as chimeric antibodies. According to the invention, such chimeric antiboides may comprise an antigen-binding domain (i.e., the region of the antibody binding to canine factor VIII) from a first species and one or more constant regions from a second species. See U.S. Pat. No. 4,816,567, which is directed to methods for the preparation of chimeric antibodies, the disclosure of which is incorporated herein by reference in its entirety.

It will be appreciated that Fab, F(ab')$_2$ and other fragments of the antibodies of the present invention may be used according to the methods disclosed herein. Such fragments are typically produced by proteolytic cleavage, using enzymes such as papain (to produce Fab fragments) or pepsin (to produce F(ab')$_2$ fragments). Alternatively, canine factor VIII protein-binding fragments can be produced through the application of recombinant DNA technology or through synthetic chemistry.

The canine factor VIII protein-specific antibodies of the present invention are preferably detectably labeled, most preferably with an enzyme, radioisotopic, non-radioactive isotopic, fluorescent, toxin, chemiluminescent or nuclear magnetic resonance (NMR) contrast agent label. Suitable examples of each of these types of labels are well-known to one of ordinary skill in the art. Typical techniques for binding a label to an antibody are provided by Kennedy et al., *Clin. Chim. Acta* 70:1–31 (1976), and Schurs et al., *Clin. Chim. Acta* 81:1–40 (1977), all of which methods are incorporated by reference herein.

In an additional preferred embodiment of the invention, the antibodies produced as described above may be covalently or non-covalently immobilized on a solid phase support. By "solid phase support" is intended any solid support to which an antibody can be immobilized. Such solid phase supports include, but are not limited to nitrocellulose, diazocellulose, glass, polystyrene, polyvinylchloride, polypropylene, polyethylene, dextran, Sepharose, agar, starch, nylon, beads and microtitre plates. Preferred are beads made of glass, latex or amagnetic material. Linkage of the antibodies of the invention to a solid support can be accomplished by attaching one or more ends of the antibody to the support. Attachment may also be made at one or more internal sites in the antibody. Multiple attachments (both internal and at the ends of the antibody) may also be used according to the invention. Attachment can be via an amino acid linkage group such as a primary amino group, a carboxyl group, or a sulfhydryl (SH) group or by chemical linkage groups such as with cyanogen bromide (CNBr) linkage through a spacer. For non-covalent attachments, addition of an affinity tag sequence to the antibody can be used such as GST (Smith, D. B., and Johnson, K. S. *Gene* 67:31 (1988)); polyhistidines (Hochuli, E. et al., *J. Chromatog.* 411:77 (1987)); or biotin. Alternatively, an indirect coupling agent such as Protein A or Protein G (available commercially, e.g., from Sigma Chemical Co., St. Louis, Mo.) which binds to the Fc region of antibodies may be attached to the solid support and the antibodies of the invention attached thereto by simply incubating the antibodies with the solid support containing the immobilized Protein A or Protein G. Such affinity tags may be also used for the reversible attachment of the antibodies of the present invention to the support.

Factor VIII Deficiency Diagnosis

For a number of bleeding disorders, it is believed that significantly lower levels of factor VIII gene expression can be detected in certain tissues (e.g., liver, spleen, kidney or lymphoid tissue) or bodily fluids (e.g., blood, serum or plasma) taken from an individual having such a disorder, relative to a "standard" factor VIII gene expression level, i.e., the factor VIII expression level in tissue or bodily fluids obtained from an individual not afflicted with the bleeding disorder. Thus, the invention also provides methods useful during diagnosis of a canine factor VIII-dependent bleeding disorder, which involve (a) obtaining a sample oftissue, cells, body fluid or extracts thereof from a first canine; (b) assaying canine factor VIII gene expression in the sample; and (c) comparing the canine factor VIII gene expression level in the sample to that of a standard sample obtained from a second canine not afflicted with the disorder, wherein a decrease in canine factor VIII gene expression level in the assayed sample obtained from the first canine relative to that of the standard sample obtained from the second canine is indicative of a canine factor VIII-dependent bleeding disorder in the first canine.

By "assaying the expression level of the gene encoding the canine factor VIII protein" is intended qualitatively estimating or quantitatively measuring the level of the canine factor VIII protein or the level of the mRNA encoding the canine factor VIII protein in a first biological sample either directly (e.g., by determining or estimating absolute protein level or mRNA level) or relatively (e.g., by comparing to the canine factor VIII protein level or mRNA level in a second biological sample).

Preferably, the canine factor VIII protein level or mRNA level in the first biological sample is measured or estimated and compared to a standard canine factor VIII protein level or mRNA level, the standard being taken from a second biological sample obtained from an individual not having a disorder characterized by a canine factor VIII deficiency. As will be appreciated in the art, once a standard canine factor VIII protein level or mRNA level is known, it can be used repeatedly as a standard for comparison.

By "biological sample" is intended any biological sample obtained from an individual, cell line, tissue culture, or other source which contains canine factor VIII protein or mRNA. Biological samples include mammalian, particularly canine, body fluids (such as blood, sera, plasma, urine, synovial fluid and spinal fluid) which contain secreted mature canine factor VIII protein, and cells and tissue containing canine factor VIII protein and/or mRNA derived from liver, spleen, kidney or lymphoid organs or tissues. Methods for obtaining tissue biopsies and body fluids from mammals are well known in the art. Where the biological sample is to include mRNA, a tissue biopsy is the preferred source.

The present invention is useful for detecting disorders characterized by factor VIII deficiencies in mammals, particularly canines. In particular the invention is useful during diagnosis of hemophilia A and other associated bleeding disorders in canines characterized by a deficiency in factor VIII.

Total cellular RNA can be isolated from a biological sample using any suitable technique such as the single-step guanidinium-thiocyanate-phenol-chloroform method described in Chomczynski and Sacchi, *Anal. Biochem.* 162:156–159 (1987). Levels of mRNA encoding the canine factor VIII protein are then assayed using any appropriate method, including northern blot analysis, S1 nuclease mapping, the polymerase chain reaction (PCR), reverse transcription in combination with the polymerase chain reaction (RT-PCR), reverse transcription in combination with the ligase chain reaction (RT-LCR) and PCR or LCR in combination with hybridization. Northern blot analysis can be performed as described in Harada et al., *Cell* 63:303–312 (1990), and S1 mapping can be performed as described in Fujita et al., *Cell* 49:357–367 (1987). Preferably, levels of mRNA encoding the canine factor VIII protein are assayed using the RT-PCR method described in Makino et al., *Technique* 2:295–301 (1990), using any set of oligonucleotide primers which will amplify reverse-transcribed target mRNA designed according to art-known methods. Variations on each of these methods are apparent to the skilled artisan.

Canine factor VIII protein levels in a biological sample can be assayed using any art-known method, of which antibody-based techniques are preferred. For example, canine factor VIII protein expression in tissues can be studied with classical immunohistological methods. In one such method, the specific recognition is provided by a primary antibody (polyclonal or monoclonal) and a secondary detection system comprising fluorescent-, enzyme-, or otherwise-labeled conjugated secondary antibodies is used to detect binding of the primary antibody. Alternatively, the primary antibody itself may be detectably labeled. As a result, immunohistological labeling of a tissue section for pathological examination is obtained. Alternatively, tissues, cells and bodily fluids can be extracted, e.g., with urea and a nonionic detergent, for the liberation of canine factor VIII protein, thereby producing extracts of tissues, cells and bodily fluids for western-blot or dot/slot assay of canine factor VIII content according to routine immunoblotting methods (Jalkanen, M., et al., *J. Cell. Biol.* 101:976–985 (1985); Jalkanen, M., et al., *J. Cell Biol.* 105:3087–3096 (1987)).

Other antibody-based methods useful for detecting canine factor VIII protein gene expression include immunoassays, such as the enzyme-linked immunosorbent assay (ELISA) and the radioimmunoassay (RIA). For example, a canine factor VIII protein-specific monoclonal antibody, prepared as described above, can be used both as an immunoadsorbent and as an enzyme-labeled probe to detect and quantify the canine factor VIII protein. The amount of canine factor VIII protein present in a sample can be calculated by reference to the amount present in a standard preparation using a linear regression computer algorithm. Such an ELISA for detecting a tumor antigen is described in Iacobelli et al., *Breast Cancer Research and Treatment* 11:19–30 (1988). In an alternative ELISA assay, two distinct specific monoclonal antibodies can be used to detect canine factor VIII protein in a body fluid. In this assay, one of the antibodies is used as the immunoadsorbent and the other as the enzyme-labeled probe.

Therapeutics

In addition to their use in disease diagnosis, the canine factor VIII protein and fragments thereof may be used in therapeutic regimens for treating mammals afflicted with certain diseases. Particularly amenable to such an approach are those diseases and disorders that are characterized by decreased levels of canine factor VIII protein expression in the tissues of a mammal suffering from the disease, and which are responsive to treatments which increase the expression of canine factor VIII protein intracellularly or intrasystemically. Diseases that are particularly treatable by these methods include canine hemophilia A and other bleeding disorders characterized by factor VIII deficiencies in the afflicted animal.

Gene Therapy

A canine suffering from such a disease is preferably treated by gene therapy. By undertaking this approach, the level of canine factor VIII protein expression is increased in cells, tissues and/or body fluids of the animal being treated, thereby either curing the factor VIII deficiency-dependent bleeding disorder or inducing a remission or an alleviation of the symptoms thereof. Analogous gene therapy approaches have proven effective or to have promise in the treatment of certain forms of human hemophilia (Bontempo, F. A., et al., *Blood* 69:1721–1724 (1987); Palmer, T. D., et al.,*Blood* 73:438–445 (1989); Axelrod, J. H., et al., *Proc. Natl. Acad. Sci. USA* 87:5173–5177 (1990); Armentano, D., et al., *Proc. Natl. Acad. Sci. USA* 87:6141–6145 (1990)), as well as in the treatment of certain other mammalian diseases such as cystic fibrosis (Drumm, M. L., et al., *Cell* 62:1227–1233 (1990); Gregory, R. J., et al., *Nature* 347:358–363 (1990); Rich, D. P., et al., *Nature* 347:358–363 (1990)), Gaucher disease (Sorge, J., et al., *Proc. Natl. Acad. Sci. USA* 84:906–909 (1987); Fink, J. K., et al., *Proc. Natl. Acad. Sci. USA* 87:2334–2338 (1990)), muscular dystrophy (Partridge, T. A., et al., *Nature* 337:176–179 (1989); Law, P. K., et al., *Lancet* 336:114–115 (1990); Morgan, J. E., et al., *J. Cell Biol.* 111:2437–2449 (1990)), and metastatic melanoma (Rosenberg, S. A., et al., *Science* 233:1318–1321 (1986); Rosenberg, S. A., et al., *N. Eng. J. Med.*

319:1676–1680 (1988); Rosenberg, S. A., et al., *N. Eng J. Med.* 323:570–578 (1990)).

In a preferred such approach, a polynucleotide having the nucleotide sequence depicted in FIG. 1 (SEQ ID NO:1) of that of the deposited cDNA clone designated pBK-cmV (1-6#23) canine FVIII (ATCC Accession No. 209475), a nucleic acid molecule encoding a canine factor VIII protein or a fragment thereof depicted in FIG. 1 (SEQ ID NO:2), or a nucleic acid molecule complementary to those described above, may be incorporated into a vector suitable for introducing the nucleic acid molecule into cells of the mammal to be treated, to form a transfection vector. Suitable vectors for this purpose include retroviruses and adenoviruses. Alternatively, the nucleic acid molecules of the invention may be complexed into a molecular conjugate with a virus (e.g., an adenovirus) or with viral components (e.g., viral capsid proteins).

Techniques for the formation of vectors comprising the canine factor VIII-encoding nucleic acid molecule are well-known in the art, and are generally described in "Working Toward Human Gene Therapy," Chapter 28 in *Recombinant DNA*, 2nd Ed., Watson, J. D. et al., eds., New York: Scientific American Books, pp. 567–581 (1992). In addition, general methods for construction of gene therapy vectors and the introduction thereof into affected animals for therapeutic purposes may be obtained in the above-referenced publications, the disclosures of which are specifically incorporated herein by reference in their entirety. In one such general method, vectors comprising the isolated polynucleotides of the present invention are directly introduced into the cells or tissues of the affected canine, preferably by injection, inhalation, ingestion or introduction into a mucous membrane via solution; such an approach is generally referred to as "in vivo" gene therapy. Specific approaches for in vivo gene therapy using canine factor VIII genetic constructs of the present invention are described in detail in Example 5 below.

Alternatively, cells or tissues, e.g., hematopoietic cells from bone marrow, may be removed from the affected animal and placed into culture according to methods that are well-known to one of ordinary skill in the art; the vectors comprising the canine factor VIII polynucleotides may then be introduced into these cells or tissues by any of the methods described generally above for introducing isolated polynucleotides into a cell or tissue, and, after a sufficient amount of time to allow incorporation of the canine factor VIII polynucleotides, the cells or tissues may then be re-inserted into the affected animal or a second animal in need of canine factor VIII therapy. Since the introduction of the canine factor VIII gene is performed outside of the body of the affected animal, this approach is generally referred to as "ex vivo" gene therapy.

For both in vivo and ex vivo gene therapy, the isolated canine factor VIII polynucleotides of the invention may alternatively be operatively linked to a regulatory DNA sequence, which may be a heterologous regulatory DNA sequence, to form a genetic construct as described above. This genetic construct may then be inserted into a vector, which is then directly introduced into the affected animal in an in vivo gene therapy approach, or into the cells or tissues of the affected animal in an ex vivo approach. In another preferred embodiment, the genetic construct of the invention may be introduced into the cells or tissues of the animal, either in vivo or ex vivo, in a molecular conjugate with a virus (e.g., an adenovirus) or viral components (e.g. viral capsid proteins). Alternatively, transfected host cells, which may be homologous or heterologous, may be encapsulated within a semi-permeable barrier device and implanted into the affected animal, allowing passage of canine factor VIII into the tissues and circulation of the animal but preventing contact between the animal's immune system and the transfected cells (see WO 93/09222). These approaches result in increased production of canine factor VIII by the treated animal via (a) homologous recombination between the nucleic acid molecule of the invention encoding the canine factor VIII protein (contained within the genetic construct) and the defective canine factor VIII gene in the cells of the affected animal; (b) random insertion of the canine factor VIII gene into the host cell genome; or (c) incorporation of the canine factor VIII gene into the nucleus of the cells where it may exist as an extrachromosomal genetic element. General descriptions of such methods and approaches to gene therapy may be found, for example, in U.S. Pat. No. 5,578,461; WO 94/12650; and WO 93/09222.

Regardless of the approach used, however, use of the therapeutic methods and compositions of the present invention will result in the increased production of canine factor VIII by the cells and tissues of the treated canine, such that the factor VIII deficiency-dependent bleeding disorder will either be cured, or the symptoms thereof will be alleviated, ameliorated or eliminated.

Protein Therapy

It will also be appreciated that conditions caused by a decrease in the standard or normal level of canine factor VIII activity in an individual, such as canine hemophilia A or other bleeding disorders characterized by a canine factor VIII deficiency, can be treated by administration of canine factor VIII protein to the affected animal. Thus, the invention further provides a method of treating an individual in need of an increased level of canine factor VIII activity comprising administering to such an individual a pharmaceutical composition comprising a therapeutically effective amount of an isolated canine factor VIII polypeptide of the invention, particularly a mature form of the canine factor VIII protein, effective to increase the level of canine factor VIII activity in such an individual.

The canine factor VIII polypeptide composition will be formulated and dosed in a fashion consistent with good medical and veterinary practice, taking into account the clinical condition of the individual patient (especially the side effects of treatment with canine factor VIII polypeptide alone), the site of delivery of the canine factor VIII polypeptide composition, the method of administration, the scheduling of administration, and other factors known to practitioners. The "therapeutically effective amount" of canine factor VIII polypeptide for purposes herein is thus determined by such considerations.

As a general proposition, the total therapeutically effective amount of canine factor VIII polypeptide administered parenterally per dose will be in the range of about 1 $\mu$g/kg/day to 10 $\mu$g/kg/day of patient body weight, although, as noted above, this will be subject to therapeutic discretion. More preferably, this dose is at least 0.01 $\mu$g/kg/day, and most preferably for canines between about 1 and 10 $\mu$g/kg/day for the polypeptide. If given continuously, the canine factor VIII polypeptide is typically administered at a dose rate of about 1 $\mu$g/kg/hour to about 30 $\mu$g/kg/hour, either by 1–4 injections per day or by continuous subcutaneous infusions, for example, using a mini-pump. An intravenous bag solution may also be employed. The key factor in selecting an appropriate dose is the result obtained, as measured, for example, by increases in the circulating factor VIII coagulant level, a decrease in the clotting time (activated partial thromboplastin time), a reduction in the cuticle bleeding time and clinical evidence of a reduction in bleeding. Other useful measures of determining therapeutic effectiveness are known to one of ordinary skill in the art. The length of treatment needed to observe changes, and the interval following treatment for responses to occur, appear to vary depending on the desired effect.

Pharmaceutical compositions for use in such methods comprise the canine factor VIII polypeptides of the present invention and a pharmaceutically acceptable carrier or excipient therefor. By "pharmaceutically acceptable carrier or excipient" is meant a non-toxic solid, semisolid or liquid filler, diluent, encapsulating material or formulation auxiliary of any type. The carrier may also contain minor amounts of additives such as substances that enhance isotonicity and chemical stability, which are well-known in the pharmaceutical art. Such pharmaceutical compositions may be administered orally, rectally, parenterally, intravaginally, intraperitoneally, topically (as by powders, ointments, drops or transdermal patch), bucally, or as an oral or nasal spray. The term "parenteral" as used herein refers to modes of administration which include intravenous, intramuscular, intraperitoneal, intrasternal, subcutaneous and intraarticular injection and infusion.

The canine factor VIII polypeptide may also be suitably administered by sustained-release systems. Suitable examples of sustained-release compositions include semipermeable polymer matrices in the form of shaped articles, e.g., films, or microcapsules. Sustained-release matrices include polylactides (U.S. Pat. No. 3,773,919; EP 0 058 481), copolymers of L-glutamic acid and gamma-ethyl-L-glutamate (Sidman, U., et al., *Biopolymers* 22:547–556 (1983)), poly (2-hydroxyethyl methacrylate) (Langer, R., et al., *J. Biomed. Mat. Res.* 15:167–277 (1981); Langer, R., *Chem. Tech.* 12:98–105 (1982)), ethylene vinyl acetate (Langer et al., Id.) and poly-D(–)-3-hydroxybutyric acid (EP 0 133 988). Sustained-release canine factor VIII polypeptide compositions also include liposomally entrapped canine factor VIII polypeptide. Liposomes comprising canine factor VIII polypeptide may be prepared by any of a variety of methods that have been well-described in the art (See U.S. Pat. Nos. 4,485,045 and 4,544,545; Epstein et al., *Proc. Natl. Acad. Sci.* (*USA*) 82:3688–3692 (1985); Hwang et al., *Proc. Natl. Acad. Sci.* (*USA*) 77:4030–4034 (1980); EP 0 036 676; EP 0 052 322; EP 0 088 046; EP 0 102 324; EP 0 142 641; EP 0 143 949; DE 3,218,121; and JP 83-118008. Ordinarily, the liposomes are of the small (about 200–800 Angstroms) unilamellar type in which the lipid content is greater than about 30 mol. percent cholesterol, the selected proportion being adjusted for the optimal canine factor VIII polypeptide therapy.

For parenteral administration, in one embodiment, the canine factor VIII polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the canine factor VIII polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The canine factor VIII polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers may result in the formation of canine factor VIII polypeptide salts.

Canine factor VIII polypeptide to be used for therapeutic administration must be sterile. Sterility is readily accomplished by filtration through sterile filtration membranes (e.g., 0.2 micron membranes). Therapeutic canine factor VIII polypeptide compositions generally are placed into a container having a sterile access port, for example, an intravenous solution bag or vial having a stopper pierceable by a hypodermic injection needle.

Canine factor VIII polypeptide ordinarily will be stored in unit or multi-dose containers, for example, sealed ampules or vials, as an aqueous solution or as a lyophilized formulation for reconstitution. As an example of a lyophilized formulation, 10-ml vials are filled with 5 ml of sterile-filtered 1% (w/v) aqueous canine factor VIII polypeptide solution, and the resulting mixture is lyophilized. The infusion solution is prepared by reconstituting the lyophilized canine factor VIII polypeptide using U.S.P. water that is suitable for injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for canine administration. In addition, the polypeptides of the present invention may be employed in conjunction with other therapeutic compounds.

Having now described the present invention in detail, the same will be more clearly understood by reference to the following examples, which are included herewith for purposes of illustration only and are not intended to be limiting of the invention.

EXAMPLES

Example 1

Isolation and Cloning of Canine Factor VIII Gene

The following text details the methods that were used to characterize the canine cDNA sequence along with the proximal promoter and two factor VIII introns. Two features pertaining to the nature of the factor VIII sequence were especially challenging in the conduct of these studies: the large size of the factor VIII cDNA (~8 kb) and the extremely low abundance of factor VIII mRNA (~1/2,000,000 that of albumin).

Nucleic Acid Isolation

Whole blood or liver is obtained from a male canine of mixed breed. Total RNA was extracted from 100 mg of liver tissue using the TRIZOL reagent (Life Technologies, Inc.; Rockville, Md.) as per the manufacturer's instructions.

Genomic DNA was isolated from liver samples by phenol extraction as follows: 400 µl of Buffer 1 (100 mM Tris-HCl pH 8.0, 40 mM EDTA, 0.2% SDS) was added to approximately 50 mg of liver tissue and frozen for 30 minutes at −20° C. To thawed tissue, 1 to 2 mg of powdered proteinase K was added and allowed to incubate overnight at 56° C. or until tissue was dissolved. 500 µl of Tris-buffered phenol was added and gently mixed, and then centrifuged at 10,000 g for 2 minutes. The upper aqueous layer was removed to a clean tube and 500 μl of choroform:butanol (4:1) was added, mixed gently for 5 minutes, then centrifuged at 10,000 g for 1 minute. This step was repeated twice. 2× volume of 95% ethanol and ⅒ volume of 3 M sodium acetate pH 5.4 was added to the removed upper layer and allowed to precipitate at −20° C. for 15 minutes. Precipitated DNA was removed and dissolved in 250 μl of TE pH 8.0 (10 mM Tris-HCl, 1 mM EDTA).

Alternatively, genomic DNA is extracted from whole blood samples by salt extraction as follows: 5 ml of whole blood is mixed together with 5 ml of $TKM_1$ buffer (10 mM Tris-HCl pH 7.6, 10 mM KCl, 10 mM $MgCl_2$, 2 mM EDTA). Cells are lysed by adding 1.25 ml of 10% Nonidet P-40 (BDH) and the mixture is centrifuged at 600 to 700 g for ten minutes at room temperature. Following removal of the supernatant, the nuclear pellet is washed in 5 ml of $TKM_1$. Washing is repeated twice followed by resuspension of the pellet in 800 μl of $TKM_2$ buffer (10 mM Tris-HCl pH 7.6, 10 mM KCl, 10 mM $MgCl_2$, 0.4 M NaCl, 2 mM EDTA). The mixture is incubated at 50° C. for twenty minutes after the addition of 50 μl of 10% SDS (ICN). 400 μl of 5 M NaCl (ICN) is added and after thorough mixing, the contents are centrifuged at 11,000 g for 5 minutes. DNA is precipitated by adding 2.4 ml of ethanol at room temperature and inverting several times. DNA is spooled and dissolved in 200 μl of TE pH 8.0 (10 mM Tris-HCl, 1 mM EDTA) by incubation at 65° C. for several hours.

Factor VIII cDNA Synthesis

10 μg of total liver RNA was reverse transcribed as follows. In a final volume of 8 μl, 25 pmoles of a 3' oligonucleotide primer was annealed to total RNA by heating the sample to 65° C. and slowly cooling to 30° C. The sample was stored on ice and to this were added 17 μl of a pre-mixed cocktail consisting of 5 μl of 5×AMV-RT buffer (final concentration: 50 mM Tris-HCl pH 8.3, 50 mM KCl, 8 mM $MgCl_2$), 4 μl of 2.5 mM dNTP mix, 1 μl 0.1 M DTT, 1 μl RNAsin (Promega), 2 μl (70 units) of AMV Reverse Transcriptase (Life Technologies, Inc.), and 4 μl of sterile water. The contents were mixed and incubated at 43° C. for 4 hours or overnight.

Polymerase Chain Reaction

The resulting cDNA was used as a template for amplification by PCR to generate the following fragments, although not necessarily in sequential order: Fragment one encompassing the promoter region starting at 70 nucleotides upstream of the signal peptide to exon three, fragment three from exon three to exon eight, fragment four from exon eight to exon 13, fragment five in exon fifteen, fragment six from exon fifteen to exon twenty, fragment seven from exon twenty to exon twenty three, fragment eight from exon twenty three to exon twenty five, and fragment nine from exon twenty five to the 3' end of exon twenty six. Genomic DNA was used as a template for PCR amplification of fragments in exon 14 and for promoter sequence back to 40 nucleotides upstream of the assumed transcriptional start site. First round PCR was carried out using 2.5 units of Taq DNA polymerase (BRL/Life Technologies), 5 μl of 10×PCR buffer (200 mM Tris-HCl pH 8.4, 500 mM KCl, 15 mM $MgCl_2$), 4 μl of 2.5 mM dNTP's (Sigma), 1 μl (50 pmoles) of each of human factor VIII-specific, or a combination of human- and canine-specific, 5' and 3' primers which spanned one or more exons, in a final volume of 50 μl. Negative controls in which cDNA or genomic DNA was omitted from the PCR were included for each pair of primers. The template for the second round PCR amplifications consisted of 1 μl of micro-filtered (Centricon 30; Amicon) first round product and a second set of either one of the original primers and a nested primer, or nested 5' and 3' primers. Primer sequences for amplifying specific fragments encompassing the promoter region, signal peptide and exons one to twenty-five and the 5' end of exon 26 were as follows (Note: primer designations indicate "HS" (human-specific), "CS" (canine-specific) or "MS" (mouse-specific); "D", amplifying the region downstream of the 5' primer or "U", amplifying the region upstream of the 3' primer; "AA n" (where "n" is a number) refers to the corresponding amino acid number in the published human factor VIII sequence (Wood, W. I., et al., Nature 312:330–336 (1984))).

Fragment One:
Reverse Transcription primer:
"CS-AA-412-U": 5'CCGCGTAGGACCATTGTTCAA 3' (SEQ ID NO:6)
First Round:
"HS-nt -70-D": 5'GGGAGCTAAAGATATTTTAGA 3' (SEQ ID NO:7)
"CS-AA-173-U": 5'GGCTCCAATGAGGTCTGAAT 3' (SEQ ID NO:8)
PCR cycles: 94° C. for 2 minutes, 48° C. for 1 minute, 72° C. for 3 minutes
Second Round:
"HS-nt -70-D": (SEQ ID NO:7)
"CS-AA-113-U": 5'GCTGGTCTGATCCTCATACT 3' (SEQ ID NO:9)
PCR cycles: as for First Round above
Fragment Two:
Reverse transcription primer:
"CS-AA-173-U": (SEQ ID NO:8)
First Round:
"HS-AA-1-D": 5'GCCACCAGAAGATACTACC 3' (SEQ ID NO:10)
"CS-AA-173-U": (SEQ ID NO:8)
PCR cycles: As for Fragment One above
Second Round:
"HS-AA-1-D": (SEQ ID NO:10)
"CS-AA-113-U": (SEQ ID NO:9)
PCR cycles: as for First Round above
Fragment Three:
Reverse Transcription primer:
"CS-AA-412-U": (SEQ ID NO:6)
First Round:
"HS-nt-70-D": (SEQ ID NO:7)
"HS-AA-408-U": 5'TTTATAACTTCTGTCATCGGG 3' (SEQ ID NO:11)
PCR cycles: As for Fragment One above
Second Round:
"HS-AA-76-D": 5'CCAGGCTGAGGTTTATGATAC 3' (SEQ ID NO:12)
"CS-AA-385-U": 5'CTCCTCTCAGCAGCATTATA 3' (SEQ ID NO:13)
PCR cycles: As for First Round above
Fragment Four:
Reverse Transcription primer:
"CS-AA-753-U": 5'TTGCCTAGTGCTAGGGTGTC 3' (SEQ ID NO:14)
First Round:
"CS-AA-375-D": 5'GCCAAGAAGCATCCTAAAACT 3' (SEQ ID NO:15)
"HS-AA-747-U": 5'TCTTGAATTCTGGGAGAAGCT 3' (SEQ ID NO:16)
PCR cycles: 94° C. for 2 minutes, 58° C. for 1 minute, 72° C. for 3 minutes
Second Round:
"CS-AA-375-D": (SEQ ID NO:15)

"HS-AA-747-U": (SEQ ID NO:16)
PCR cycles: As for First Round above
Fragment Five:
Reverse Transcription primer:
"CS-AA-2055-U": 5'GGCATTGATTGATCCGGAATA 3' (SEQ ID NO:17)
First Round:
"CS-AA-1633-D": 5'AAAGGCTGTGCTCTCAAAAC 3' (SEQ ID NO:18)
"CS-AA-2040-U": 5'CCACTGTCCATATTGTCCTGA 3' (SEQ ID NO:19)
PCR cycles: 94° C. for 2 minutes, 48° C. for 1 minute, 72° C. for 2 minutes
Second Round:
"CS-AA-1633-D": (SEQ ID NO:18)
"CS-AA-1751-U": 5'CTCCACGGTATAAGGGCTGAG3' (SEQ ID NO:20)
PCR cycles: As for First Round above
Fragment Six:
Reverse Transcription primer:
"HS-AA-2055-U": (SEQ ID NO:17)
First Round:
"CS-AA-1633-U": (SEQ ID NO:18)
"CS-AA-2055-U": (SEQ ID NO:17)
PCR cycles: 94° C. for 2 minutes, 48° C. for 1 minute, 72° C. for 1.5 minutes
Second Round:
"CS-AA-1702-D": 5'CAGTGGAGCGTCTCTGGGATT 3' (SEQ ID NO:21)
"CS-AA-2043-U": 5'ATATTGTCCTGAAGCTGTAA 3' (SEQ ID NO:22)
PCR cycles: As for First Round above
Fragment Seven:
Reverse Transcription primer:
oligo dT (12–18mer; Life Technologies, Inc., Rockville, Md.)
First Round:
"CS-AA-2002-D": 5'TCGGCGAGCACCTGCAA 3' (SEQ ID NO:23)
"CS-AA-2170-U": 5'ACAGCCCAAGAGCTCCA 3' (SEQ ID NO:24)
PCR cycles: 94° C. for 2 minutes, 48° C. for 1 minute, 72° C. for 2 minutes
Second Round:
"CS-AA-2008-D": 5'GCCGGGATGAGCACTCT-GTTTCTG 3' (SEQ ID NO:25)
"CS-AA-2170-U": (SEQ ID NO:23)
PCR cycles: 94° C. for 2 minutes, 52° C. for 1 minute, 72° C. for 2 minutes
Fragment Eight:
Reverse Transcription primer: oligo dT (Life Technologies, Inc.)
First Round:
"HS-AA-2260-U": 5'TTGACTGCTGGAGATGAGGAA 3' (SEQ ID NO:26)
PCR cycles: 94° C. for 2 minutes, 48° C. for 1 minute, 72° C. for 2 minutes
Second Round:
"CS-AA-2151-D": 5'GCACCCAACCCATTACAGCAT 3' (SEQ ID NO:27)
"HS-AA-2260-U": (SEQ ID NO:25)
PCR cycles: As for First Round above
Fragment Nine:
Reverse Transcription primer: oligo dT (Life Technologies, Inc.)
First Round:
"CS-AA-2151-D": (SEQ ID NO:27)
"HS-AA-2326-U": 5'GCAGCCCAGAACCTCCAT 3' (SEQ ID NO:28)
PCR cycles: 94° C. for 2 minutes, 48° C. for 2 minutes, 72° C. for 3 minutes
Second Round:
"CS-AA-2246-D": 5'GGGGTGAAATCTCTCCTCAT 3' (SEQ ID NO:29)
"HS/MS-AA-2323-U": 5'CCTCCAGCCTCAGAG-CAATTT 3' (SEQ ID NO:30)
PCR cycles: As for First Round above
Exon Fourteen:
Fragment A:
First Round:
"CS-AA-715-D": 5'TTGATGATTATTATGAGGACA 3' (SEQ ID NO:31)
"HS-AA-1212-U": 5'AGGCAAAACTACATTCTCTTG 3' (SEQ ID NO:32)
PCR cycles: 94° C. for 2 minutes, 52° C. for 2 minutes, 72° C. for 3 minutes
Fragment B:
First Round:
"CS-AA-1149-D": 5'GGTGGTAGTAGGAGAGGATGA 3' (SEQ ID NO:33)
"CS-AA-1650-U": 5'TATTTCCCTTTGATGGTGTTT 3' (SEQ ID NO:34)
PCR cycles: 94° C. for 2 minutes, 58° C. for 1 minute, 72° C. for 3 minutes
Fragment C:
First Round:
"HS-AA-1633-D": 5'AAAGGCTGTGCTCTCAAAAC 3' (SEQ ID NO:35)
"CS-AA-1712-U": 5'ACTCATCCCATAATCCCAGAG 3' (SEQ ID NO:36)
PCR cycles: 94° C. for 1 minute, 58° C. for 1 minute, 72° C. for 2 minutes
Promoter Fragment:
First Round:
"HS-prom-nt-210-D":5'GGCTGCTTCCCACTGATAAA 3' (SEQ ID NO:37)
"HS-prom-nt-20-U":5'CTGGAGAAGCAAAAGGTTAAT 3' (SEQ ID NO:38)
PCR cycles: 94° C. for 2 minutes, 37° C. for 1 minute, 72° C. for 3 minutes Following amplification, 10 µl of PCR product were mixed with 2 µl of loading dye (6×solution: 0.25% bromophenol blue (Sigma), 0.25% xylene cyanol FF (Sigma), 15% Ficoll (Type 400; Pharmacia) in water), and electrophoresed through an 8% polyacrylamide gel in 1×TBE pH 8.0 (10×) solution: 0.9 M Tris-borate (ICN), 0.04 M EDTA (BDH)) at 100–140 volts for one hour on a Mighty Small electrophoresis apparatus (Hoeffer). 200 ng of pGem DNA ladder (Promega) were electrophoresed alongside the samples. DNA was visualized by staining the gel in a 1% ethidium bromide (Life Technologies) solution and viewing under a UV transilluminator (Fotoprep; BioCan Scientific). The remainder of the PCR product was subsequently electrophoresed through 1% Low Melting Point Agarose (Life Technologies), or 3% NuSieve agarose (Mandel) in 1×TBE pH 8.0 along with pGem DNA marker. Bands of the correct size were then excised from the gel, and DNA was extracted from each gel slice using phenol (Boehringer Mannheim) buffered with high salt TE pH 8.0 (500 mM NaCl, 10 mM Tris-HCl (both ICN), 1 mM EDTA (BDH)). Following precipitation in ethanol using tRNA as a carrier, the resulting pellet was washed in 70% ethanol, air dried and reconstituted in 7–10 µl of TE pH 8.0.

Example 2
Sequencing of Canine Factor VIII Gene

To facilitate sequencing, gel purified PCR fragments were cloned into either PT7 (Novagen) or PCR 2.0 or 2.1 (Invitrogen) as per manufacturer's instructions. DNA for sequencing was prepared using the standard alkaline lysis method on a small scale. Three clones of each fragment were sequenced, using Sequenase Version 2.0 (USB), 5 µCi $\alpha^{32}$P-dATP (NEN, Mandel), and various amplification and/or sequencing primers (Core Facility, Queen's University, Kingston, Ontario, Canada), following alkaline denaturation of miniprep DNA. Sequencing was by the Sanger dideoxy method, as outlined in the Sequenase Version 2.0 kit (USB). 2–4 µl of the reactions were denatured at 85° C. for 3 minutes and immediately loaded onto a 6% denaturing polyacrylamide gel in 1×TBE pH 8.9 (10×solution: 8.9 mM Tris-borate (ICN), 20 mM EDTA (BDH)). Samples were electrophoresed at 65–70 W on a Model S2 sequencing apparatus (Life Technologies) for 2–6 hours. Autoradiography was carried out by exposing Cronex Ultra Vision G film (Dupont) to the gel for a period of 2 hours to 3 days. The resulting sequence was analyzed independently by at least two people and sequence information was stored with the assistance of DNAsis software (Hitachi) for further analysis; results are shown below in the Results section.

The sequence was subsequently confirmed by RT-PCR using the Expand High Fidelity PCR System (Boehringer Mannheim) according to the manufacturer's recommendations. The following pairs of canine primers and PCR cycle conditions were used (Note: An initial denaturation step at 94° C. for 2 minutes was followed by 10 initial cycles and 20 subsequent cycles where the third step included an autoextension of 20 seconds per cycle. All PCR reactions concluded with an incubation at 72° C. for 15 minutes.):

Fragment One A:
Reverse Transcription primer:
"CS-AA-855-U": 5'CTGGCTCAGGAGTAAATTCTC 3' (SEQ ID NO:39)
First Round:
"HS-nt-70-D": (SEQ ID NO:7)
"CS-AA-173-U": (SEQ ID NO:8)
PCR cycles: 94° C. for 1 minute, 50° C. for 1 minute, 72° C. for 3 minutes
Second Round:
"HS-nt-70-Xba1-D": 5'CCAGTTGAACATTTTCTA-GAAATAC 3' (SEQ ID NO:40)
"CS-AA-113-U": (SEQ ID NO:9)
PCR cycles: 94° C. for 1 minute, 52° C. for 1 minute, 72° C. for 3 minutes Fragment Two A:
Reverse Transcription primer: "CS-AA-855-U" (SEQ ID NO:39)
First Round:
"CS-AA-36-D": 5'GGATCTTTGCCACTCACCACGT-CAGT 3' (SEQ ID NO:41)
"CS-AA-674-U": 5'CTGAGAATGGGAAGAGGG-TAAGTGTGTC 3' (SEQ ID NO:42)
PCR cycles: 94° C. for 1 minute, 54° C. for 1 minute, 70° C. for 4 minutes
Second Round:
"HS-AA-76-D": (SEQ ID NO:12)
"CS-AA-617-U": 5'GCTGTGCATGATGTTAGAGAG 3' (SEQ ID NO:43)
PCR cycles: 94° C. for 1 minute, 48° C. for 30 seconds, 70° C. for 3 minutes Fragment Three A:
Reverse Transcription primer: "CS-AA-855-U" (SEQ ID NO:39)
First Round:
"CS-AA-400-D": 5'CCACCCCCAATGATAGAAGTC 3' (SEQ ID NO:44)
"CS-AA-855-U": (SEQ ID NO:39)
PCR cycles: 94° C. for 1 minute, 56° C. for 1 minute, 70° C. for 3 minutes
Second Round:
"CS-AA-400-D": (SEQ ID NO:44)
"CS-AA-844-D": 5'CTGTGACGGAGCTCTGGTCT-GAGACTT 3' (SEQ ID NO:45)
PCR cycles: 94° C. for 1 minute, 70° C. for 3 minutes Fragment Four A:
Reverse Transcription primer:
"CS-AA-2110-U": 5'GTTGCCATCCAGACTGTACAT 3' (SEQ ID NO:46)
First Round:
"CS-AA-1483-D": 5'CCAGGCTTGTCCGAAACATCT 3' (SEQ ID NO:47)
"CS-AA-1875-U": 5'CTCCTGCACTGTCACTTGTCT 3' (SEQ ID NO:48)
PCR cycles: 94° C. for 1 minute, 48° C. for 1 minute, 72° C. for 3 minutes
Second Round:
"CS-AA-1573-D": 5'CCCAGATACCAAGTGAAGAGT 3' (SEQ ID NO:49)
"CS-AA-1850-U": 5'GCCTGAGTGCACATCTTTCTC 3' (SEQ ID NO:50)
PCR cycles: As for First Round above Fragment Five A:
First Round:
"CS-AA-1779-D":5'CCTCTCGTCCCTACTCCTTCTATT 3' (SEQ ID NO:51)
"CS-AA-1980-U":5'GGATAGAGGTTGTAGACTGCCATT 3' (SEQ ID NO:52)
PCR cycles: 94° C. for 1 minute, 48° C. for 1 minute, 72° C. for 2 minutes Fragment Six A-1:
Reverse Transcription primer: oligo dT (Life Technologies, Inc.)
First Round:
"CS-AA-1867-D": 5'CATGGGAGACAAGTGACAGTGC 3' (SEQ ID NO:53)
"CS-nt-UTR-313-U": 5'CCTTCCGCCCGCCGCAG 3' (SEQ ID NO:54)
PCR cycles: 94° C. for 2 minutes, 50° C. for 1 minute, 72° C. for 3 minutes
Second Round:
"CS-AA-1930-D": 5'CTGGCTTAGTAATGGCTCAGGAT-CAA 3' (SEQ ID NO:55)
"HS-AA-2266-U": 5'TTGACTGCTGGAGATGAGGAA 3' (SEQ ID NO:56)
PCR cycles: As for First Round above Fragment Six A-2:
Reverse Transcription primer: oligo dT (Life Technologies, Inc.)
First Round:
"CS-AA-2151-D": (SEQ ID NO:27)
"CS-AA-UTR-48-U": 5'CGCGGGACAGGGCAGGGAG 3' (SEQ ID NO:57)
PCR cycles: 94° C. for 2 minutes, 48° C. for 2 minutes, 72° C. for 3 minutes
Second Round:
"CS-AA-2219-D": 5'GGAGACCTCAGGCAAATAAC-CCA 3' (SEQ ID NO:58)
"CS-AA-2299-U": 5'GTTCGAGACGGTTCCGCACA 3' (SEQ ID NO:59)
PCR cycles: 94° C. for 2 minutes, 50° C. for 1 minute, 72° C. for 3 minutes Fragment Six A-3:
First Round:
"CS-AA-2292-D": 5'CTGTGCGGAACCGTCTCGAAC 3' (SEQ ID NO:60)
"CS-nt-UTR-U": 5'AGACCTCGCTGTCGGCC 3' (SEQ ID NO:61)
PCR cycles: 94° C. for 2 minutes, 66° C. for 1 minute, 72° C. for 3 minutes Example 3
Library Screening of Canine Factor VIII Gene A genomic lambda library derived from male beagle whole blood (Stratagene cat. No 946802) was used to obtain the sequence of exon 26 and the 3' UTR. The library was plated onto 150 mm Petri dishes at a concentration of 10,000 pfu/plate. The recombinant phage were transferred to Hybond N+ membrane (Amersham), as described by the manufacturer. 1.2×10$^6$ pfu were screened using an oligolabelled (Oligolabelling Kit; Pharmacia, 50 µCi α$^{32}$P-dATP; NEN) canine-specific cDNA fragment which hybridized to exon 25 and exon 26 from amino acid residue 2246 to amino acid residue 2323. Three positive clones went through three rounds of plaque purification, after which one positive clone (clone 15) remained. DNA from clone 15 was isolated using a standard small scale phage prep method, and double digests of EcoRI, BamHI, HindIII and NotI (all from Life Technologies, Inc.) were carried out per manufacturer's suggested protocols. The restricted DNA was electrophoresed through a 1% agarose gel and transferred onto Hybond N+ (as per the manufacturer's instructions). The resulting fragment, designated "AA-2246-AA-2323," was oligolabelled (Oligolabelling Kit; Pharmacia, 50 µCi α$^{32}$P-dATP; Mandel) and hybridized to the membrane, and DNA fragments which contained exon 26 were identified. A 1.2 kb EcoRI/NotI and a 4 kb HindIII/NotI fragment were subcloned into PCR 2.0 (according to manufacturer's protocol). The 1.2 kb clone and part of the 4 kb clone were sequenced using a combination of dideoxy sequencing (Sequenase Ver. 2.0) and automated sequencing. 10 µl of PCR product were mixed with 2 µl of loading dye (6×solution: 0.25% bromophenol blue (Sigma), 0.25% xylene cyanol FF (Sigma), 15% Ficoll (Type 400; Pharmacia) in water), and electrophoresed through an 8% polyacrylamide gel in TBE buffer.

Example 4
Characterization of Canine Factor VIII Sequence

The sequences of the factor VIII PCR products were characterized by two methods. Individual PCR products were cloned into the "T-overhang" vector pCRII (Invitrogen) and, following bacterial transformation, three separate recombinant clones were sequenced manually. In addition, an aliquot of the PCR product was sequenced on an ABI automated sequencer. Overall, all regions of the canine gene have been sequenced a minimum of twice.

Results of this characterization, in combination with the results of the cloning and sequencing examples above, are shown below.

RESULTS
A. Canine Factor VIII Coding Sequence:

As shown in FIG. 1, the canine factor VIII cDNA comprises 7029 nucleotides of coding sequence (SEQ ID NO:1) (2343 amino acids; SEQ ID NO:2). The protein has a typical N-terminal hydrophobic 19 residue signal sequence (underlined in FIG. 1) followed by the internally repeated domain structure documented in the other factor VIII molecules characterized to date.

The canine factor VIII protein shows significant amino acid sequence identity with those of human (SEQ ID NO:3), mouse (SEQ ID NO:4) and pig (SEQ ID NO:5), as shown in FIG. 2 and Table 1.

TABLE 1

Amino Acid Sequence Identities Between Canine Factor VIII Protein and Factor VIII Proteins of Other Species.

| Protein Domain | Human | Mouse | Pig |
|---|---|---|---|
| A1 | 84% | 82% | 80% |
| a1 | 70% | 65% | 70% |
| A2 | 89% | 84% | 88% |
| B | 62% | 44% | 53% |
| a2 | 61% | 49% | 63% |
| A3 | 87% | 83% | 85% |
| C1 | 92% | 89% | 92% |
| C2 | 83% | 84% | 77% |

As has been previously documented in analyses of the amino acid sequence identity between human factor VIII protein and the murine and porcine proteins, the overall amino acid sequence identity between canine factor VIII protein and the human factor VIII protein is >80% . However, this level of sequence identity is not seen in the B domain of the canine protein, where levels of identity fall to between 44–62%. Along with the observation that factor VIII molecules lacking the B domain retain functional activity, these findings imply that this region of the protein does not play a critical role in the biological activity of factor VIII.

B. Conservation of Functional Sites

Canine factor VIII shows strong conservation of all functionally significant sites defined in the human sequence (see FIG. 2). Specifically, the regions adjacent to the thrombin cleavage sites at Arg366-Ser367 (human amino acid residues 372–373), Arg734-Ser735 (human 740–741) and Arg1681-Ser1682 (human 1689–1690) are all identical to the human sequence, as are the two Protein C cleavage sites that have been documented at Arg331-Met332 (human site 336–337) and Arg556-Gly557 (human site 562–563). In the vWF binding region, in the A3 domain, between residues 1666 and 1676 (human residues 1674–1684), four changes are noted, one of which is conservative in nature. All six tyrosine residues that are known to undergo sulfation in the human protein (at residues 346, 718, 719, 723, 1664 and 1680) are conserved in the canine sequence (at residues 340, 712, 713, 717, 1656 and 1672, respectively). Finally, the canine sequence possesses 31 potential N-glycosylation sites, 25 of which are located in the B domain and 15 of which are common to sites identified in human factor VIII.

C. 5' Flanking Sequence:

The start site of transcription in the canine has not been characterized, but the 208 nucleotides sequenced upstream of the initiation methionine (SEQ ID NO:62) show 74% sequence identity with the human 5' flanking region, implying that transcriptional regulation may well be similar in both species. In further support of this claim is the fact that sequence identity at the two proximal cis-acting sites in the human 5' UTR are conserved to levels of 87% for site 1 (HNF-1 site) and 87% for site 2 (NFκB and C/EBP site). In addition, the region adjacent to the alternative GATAA site in the human promoter (nt–35) is also conserved at the canine locus.

D. 3' Untranslated Region:

The 3' UTR in the canine factor VIII gene (SEQ ID NO:63) extends 1.5 kb compared to 1.8 kb in the human gene and only 155 nucleotides in the mouse. The sequence identity between the canine and human 3' UTRs is <15% and the canine sequence is characterized by a region of very high cytosine/guanine content (>70%) in the initial 700 nts downstream of the stop codon. These sequence characteristics may promote the formation of secondary structures that would enhance the stability of the canine factor VIII mRNA. At the end of the 3' UTR, two potential polyadenylation sequences occur within a 200 nt region in a manner enhance the stability of the canine factor VIII mRNA. At the end of the 3' UTR, signals within 400 nts.

E. Conclusions:

The sequence of the canine factor VIII gene has been characterized, including the full coding sequence (SEQ ID NO:1), 208 nucleotides of 5' UTR and 5' flanking sequence (SEQ ID NO:62) and 1.5 kb of 3' UTR (SEQ ID NO:63). While the overall amino acid sequence identity between the canine factor VIII protein (SEQ ID NO:2) and those from human (SEQ ID NO:3), mouse (SEQ ID NO:4) and pig (SEQ ID NO:5) is about 80%, this sequence identity is significantly reduced among the individual domains of the canine protein. All functionally important sites are conserved in the canine sequence, and the high level of sequence conservation in the 5' flanking sequence suggests that similar transcriptional control mechanisms may operate in the canine and human factor VIII genetic loci.

Acquisition of the canine factor VIII sequence represents a criticalstep in testing a strategy for hemophilia A gene therapy in the canine model of inherited factor VIII deficiency. With the use of the homologous factor VIII sequence, the evaluation of protocols to deliver effective long-term gene therapy to hemophilic canines will not be complicated by the inevitable development of alloantibodies to the human gene product.

Example 5
Transfection and In vivo Expression of Canine Factor VIII Gene

To facilitate in vivo studies of the canine factor VIII cDNA, a B domain deleted form of the canine factor VIII cDNA was constructed and this sequence was ligated into a recombinant adenovirus devoid of E1l, E2a and E3 sequences. ApaI sites, consisting of nucleotides GGGCCC, flanking the B domain in the encoded protein, are at nucleotide positions 2520 to 2525 and 4836 to 4841 (refer to FIG. 1 or SEQ ID NO:1). In this construct, the transgene is regulated by sequences from the mouse albumin promoter and there is a 5' intron (derived from the human Apo AI gene).

Approximately $4 \times 10^{12}$ recombinant adenoviral particles were infused via the cephalic veing into two hemophilia A dogs (Hemophilic Dog Colony, Queen's University, Kingston, Ontario, Canada). The dogs were bled daily and tested for levels of canine factor VIII, anti-factor VIII antibodies, and alanine transaminase, as well as for whole blood clotting time, using standard procedures.

As shown in FIG. 3, the pre-infusion factor VIII coagulant levels in both dogs were <0.3 unit/ml (measured against a human plasma standard by an activated partial thromboplastin time method). Within 24 hours of infusion, the factor VIII coagulant activities in both dog plasmas had increased to >4.0 unit/ml, and reached apeak of >18.0 unit/ml on day 2 post-infusion. The factor VIII levels in both dogs subsequently returned to close to pre-infusion levels by day 6 in one dog and day 9 in the second dog. These declines in factor VIII activity, as evidenced by increases in whole blood clotting time (FIG. 6), coincided with two events that contributed to the loss of factor VIII: an acute severe hepatotoxicity, demonstrated by increases in alanine transaminase activity (FIG. 5); and, as depicted in FIG. 4, the development of neutralizing anti-factor VIII antibodies (far worse in one of the two dogs). These data indicate that the extraordinarily high factor VIII levels achieved in these dogs may have been toxic to the synthesizing hepatocytes.

Taken together, these results demonstrate that the canine factor VIII gene is able to be successfully introduced into living animals, and that the so-introduced gene is expressed in vivo to produce active canine factor VIII protein. The inventors expect that any dosage effects leading to undesirable immunological or toxic reactions would be able to be overcome without undue experimentation, for example, by employing a genetic construct that is expressed at lower levels, e.g., has a weaker promoter.

Having now fully described the present invention in some detail by way of illustration and example for purposes of clarity of understanding, it will be obvious to one of ordinary skill in the art that the same can be performed by modifying or changing the practice of the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. An isolated nucleic acid molecule comprising a polynucleotide encoding a polypeptide having canine factor VIII biological activity and having a nucleotide sequence at least 90% identical to a reference sequence selected from the group consisting of:
   (a) the nucleotide sequence set forth in SEQ ID NO:1;
   (b) a nucleotide sequence encoding the canine factor VIII polypeptide having the complete amino acid sequence set forth in SEQ ID NO:2;
   (c) a nucleotide sequence encoding the mature canine factor VIII polypeptide having the amino acid sequence at positions 20 to 2343 in SEQ ID NO:2; and
   (d) a nucleotide sequence fully complementary to any of the nucleotide sequences in (a), (b), or (c).

2. The nucleic acid molecule of claim 1 wherein said polynucleotide has a nucleotide sequence at least 95% identical to said reference sequence.

3. The nucleic acid molecule of claim 1 wherein said polynucleotide has the complete nucleotide sequence set forth in SEQ ID NO:1.

4. The nucleic acid molecule of claim 1 wherein said polynucleotide has a nucleotide sequence encoding the canine factor VIII polypeptide having the complete amino acid sequence set forth in SEQ ID NO:2.

5. The nucleic acid molecule of claim 1 wherein said polynucleotide has a nucleotide sequence encoding the mature canine factor VIII polypeptide having the amino acid sequence set forth at positions 20 to 2343 in SEQ ID NO:2.

6. A method for making a recombinant vector comprising inserting the isolated nucleic acid molecule of claim 1 into a vector.

7. The method of claim 6, wherein said vector is an expression vector.

8. A method for making a genetic construct comprising operably linking the isolated nucleic acid molecule of claim 1 to a heterologous regulatory DNA sequence.

9. A genetic construct made by the method of claim 8.

10. A method for making a recombinant vector comprising inserting the genetic construct of claim 9 into a vector.

11. A recombinant vector made according to the method of claim 6 or claim 10.

12. A method of making a recombinant host cell, comprising introducing the nucleic acid molecule of claim 1 into a host cell.

13. A method of making a recombinant host cell, comprising introducing the recombinant vector of claim 11 into a host cell.

14. A recombinant host cell comprising the nucleic acid molecule of claim 1.

15. A recombinant host cell comprising the recombinant vector of claim 11.

16. A method for producing an isolated canine factor VIII polypeptide, comprising culturing the recombinant host cell of claim 14 under conditions such that said polypeptide is expressed, and isolating said polypeptide.

17. An isolated nucleic acid molecule comprising a polynucleotide encoding a polypetpide having canine factor VIII biological activity and having a nucleotide sequence at least 90% identical to a reference sequence selected from the group consisting of:
   (a) the complete nucleotide sequence of the deposited cDNA clone designated pBK-cmV (1-6#23) canine FVIII (ATCC Accession No. 209475);

(b) a nucleotide sequence encoding the canine factor VIII polypeptide having the complete amino acid sequence encoded by the deposited cDNA clone designated pBK-cmV (1-6#23) canine FVIII (ATCC Accession No. 209475);

(c) a nucleotide sequence encoding the mature canine factor VIII polypeptide having the amino acid sequence encoded by the deposited cDNA clone designated pBK-cmV (1-6#23) canine FVIII (ATCC Accession No. 209475); and (d) a nucleotide sequence fully complementary to any of the nucleotide sequences of (a), (b) or (c).

18. The isolated nucleic acid molecule of claim 17, wherein said polynucleotide has a nucleotide sequence at least 95% identical to said reference sequence.

19. The nucleic acid molecule of claim 17, wherein said polynucleotide has the complete nucleotide sequence of the deposited cDNA clone designated pBK-cmV (1-6#23) canine FVIII (ATCC Accession No. 209475).

20. The nucleic acid molecule of claim 17, wherein said polynucleotide has a nucleotide sequence encoding the canine factor VIII polypeptide having the complete amino acid sequence encoded by the deposited cDNA clone designated pBK-cmV (1-6#23) canine FVIII (ATCC Accession No. 209475).

21. The nucleic acid molecule of claim 17, wherein said polynucleotide has a nucleotide sequence encoding the mature canine factor VIII polypeptide having the amino acid sequence encoded by the deposited cDNA clone designated pBK-cmV (1-6#23) canine FVIII (ATCC Accession No. 209475).

22. A method for making a recombinant vector comprising inserting the isolated nucleic acid molecule of claim 17 into a vector.

23. The method of claim 22, wherein said vector is an expression vector.

24. A method for making a genetic construct comprising operably linking the isolated nucleic acid molecule of claim 17 to a heterologous regulatory DNA sequence.

25. A genetic construct made by the method of claim 24.

26. A method for making a recombinant vector comprising inserting the genetic construct of claim 25 into a vector.

27. A recombinant vector made according to the method of claim 22 or claim 26.

28. A method of making a recombinant host cell, comprising introducing the nucleic acid molecule of claim 17 into a host cell.

29. A method of making a recombinant host cell, comprising introducing the recombinant vector of claim 27 into a host cell.

30. A recombinant host cell comprising the nucleic acid molecule of claim 17.

31. A recombinant host cell comprising the recombinant vector of claim 27.

32. The recombinant host cell of claim 30 or claim 31, wherein said recombinant host cell is a prokaryotic cell.

33. The recombinant host cell of claim 30 or claim 31, wherein said recombinant host cell is a eukaryotic cell.

34. The recombinant host cell of claim 33, wherein said eukaryotic cell is a mammalian cell.

35. The recombinant host cell of claim 34, wherein said mammalian cell is a canine cell.

36. A method for producing an isolated canine factor VIII polypeptide, comprising culturing the recombinant host cell of claim 30 or claim 31 under conditions such that said polypeptide is expressed, and isolating said polypeptide.

37. A method for producing an isolated canine factor VIII polypeptide, comprising culturing the recombinant host cell of claim 15 under conditions such that said polypeptide is expressed, and isolating said polypeptide.

* * * * *